United States Patent
Wu et al.

(10) Patent No.: US 9,074,206 B2
(45) Date of Patent: Jul. 7, 2015

(54) COMPOSITIONS AND METHODS FOR MICRO-RNA EXPRESSION PROFILING OF COLORECTAL CANCER

(75) Inventors: Ying Wu, Shanghai (CN); Hongguang Zhu, Shanghai (CN); Jian Li, Shanghai (CN); Liang Xu, Shanghai (CN); Wilhelmus F. J. Verhaegh, Eindhoven (NL); Yiping Ren, Shanghai (CN); Angel Janevski, Briarcliff Manor, NY (US); Vinay Varadan, Briarcliff Manor, NY (US); Zhaoyong Li, Shanghai (CN); Nevenka Dimitrova, Briarcliff Manor, NY (US)

(73) Assignee: Fudan University, Shanghai (CN)

( * ) Notice: Subject to any disclaimer, the term of this patent is extended or adjusted under 35 U.S.C. 154(b) by 840 days.

(21) Appl. No.: 13/129,289

(22) PCT Filed: Nov. 13, 2009

(86) PCT No.: PCT/IB2009/055057
§ 371 (c)(1),
(2), (4) Date: Aug. 2, 2011

(87) PCT Pub. No.: WO2010/055487
PCT Pub. Date: May 20, 2010

(65) Prior Publication Data
US 2011/0281756 A1  Nov. 17, 2011

(30) Foreign Application Priority Data
Nov. 13, 2008  (CN) .......................... 2008 1 0176712

(51) Int. Cl.
*C12Q 1/68* (2006.01)
*C12N 15/11* (2006.01)

(52) U.S. Cl.
CPC ............ *C12N 15/111* (2013.01); *C12Q 1/6886* (2013.01); *C12Q 2600/158* (2013.01); *C12N 2310/141* (2013.01); *C12N 2320/10* (2013.01); *C12N 2330/10* (2013.01); *C12N 2330/31* (2013.01); *C12Q 1/6816* (2013.01)

(58) Field of Classification Search
CPC ..................... C12N 215/111; C12N 2310/141; C12N 2320/10; C12Q 1/6816
USPC ..................... 506/9; 435/6.12, 6.14
See application file for complete search history.

(56) References Cited

FOREIGN PATENT DOCUMENTS

| WO | WO 2005/078139 | 8/2005 |
|---|---|---|
| WO | WO 2005/118806 | 12/2005 |
| WO | WO 2007/081740 | 7/2007 |
| WO | WO 2007/103808 | 9/2007 |

OTHER PUBLICATIONS

Agilent and Stratagene Genomics Product Portfolio: Detection and Quantification, Data Analysis, Sample Preparation; pp. 1-15, published Jun. 2008.*
Bandres et al. (2006). Identification by Real-time PCR of 13 mature microRNAs differentially expressed in colorectal cancer and non-tumoral tissues. Molecular Cancer. 5:29.
Blenkiron et al. (2007). miRNAs in cancer: Approaches, aetiology, diagnostics, and therapy. Hum. Mol. Genet. 16, R106-R113.
Calin et al. (2007). Chromosomal rearrangements and microRNAs: a new cancer link with clinical implications. J. Clin. Invest. 117, 2059-2066.
Cummins et al. (2006). Implications of micro-RNA profiling for cancer diagnosis. Oncogene. 25:6220-6227.
Douglas, E. J. et al. (2004). Array comparative genomic hybridization analysis of colorectal cancer cell lines and primary carcinomas. Cancer Res. 64:4817-4825.
International Search Report corresponding to International Application No. PCT/IB2009/05505, dated Aug. 10, 2010.
Kitahara, et al. (2001). Alterations of gene expression during colorectal carcinogenesis revealed by cDNA microarrays after laser-capture microdissection of tumor tissues and normal epithelia. Cancer Res. 61:3544-3549.
Lee Eun Jon et al. (2006). Expression profiling identifies microRNA signature in pancreatic cancer. Int J Cancer 120:1046-1054.
Lu J. et al. (2005). MicroRNA expression profiles classify human cancers. Nature. 435, 834-838.
Mayr et al. (2007) Disrupting the pairing between let-7 and Hmga2 enhances oncogenic transformation. Science. 315:1576-1579.
Michael et al. (2003). Reduced accumulation of specific microRNAs in colorectal neoplasia. Mol. Cancer Res. 1:882-891.
Schepeler et al. (2008). Diagnostic and prognostic microRNAs in stage II colon cancer. Cancer Research. 68:6416-6424.

(Continued)

*Primary Examiner* — Jim Ketter
*Assistant Examiner* — Antonio Galisteo Gonzalez
(74) *Attorney, Agent, or Firm* — Jenkins, Wilson, Taylor & Hunt, P.A.

(57) ABSTRACT

The present invention relates compositions and methods for microRNA (miRNA) expression profiling of colorectal cancer. In particular, the invention relates to a diagnostic kit of molecular markers for identifying one or more mammalian target cells exhibiting or having a predisposition to develop colorectal cancer, the kit comprising a plurality of nucleic acid molecules, each nucleic acid molecule encoding a miRNA sequence, wherein one or more of the plurality of nucleic acid molecules are differentially expressed in the target cells and in one or more control cells, and wherein the one or more differentially expressed nucleic acid molecules together represent a nucleic acid expression signature that is indicative for the presence of or the predisposition to develop colorectal cancer. The invention further relates to corresponding methods using such nucleic acid expression signatures for identifying one or more mammalian target cells exhibiting or having a predisposition to develop colorectal cancer as well as for preventing or treating such a condition. Finally, the invention is directed to a pharmaceutical composition for the prevention and/or treatment of colorectal cancer.

6 Claims, 20 Drawing Sheets

(56) References Cited

OTHER PUBLICATIONS

Schetter et al. (2008). MicroRNA expression profiles associated with prognosis and therapeutic outcome in colon adenocarcinoma. JAMA. 299:425-436.

Slaby et al. (2007). Altered expression of miR-21, miR-31, miR-143 and miR-145 is related to clinicopathologic features of colorectal cancer. Oncology. 72:397-402.

Volina et al. (2006). A microRNA expression signature of human solid tumors defines cancer gene targets. Proc. Natl. Acad. Sci. USA 103:2257-2261.

Xi et al. (2007). Prognostic Values of microRNAs in Colorectal Cancer. Biomarker Insights. 2:113-121.

Esquela-Kerscher, A. and Slack, F.J. (2006). Oncomirs—microRNAs with a role in cancer. Nat. Rev. Cancer. 6:259-269.

* cited by examiner

FIGURE 1

| miRNA | Sequence (5' → 3') |
|---|---|
| hsa-miR-224 | caagucacuagugguuccguu |
| hsa-miR-96 | uuuggcacuagcacauuuugcu |
| hsa-miR-21 | uagcuuaucagacugauuuga |
| hsa-miR-182 | uuuggcaaugguagaacucacacu |
| hsa-miR-183 | uauggcacugguagaauucacu |
| hsa-miR-221 | agcuacauugucugcuggguuuc |
| hsa-miR-497 | cagcagcacacuguggugu |
| hsa-miR-106a | aaaagugcuuacagugcagguag |
| hsa-miR-106b | uaaagugcugacagugcagau |
| hsa-miR-18b | uaaggugcaucuagugcaguuag |
| hsa-miR-30a | uguaaacauccucgacuggaag |
| hsa-miR-135b | uauggcuuuucauuccuauguga |
| hsa-miR-93 | caaagugcuguucgugcagguag |
| hsa-miR-17 | caaagugcuuacagugcagguag |
| hsa-miR-20b | caaagugcucauagugcagguag |
| hsa-miR-24 | uggcucaguucagcaggaacag | hsa-miR-224 hsa-miR-96 hsa-miR-21 hsa-miR-182 hsa-miR-183 hsa-miR-221 hsa-miR-497 hsa-miR-106b hsa-miR-106a hsa-miR-18b hsa-miR-30a hsa-miR-135b hsa-miR-24

FIGURE 5

| Name | TUMOR | DISCOVERY REGULATION | DISCOVERY ACCURACY (%) | VALIDATION REGULATION | VALIDATION ACCURACY (%) |
|---|---|---|---|---|---|
| Adenoma | | | | | |
| hsa-miR-376a | Adenoma | DOWN | 85 | DOWN | 86 |
| hsa-miR-429 | Adenoma | UP | 77 | UP | 70 |
| hsa-miR-451 | Adenoma | DOWN | 79 | DOWN | 75 |
| hsa-miR-99a | Adenoma | DOWN | 89 | DOWN | 81 |
| Adenoma & Carcinoma | | | | | |
| hsa-miR-139-5p | Adenoma | DOWN | 87 | DOWN | 93 |
| | Carcinoma | DOWN | 89 | DOWN | 89 |
| hsa-miR-497 | Adenoma | DOWN | 83 | DOWN | 88 |
| | Carcinoma | DOWN | 95 | DOWN | 95 |
| hsa-miR-378* | Adenoma | DOWN | 79 | DOWN | 74 |
| | Carcinoma | DOWN | 90 | DOWN | 91 |
| hsa-miR-182 | Adenoma | UP | 87 | UP | 76 |
| | Carcinoma | UP | 82 | UP | 88 |
| hsa-miR-20b | Adenoma | UP | 82 | UP | 81 |
| | Carcinoma | UP | 91 | UP | 92 |
| hsa-miR-17* | Adenoma | UP | 77 | UP | 70 |
| | Carcinoma | UP | 85 | UP | 85 |
| hsa-miR-376c | Adenoma | DOWN | 89 | DOWN | 89 |
| | Carcinoma | DOWN | 71 | DOWN | 79 |
| hsa-miR-20a* | Adenoma | UP | 72 | UP | 82 |
| | Carcinoma | UP | 82 | UP | 86 |
| hsa-miR-638 | Adenoma | DOWN | 73 | DOWN | 79 |
| | Carcinoma | DOWN | 81 | DOWN | 83 |
| hsa-miR-335* | Adenoma | UP | 73 | UP | 74 |
| | Carcinoma | UP | 79 | UP | 81 |
| hsa-miR-342-5p | Adenoma | DOWN | 77 | DOWN | 76 |
| | Carcinoma | DOWN | 80 | DOWN | 78 |
| hsa-miR-34b* | Adenoma | UP | 83 | UP | 80 |
| | Carcinoma | UP | 79 | UP | 82 |
| hsa-miR-145* | Adenoma | DOWN | 82 | DOWN | 77 |
| | Carcinoma | DOWN | 79 | DOWN | 74 |
| hsa-miR-552 | Adenoma | UP | 77 | UP | 70 |
| | Carcinoma | UP | 83 | UP | 84 |

FIGURE 5 (cont.)

|  |  | DISCOVERY | | VALIDATION | |
|---|---|---|---|---|---|
| Name | TUMOR | REGULATION | ACCURACY (%) | REGULATION | ACCURACY (%) |
| Carcinoma | | | | | |
| hsa-miR-424 | Carcinoma | UP | 91 | UP | 88 |
| hsa-miR-378 | Carcinoma | DOWN | 91 | DOWN | 89 |
| hsa-miR-375 | Carcinoma | DOWN | 92 | DOWN | 93 |
| hsa-miR-139-3p | Carcinoma | DOWN | 86 | DOWN | 88 |
| hsa-miR-18b | Carcinoma | UP | 89 | UP | 87 |
| hsa-miR-18a | Carcinoma | UP | 90 | UP | 87 |
| hsa-miR-650 | Carcinoma | DOWN | 86 | DOWN | 89 |
| hsa-miR-194* | Carcinoma | DOWN | 81 | DOWN | 77 |
| hsa-miR-194 | Carcinoma | DOWN | 83 | DOWN | 86 |
| hsa-miR-29c | Carcinoma | DOWN | 82 | DOWN | 85 |
| hsa-miR-939 | Carcinoma | DOWN | 81 | DOWN | 76 |
| hsa-miR-181c | Carcinoma | UP | 84 | UP | 78 |
| hsa-miR-513c | Carcinoma | DOWN | 79 | DOWN | 74 |
| hsa-miR-572 | Carcinoma | DOWN | 84 | DOWN | 85 |
| hsa-miR-130b | Carcinoma | UP | 78 | UP | 83 |
| hsa-miR-30e | Carcinoma | DOWN | 78 | DOWN | 83 |
| hsa-miR-455-3p | Carcinoma | UP | 80 | UP | 83 |
| hsa-miR-192* | Carcinoma | DOWN | 81 | DOWN | 83 |
| hsa-miR-301a | Carcinoma | UP | 78 | UP | 76 |
| hsa-miR-452 | Carcinoma | UP | 78 | UP | 81 |
| hsa-miR-98 | Carcinoma | UP | 76 | UP | 77 |
| hsa-miR-486-5p | Carcinoma | DOWN | 73 | DOWN | 81 |
| hsa-miR-662 | Carcinoma | DOWN | 75 | DOWN | 74 |
| hsa-miR-19b | Carcinoma | UP | 74 | UP | 70 |
| hsa-miR-30e* | Carcinoma | DOWN | 75 | DOWN | 71 |
| hsa-miR-151-3p | Carcinoma | UP | 74 | UP | 87 |
| hsa-miR-29c* | Carcinoma | DOWN | 75 | DOWN | 77 |
| hsa-miR-623 | Carcinoma | DOWN | 73 | DOWN | 78 |
| hsa-miR-550* | Carcinoma | UP | 75 | UP | 74 |
| hsa-miR-134 | Carcinoma | DOWN | 70 | DOWN | 71 |
| hsa-miR-128 | Carcinoma | UP | 69 | UP | 67 |
| hsa-miR-21* | Carcinoma | UP | 71 | UP | 68 |

FIGURE 8

| NAME | PAM | GA | Naïve Bayesian | REGULATION |
|---|---|---|---|---|
| hsa-miR-139-5p | X | | X | DOWN |
| hsa-miR-497 | X | X | X | DOWN |
| hsa-miR-378* | X | | X | DOWN |
| hsa-miR-182 | X | | X | UP |
| hsa-miR-424 | X | | X | UP |
| hsa-miR-378 | X | | X | DOWN |
| hsa-miR-375 | X | | X | DOWN |
| hsa-miR-139-3p | | X | X | DOWN |

FIGURE 9

| NAME | PAM | GA | Naïve Bayesian | Regulation |
|---|---|---|---|---|
| hsa-miR-451 |  | X | X | DOWN |
| hsa-miR-99a | X |  | X | DOWN |
| hsa-miR-424 |  | X | X | UP |
| hsa-miR-375 |  | X | X | DOWN |

A

B

| CV Confusion Matrix (Threshold=4.4727) in the training dataset (n=122) | | | |
|---|---|---|---|
| True\Predicted | Adenoma-carcinoma | Normal-polyp | Class error rate |
| Adenoma-carcinoma | 68 | 4 | 0.06 |
| Normal-polyp | 3 | 47 | 0.06 |

C

| Prediction Confusion Matrix (Threshold=4.47269) in the testing dataset (n=103) | | | |
|---|---|---|---|
| True\Predicted | Adenoma-carcinoma | Normal-polyp | Prediction error rate |
| Adenoma-carcinoma | 57 | 4 | 0.07 |
| Normal-polyp | 1 | 41 | 0.02 |

A

B

| CV Confusion Matrix (Threshold=1.71449) in the training dataset (n=122) | | | |
|---|---|---|---|
| True\Predicted | Adenoma | Carcinoma | Class error rate |
| Adenoma | 14 | 1 | 0.07 |
| Carcinoma | 4 | 53 | 0.07 |

C

| Prediction Confusion Matrix (Threshold=1.714) in the testing dataset (n=103) | | | |
|---|---|---|---|
| True\Predicted | Adenoma | Carcinoma | Prediction error rate |
| Adenoma | 11 | 2 | 0.18 |
| Carcinoma | 2 | 46 | 0.04 |

COMPOSITIONS AND METHODS FOR
MICRO-RNA EXPRESSION PROFILING OF
COLORECTAL CANCER

FIELD OF THE INVENTION

The present invention relates to compositions and methods for microRNA expression profiling of colorectal cancer, particularly of adenocarcinoma.

BACKGROUND OF THE INVENTION

Most cancers are epithelial in origin and arise through a stepwise progression from normal cells, through dysplasia, into malignant cells that invade surrounding tissues and have metastatic potential. Colorectal cancer (CRC; also referred to as colon cancer or large bowel cancer) is one prominent type of cancer undergoing such tumor progression.

CRC includes cancerous growth in the colon, rectum and appendix. Colorectal cancer (CRC) is the most significant human cancer with an incidence of about 1.000.000 new cases worldwide in 2007. It is the third most common cancer and the fourth leading cause of cancer deaths in the world (reviewed, e.g., in Gryfe, R. et al. (1997) Curr. Probl. Cancer 21, 233-300; Petersen, G. M. et al. (1999) Cancer 86, 2540-2550). CRC is curable if diagnosed at an early stage of development. At this early stage, most patients have no phenotypic symptoms of the disease. Early detection can markedly improve chances of long-term survival.

Initially, CRC is characterized by the occurrence of a hyper-proliferative (dysplastic) epithelium in the colon, which first turns into inflammatory adenomatous polyps, then into adenomas, which are abnormal neoplasms (i.e. benign tumors) in the inner lining of the colon or rectum. Usually, only a small subset of the adenomas formed (occurring with an incidence of 60-70% by age 60) progress into malignant adenocarcinomas. More than 95% of the cases of CRC are manifested as adenocarcinomas (Muto, T. et al. (1975) Cancer 36, 2251-2270; Fearon, E. R. and Vogelstein, B. (1990) Cell 61, 759-767).

Molecular studies have shown that the etiology of colon carcinogenesis results from an accumulation of multiple epi-genetic and genetic alterations including inter alia activating mutations of the K-ras proto-oncogene, inactivating mutations of APC and p53 tumor suppressor genes and DNA repair genes (cf., e.g., Forrester, K. et al. (1987) Nature 327, 298-303; Baker, S. J. et al. (1989) Science 244, 217-221).

Genomic instability is another crucial step in progression from adenomas to adenocarcinomas and occurs in two ways in CRC (Lengauer, C. et al. (1997) Nature 386, 623-627). DNA mismatch repair deficiency leading to microsatellite instability, explains only about 15% of the cases of adenoma to carcinoma progression (Umar, A. et al. (2004) J. Natl. Cancer Inst. 96, 261-268; di Pietro, M. et al. (2005) Gastroenterology 129, 1047-1059). In the other 85%, genomic instability occurs at the chromosomal level (CIN), giving rise to aneuploidy. Chromosomal aberrations frequently reported in CRC are 7pq, 8q, 13q, and 20q gains and 4pq, 5q, 8p, 15q, 17p, and 18q losses (Douglas, E. J. et al. (2004) Cancer Res. 64, 4817-4825).

However, no specific molecular markers have been identified so far that allow for a reliable diagnosis of CRC, preferably CRC manifested as an adenocarcinoma, and/or the progression of a benign adenoma into such a malignant tumor, even though cDNA microarray analyses revealed a set of differentially expressed genes apparently involved in the development of CRC (Kitahara, O. et al. (2001) Cancer Res. 61, 3544-3549).

The identification of such molecular markers would be of utmost clinical importance, particularly if these markers enable a diagnosis at an early stage of tumor progression in order to allow early stage treatment of carcinomas while avoiding unnecessary surgical intervention. Ideally, such markers should enable the identification of a carcinoma at a stage where the presence of malignant cells is not yet detectable by in situ techniques or microscopic analysis of biopsy or resection material.

Many diagnostic assays are also hampered by the fact that they are typically based on the analysis of only a single molecular marker, which might affect detection reliability and/or accuracy. In addition, a single marker normally does not enable detailed predictions concerning latency stages, tumor progression, and the like. Thus, there is still a continuing need for the identification of alternative molecular markers and assay formats overcoming these limitations.

One approach to address this issue might be based on small regulatory RNA molecules, in particular on microRNAs (miRNAs) which, constitute an evolutionary conserved class of endogenously expressed small non-coding RNAs of 20-25 nucleotides (nt) in size that can mediate the expression of target mRNAs and thus—since their discovery about ten years ago—have been implicated with critical functions in cellular development, differentiation, proliferation, and apoptosis.

MiRNAS are produced from primary transcripts that are processed to stem-loop structured precursors (pre-miRNAs) by the RNase III Drosha. After transport to the cytoplasm, another RNase III termed Dicer cleaves of the loop of the pre-miRNA hairpin to form a short double-stranded (ds) RNA, one strand of which is incorporated as mature miRNA into a miRNA-protein (miRNP). The miRNA guides the miRNPs to their target mRNAs where they exert their function (reviewed, e.g. in Bartel, D. P. (2004) Cell 23, 281-292; He, L. and Hannon, G. J. (2004) Nat. Rev. Genet. 5, 522-531).

Depending on the degree of complementarity between the miRNA and its target, miRNAs can guide different regulatory processes. Target mRNAs that are highly complementary to miRNAs are specifically cleaved by mechanisms identical to RNA interference (RNAi). Thus, in such scenario, the miRNAs function as short interfering RNAs (siRNAs). Target mRNAs with less complementarity to miRNAs are either directed to cellular degradation pathways or are translationally repressed without affecting the mRNA level. However, the mechanism of how miRNAs repress translation of their target mRNAs is still a matter of controversy.

Emerging data available indicate that dysregulation of miRNA expression may inter alia be associated with the development and/or progression of certain types of cancer. For example, two miRNAs, miR-15 and miR-16-1, were shown to map to a genetic locus that is deleted in chronic lymphatic leukemia (CLL) and it was found that in about 70% of the CLL patients, both miRNA genes are deleted or down-regulated. Furthermore, down-regulation of miR-143 and miR-145 was observed in colorectal neoplasia, whereas expression of the miRNA let-7 is frequently reduced in lung cancers (Michael, M. Z. et al. (2003) Mol. Cancer. Res. 1, 882-891; Mayr, C. et al. (2007) Science 315, 1576-1579).

In fact, it has been speculated based on cancer-associated alterations in miRNA expression and the observation that miRNAs are frequently located at genomic regions involved in cancers that miRNAs may act both as tumor suppressors and as oncogenes (reviewed, e.g., in Esquela-Kerscher, A.

and Slack, F. J (2006) *Nat. Rev. Cancer* 6, 259-269; Calin, G. A. and Croce, C. M. (2007) *J. Clin. Invest.* 117, 2059-2066; Blenkiron, C. and Miska, E. A. (2007) *Hum. Mol. Genet.* 16, R106-R113).

More systematic bead-based flow cytometric miRNA expression analyses have revealed a global miRNAs regulation in tumors indicating that miRNA profiling of host cells might indeed be suitable for cancer diagnosis (cf., e.g., Lu J. et al. (2005) *Nature* 435, 834-838; Volinia, S. et al. (2006) *Proc. Natl. Acad. Sci. USA* 103, 2257-2261) and various miRNAs whose expression appears characteristic for a particular tumor have been identified (Calin, G. A. and Croce, C. M. (2007), supra). However, to date only few of these aberrantly expressed miRNAs have been directly linked with clinically relevant prognostic factors for tumor development and/or progression.

Thus, there still remains a need for (a set of) diagnostic markers, particularly in form of a "expression signature" or a "molecular footprint", that enable the rapid, reliable and cost-saving identification and/or treatment of cells exhibiting or having a predisposition to develop colorectal cancer. In addition, there is also a continuing need for corresponding methods both for the identification and for the treatment of target cells displaying such a cancerous phenotype.

OBJECT AND SUMMARY OF THE INVENTION

It is an objective of the present invention to provide novel approaches for diagnosing and/or treating colorectal cancer (CRC), particularly CRC manifested as an adenocarcinoma, and/or the predisposition for developing such a condition by determining a plurality of nucleic acid molecules, each nucleic acid molecule encoding a microRNA (miRNA) sequence, wherein one or more of the plurality of nucleic acid molecules are differentially expressed in the target cells analyzed as compared to healthy control cells, and wherein the one or more differentially expressed nucleic acid molecules together represent a nucleic acid expression signature that is indicative for the presence of or the predisposition to develop colorectal cancer.

More specifically, it is an object of the invention to provide compositions for diagnosing the progression from an adenoma to an adenocarcinoma, that is, for reliably discriminating between benign and malignant colorectal tumors.

Furthermore, it is an object of the invention to provide corresponding methods for identifying one or more mammalian target cells exhibiting or having a predisposition to develop colorectal cancer as well as for preventing or treating such a condition.

These objectives as well as others, which will become apparent from the ensuing description, are attained by the subject matter of the independent claims. Some of the preferred embodiments of the present invention are defined by the subject matter of the dependent claims.

In a first aspect, the present invention relates to a diagnostic kit of molecular markers for identifying one or more mammalian target cells exhibiting or having a predisposition to develop colorectal cancer, the kit comprising a plurality of nucleic acid molecules, each nucleic acid molecule encoding a microRNA sequence, wherein one or more of the plurality of nucleic acid molecules are differentially expressed in the target cells and in one or more control cells, and wherein the one or more differentially expressed nucleic acid molecules together represent a nucleic acid expression signature that is indicative for the presence of or the predisposition to develop colorectal cancer.

Preferably, the colorectal cancer is manifested as an adenocarcinoma.

In preferred embodiments of the invention, the diagnostic kit is for the further use of identifying a predepostion to develop colorectal adenoma or a predeposition to develop colorectal carcinoma or a predepostion to develop colorectal adenoma and carcinoma or identifying a progression of an adenoma to an adenocarcinoma or a predisposition for a progression of an adenoma to an adenocarcinoma.

In other specific embodiments, the nucleic acid expression signature comprises at least one nucleic acid molecule encoding a microRNA sequence whose expression is up-regulated in the one or more target cells compared to the one or more control cells and at least one nucleic acid molecule encoding a microRNA sequence whose expression is down-regulated in the one or more target cells compared to the one or more control cells.

The nucleic acid expression signature, as defined herein, may comprise at least three nucleic acid molecules, preferably at least five nucleic acid molecules, and particularly preferably at least ten nucleic acid molecules.

Preferably, the nucleic acid expression signature comprises nucleic acid molecules encoding hsa-miR-224, hsa-miR-183, and hsa-miR-18b. More preferably, the nucleic acid expression signature further comprises nucleic acid molecules encoding hsa-miR-96, hsa-miR-182, and hsa-miR-106a.

In particularly preferred embodiments, the nucleic acid expression signature comprises nucleic acid molecules encoding hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, and hsa-miR-30a.

In specific embodiments, the nucleic acid expression signature comprises nucleic acid molecules encoding hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, and hsa-miR-30a, and further comprises nucleic acid molecules encoding hsa-miR-135b, hsa-miR-93, hsa-miR-17, hsa-miR-20b, and hsa-miR-24.

In further particularly preferred embodiments, the expression of the nucleic acid molecules encoding hsa-miR-224, hsa-miR-96, hsa-miR-21, hsa-miR-182, hsa-miR-183, hsa-miR-221, hsa-miR-106b, hsa-miR-106a, hsa-miR-18b, hsa-miR-135b, hsa-miR-93, hsa-miR-17, hsa-miR-20b, and hsa-miR-24 is up-regulated and the expression of the nucleic acid molecules hsa-miR-497 and hsa-miR-30a is down-regulated in the in the one or more target cells compared to the one or more control cells.

The nucleic acid expression signature for the use of identifying a predepostion to develop colorectal adenoma, as further defined herein may comprise at least four nucleic acid molecules, preferably at least two four nucleic acid molecules.

The nucleic acid expression signature for the use of identifying a predeposition to develop colorectal carcinoma, as further defined herein may comprise at least thirty-two nucleic acid molecules, preferably at least twelve nucleic acid molecules, and particularly preferably at least six nucleic acid molecules.

The nucleic acid expression signature for the use of identifying a predepostion to develop colorectal adenoma and carcinoma, as further defined herein may comprise at least fourteen nucleic acid molecules, preferably at least eight nucleic acid molecules, and particularly preferably at least four nucleic acid molecules.

In further preferred embodiments of the invention, the nucleic acid expression signature of the diagnostic kit for exhibiting or having a predisposition to develop colorectal adenoma comprises any one or more human target cell-derived nucleic acid molecules encoding microRNA sequences selected from the group consisting of hsa-miR-376a, hsa-miR-429, hsa-miR-451 and hsa-miR-99a.

Preferably, the nucleic acid expression signature of the diagnostic kit for exhibiting or having a predisposition to develop colorectal adenoma comprises any one or more human target cell-derived nucleic acid molecules encoding microRNA sequences selected from the group consisting of hsa-miR-376a and hsa-miR-99a.

Particularly preferably, the expression of any one or more of the nucleic acid molecules encoding hsa-miR-429 is up-regulated and the expression of any one or more of the nucleic acid molecules hsa-miR-376a, hsa-miR-451, and hsa-miR-99a is down-regulated in the in the one or more target cells compared to the one or more control cells.

In further embodiments of the invention, the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p, hsa-miR-497, hsa-miR-378*, hsa-miR-182, hsa-miR-20b, hsa-miR-17*, hsa-miR-376c, hsa-miR-20a*, hsa-miR-638, hsa-miR-335*, hsa-miR-342-5p, hsa-miR-34b*, hsa-miR-145* and hsa-miR-552.

Preferably, the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p, hsa-miR-497, hsa-miR-378*, hsa-miR-182, hsa-miR-20b, hsa-miR-17*, hsa-miR-376c, hsa-miR-20a*.

More preferably, the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p, hsa-miR-497, hsa-miR-378*, hsa-miR-182.

Particularly preferably, the expression of any one or more of the nucleic acid molecules encoding hsa-miR-182, hsa-miR-20b, hsa-miR-17*, hsa-miR-20a*, hsa-miR-335*, hsa-miR-34b*, and hsa-miR-552 is up-regulated and the expression of any one or more of the nucleic acid molecules hsa-miR-139-5p, hsa-miR-497, hsa-miR-378*, hsa-miR-376c, hsa-miR-638, hsa-miR-342-5p, and hsa-miR-145* is down-regulated in the in the one or more target cells compared to the one or more control cells.

In other embodiments of the invention, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424, hsa-miR-378, hsa-miR-375, hsa-miR-139-3p, hsa-miR-18b, hsa-miR-18a, hsa-miR-650, hsa-miR-194*, hsa-miR-194, hsa-miR-29c, hsa-miR-939, hsa-miR-181c, hsa-miR-513c, hsa-miR-572, hsa-miR-130b, hsa-miR-30e, hsa-miR-455-3p, hsa-miR-192*, hsa-miR-301a, hsa-miR-452, hsa-miR-98, hsa-miR-486-5p, hsa-miR-662, hsa-miR-19b, hsa-miR-30e*, hsa-miR-151-3p, hsa-miR-29c*, hsa-miR-623, hsa-miR-550*, hsa-miR-134, hsa-miR-128, and hsa-miR-21*.

Preferably, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424, hsa-miR-378, hsa-miR-375, hsa-miR-139-3p, hsa-miR-18b, hsa-miR-18a, hsa-miR-650, hsa-miR-194*, hsa-miR-194, hsa-miR-29c, hsa-miR-939, hsa-miR-181c.

More preferably, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424, hsa-miR-378, hsa-miR-375, hsa-miR-139-3p, hsa-miR-18b, hsa-miR-18a.

Particularly preferably, the expression of any one or more of the nucleic acid molecules encoding hsa-miR-424, hsa-miR-18b, hsa-miR-18a, hsa-miR-181c, hsa-miR-130b, hsa-miR-455-3p, hsa-miR-301a, hsa-miR-452, hsa-miR-98, hsa-miR-19b; hsa-miR-151-3p, hsa-miR-550*, hsa-miR-128, and hsa-miR-21* is up-regulated and the expression of any one or more of the nucleic acid molecules hsa-miR-378, hsa-miR-375, hsa-miR-139-3p, hsa-miR-650, hsa-miR-194*, hsa-miR-194, hsa-miR-29c, hsa-miR-939, hsa-miR-513c, hsa-miR-572, hsa-miR-30e, hsa-miR-192*, hsa-miR-486-5p, hsa-miR-662, hsa-miR-30e*, hsa-miR-29c*, hsa-miR-623, and hsa-miR-134 is down-regulated in the in the one or more target cells compared to the one or more control cells.

In a second aspect, the present invention relates to a method for identifying one or more mammalian target cells exhibiting or having a predisposition to develop colorectal cancer, the method comprising: (a) determining in the one or more target cells the expression levels of a plurality of nucleic acid molecules, each nucleic acid molecule encoding a microRNA sequence; (b) determining the expression levels of the plurality of nucleic acid molecules in one or more control cells; and (c) identifying from the plurality of nucleic acid molecules one or more nucleic acid molecules that are differentially expressed in the target and control cells by comparing the respective expression levels obtained in steps (a) and (b), wherein the one or more differentially expressed nucleic acid molecules together represent a nucleic acid expression signature, as defined herein, that is indicative for the presence of or the predisposition to develop colorectal cancer.

Preferably, the colorectal cancer is manifested as an adenocarcinoma.

In preferred embodiments of the invention, the method is for the further use of identifying a predepostion to develop colorectal adenoma or a predeposition to develop colorectal carcinoma or a predepostion to develop colorectal adenoma and carcinoma or identifying a progression of an adenoma to an adenocarcinoma or a predisposition for a progression of an adenoma to an adenocarcinoma.

In a third aspect, the present invention relates to a method for preventing or treating colorectal cancer in one or more mammalian target cells, the method comprising: (a) identifying in one or more target cells a nucleic acid expression signature by using a method, as defined herein; and (b) modifying in the one or more cells the expression of one or more nucleic acid molecules encoding a microRNA sequence that is/are comprised in the nucleic acid expression signature in such way that the expression of a nucleic acid molecule whose expression is up-regulated in the one or more target cells is down-regulated and the expression of a nucleic acid molecule whose expression is down-regulated in the one or more target cells is up-regulated.

Preferably, the colorectal cancer is manifested as an adenocarcinoma.

In a forth aspect, the present invention relates to a pharmaceutical composition for the prevention and/or treatment of colorectal cancer, preferably manifested as an adenocarcinoma, in one or more mammalian target cells, the composition comprising one or more nucleic acid molecules, each nucleic acid molecule encoding a sequence that is at least partially complementary to a microRNA sequence encoded by a nucleic acid molecule whose expression is up-regulated in the one or more target cells, as defined herein, and/or that corresponds to a microRNA sequence encoded by a nucleic acid molecule whose expression is down-regulated in the one or more target cells, as defined herein.

Finally, in a fifth aspect, the present invention relates to the use of said pharmaceutical composition for the manufacture of a medicament for the prevention and/or treatment of colorectal cancer, preferably manifested as an adenocarcinoma.

Other embodiments of the present invention will become apparent from the detailed description hereinafter.

BRIEF DESCRIPTION OF THE DRAWINGS

FIG. 1 illustrates the nucleic acid sequences of 16 human miRNAs (hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, hsa-miR-30a, hsa-miR-135b, hsa-miR-93, hsa-miR-17, hsa-miR-20b, and hsa-miR-24) comprised in particularly preferred expression signatures according to the present invention for identifying one or more target cells exhibiting or having a predisposition to develop colorectal cancer, preferably for diagnosing an adenocarcinoma and/or the progression of an adenoma to an adenocarcinoma.

FIG. 5 illustrates the further identified human miRNAs in colorectal tumor comprised in particularly preferred expression signatures according to the present invention for identifying one or more target cells exhibiting or having a predisposition to develop colorectal cancer. Also indicated the expression levels (regulation) and accuracy of these miRNAs in tumor tissue as compared to control tissue (colorectal normal and inflammatory polyp) as an up-regulation or a down-regulation.

FIG. 8 depicts 8 identified miRNAs that were predicted by any two of the employed three classification algorithms for discriminating adenoma/carcinoma from normal/inflammatory polyp tissue in the colorectal biopsies and surgical colon specimens. Potential clinical values are: 1) pre-cancer (adenoma) detection, 2) early cancer (carcinoma) detection, 3) CRC risk assessment in patients with adenomas. Additionally, they are potential targets for drug development at the pre-cancer and early stages of CRC.

FIG. 9 depicts 4 identified miRNAs that were predicted by any two of the employed three classification algorithms for discriminating adenoma from carcinoma in the colorectal biopsies and surgical colon specimens. Potential clinical values are: 1) pre-cancer (adenoma) detection, 2) early cancer (carcinoma) detection and 3) differential carcinoma diagnosis. Additionally, they are potential targets for drug development at the pre-cancer and early stages of CRC.

DETAILED DESCRIPTION OF THE INVENTION

Figure 2:
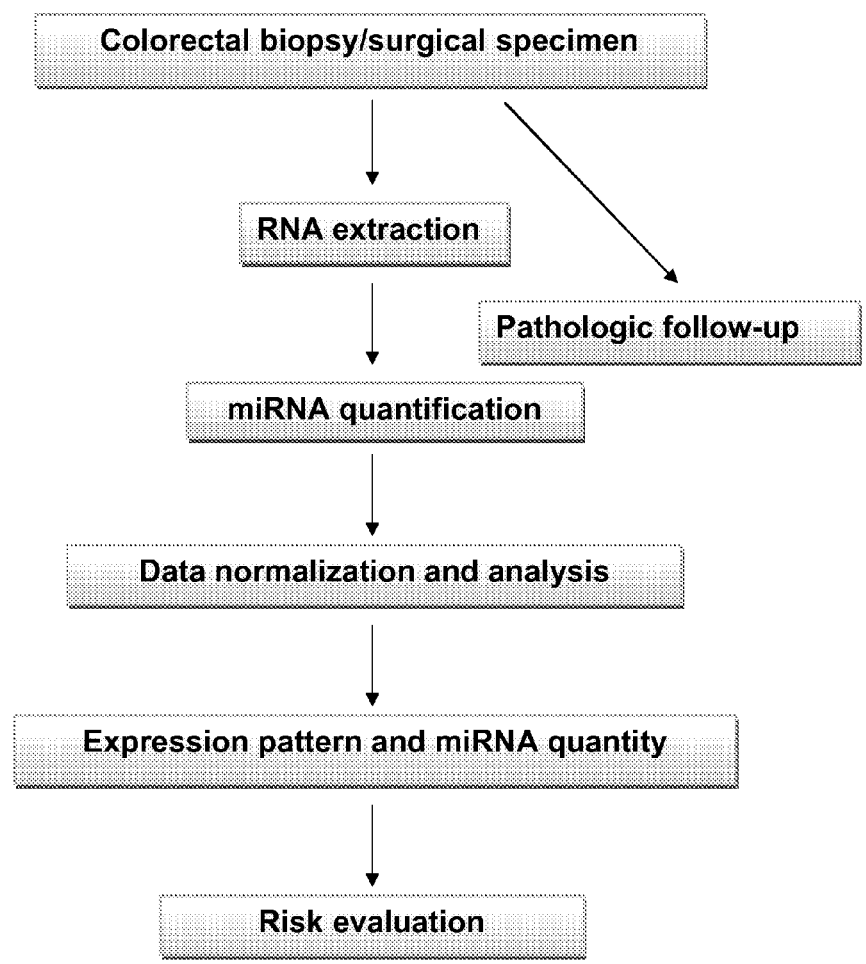
FIG. 2 depicts a flow chart schematically illustrating the essential method steps for determining an expression signature according to the present invention for identifying one or more target cells exhibiting or having a predisposition to develop colorectal cancer, preferably for diagnosing an adenocarcinoma.

The present invention is based on the unexpected finding that cells exhibiting or having a predisposition to develop colorectal cancer, preferably an adenocarcinoma can be reliably identified based on a particular miRNA expression signature both with high accuracy and sensitivity, wherein the expression signature as defined herein typically comprises both up- and down-regulated human miRNAs. More specifically, said miRNA expression signature—by analyzing the overall miRNA expression pattern and/or the respective individual miRNA expression level(s)—allows an evaluation of the risk that a benign adenoma transforms into a malignant adenocarcinoma, and thus the detection of colorectal cancer at an early disease state.

The present invention illustratively described in the following may suitably be practiced in the absence of any element or elements, limitation or limitations, not specifically disclosed herein. The present invention will be described with respect to particular embodiments and with reference to certain drawings but the invention is not limited thereto but only by the claims. The drawings described are only schematic and are to be considered non-limiting.

Where the term "comprising" is used in the present description and claims, it does not exclude other elements or steps. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun e.g. "a" or "an", "the", this includes a plural of that noun unless specifically stated otherwise.

The term "about" in the context of the present invention denotes an interval of accuracy that the person skilled in the art will understand to still ensure the technical effect of the feature in question. The term typically indicates deviation from the indicated numerical value of ±10%, and preferably ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used.

The following terms or definitions are provided solely to aid in the understanding of the invention. These definitions should not be construed to have a scope less than understood by a person of ordinary skill in the art.

In a first aspect, the present invention relates to a diagnostic kit of molecular markers for identifying one or more mammalian target cells exhibiting or having a predisposition to develop colorectal cancer, the kit comprising a plurality of nucleic acid molecules, each nucleic acid molecule encoding a microRNA sequence, wherein one or more of the plurality of nucleic acid molecules are differentially expressed in the target cells and in one or more control cells, and wherein the one or more differentially expressed nucleic acid molecules together represent a nucleic acid expression signature that is indicative for the presence of or the predisposition to develop colorectal cancer.

Preferably, the colorectal cancer is manifested as an adenocarcinoma.

In preferred embodiments of the invention, the diagnostic kit is for the further use of identifying a predepostion to develop colorectal adenoma or a predeposition to develop colorectal carcinoma or a predeposition to develop colorectal adenoma and carcinoma or identifying a progression of an adenoma to an adenocarcinoma or a predisposition for a progression of an adenoma to an adenocarcinoma.

The term "colorectal", as used herein, relates to the colon, the rectum and/or the appendix, i.e. the complete large intestine.

The term "cancer" (also referred to as "carcinoma"), as used herein, generally denotes any type of malignant neoplasm, that is, any morphological and/or physiological alterations (based on genetic re-programming) of target cells exhibiting or having a predisposition to develop characteristics of a carcinoma as compared to unaffected (healthy) wild-type control cells. Examples of such alterations may relate inter alia to cell size and shape (enlargement or reduction), cell proliferation (increase in cell number), cell differentiation (change in physiological state), apoptosis (programmed cell death) or cell survival. Hence, the term "colorectal cancer" refers to cancerous growths in the colon, rectum, and appendix.

The term "having a predisposition to develop cancer", as used herein, denotes any cellular phenotype being indicative for a pre-cancerous state, i.e. an intermediate state in the transformation of a normal cell into a tumor cell. In other words, the term denotes a state of risk of developing cancer.

The most common colorectal cancer (CRC) cell type is adenocarcinoma that accounts for about 95% of cases. Other types of CRC include inter alia lymphoma and squamous cell carcinoma.

The term "adenocarcinoma", as used herein, relates to a malignant neoplasm of epithelial cells of the colorectal mucosa. Typically, adenocarcinoma is a type of cancer that originates in glandular tissue. This tissue is part of a more general type of tissue known as epithelial tissue. Epithelial tissue includes skin, glands and a variety of other tissues lining/surrounding the cavities and organs of the body.

Embryologically, the epithelium is derived from ectoderm, endoderm and mesoderm. In order to be classified as adenocarcinoma, the cells do not necessarily need to be part of a gland, as long as they have secretory properties. Hence, adenocarcinomas are also often referred to as "glandular cancer" or "glandular carcinoma". Highly differentiated adenocarcinomas tend to resemble the glandular tissue that they are derived from, while poorly differentiated may not.

The occurrence of a hyper-proliferative epithelium in the colon is the first step in cancer progression. This dysplastic epithelium turns into inflammatory adenomatous polyps, subsequently into adenomas, which are abnormal but benign neoplasms (i.e. tumors) in the inner lining of the colon or rectum. Thus, the term "adenoma", as used herein, thus relates to a benign epithelial neoplasm. Adenomas are usually well circumscribed and can be flat or polypoid. The neoplastic cells of benign adenomas do not infiltrate or invade adjacent tissue and rarely metastasize. The term "adenoma" is understood as equivalent to "non-progressed adenoma". Malignant adeno-carcinomas, however, invade other tissues and often metastasize given enough time to do so. Malignant cells are often characterized by progressive and uncontrolled growth. They can spread locally or through the blood stream and lymphatic system to other parts of the body. Particularly, hepatic metastases (i.e. metastases in the liver) are commonly found to be associated with adenocarcinomas. The occurrence of such metastases may be considered a late stage (or even a post-cancerous stage) of colorectal cancer.

The terms "progressed adenoma", as used herein, refer to an adenoma that harbors a focus of a cancer. This is also called a "malignant polyp". Colorectal adenomas are common in the elderly population, but only a small proportion of these pre-malignant tumors (estimated approximately 5%) progresses to malignant tumors. Such malignant tumors are herein referred to as (colorectal) "adenocarcinomas".

Adenocarcinomas may be classified according to the Dukes system (Dukes, C. E. (1932) *J. Pathol. Bacteriol.* 35, 323-325), which identifies the following stages: Dukes A—a tumour confined to the intestinal wall; Dukes B—a tumor invading through the intestinal wall; Dukes C—a tumor also involving the lymph node(s); and Dukes D—a tumor with distant metastasis.

The present invention further relates to the identification of specific adenocarcinoma-associated disease states, i.e. disease states that are (closely) related but not identical to adenocarcinoma. The term "adenocarcinoma-associated disease states", as used herein, thus relates particularly to a predisposition to develop an adenocarcinoma, a progression of an adenoma to an adenocarcinoma and a predisposition for a progression of an adenoma to an adenocarcinoma.

The term "predisposition to develop an adenocarcinoma" in the context of the present invention denotes a state of risk of developing an adenocarcinoma, for example, a state of having an adenoma. Preferably, a predisposition for developing an adenocarcinoma may be present in cases (i.e. one or more target cells analyzed) in which the extent (level) of differential expression of the nucleic acid molecules comprised in the nucleic acid expression signature, as defined herein, is reduced as compared to the extent determined in one or more target cells evidently exhibiting an adenocarcinoma. The term "reduced" in this context, relates to a level of differential gene expression, which is reduced by about 40% to about 90%, preferably by about 45% to about 75%, and particularly preferably by about 50% to about 60% as compared to the level determined in one or more target cells evidently exhibiting an adenocarcinoma. Such a reduction in the level of differential gene expression is indicative for a predisposition to develop an adenocarcinoma.

The term "progression of an adenoma to an adenocarcinoma", as used herein, relates to a (disease) state in which the extent (level) of differential expression of the nucleic acid molecules comprised in the nucleic acid expression signature, as defined herein, is increased as compared to the extent determined in one or more target cells evidently exhibiting an adenoma. The term relates to cases in which the level of gene expression is elevated by about 5% to about 50%, preferably by about 10% to about 40%, and particularly preferably by about 20% to about 30% as compared to the level determined in one or more target cells evidently exhibiting an adenoma. Such an increase in the level of differential gene expression is indicative for a progression of an adenoma to an adenocarcinoma.

The term "predisposition for a progression of an adenoma to an adenocarcinoma", as used herein, relates to a similar (disease) state as the progression of an adenoma to an adenocarcinoma. However, the extent (level) of differential expression of the nucleic acid molecules comprised in the nucleic acid expression signature, as defined herein, is elevated by about 1% to about 15%, preferably by about 3% to about 12%, and particularly preferably by about 5% to about 10% as compared to the level determined in one or more target cells evidently exhibiting an adenoma. Such an increase in the level of differential gene expression is indicative for a predisposition for a progression of an adenoma to an adenocarcinoma.

The mammalian target cells employed in the present invention may be of human or non-human origin. However, the invention is typically performed with human cells. The term "one or more cells", as used herein, is to be understood not only to include individual cells but also tissues, organs, and organisms. The term "target cell", as used herein, refers to a cell being at least supposed to exhibit or to have a predisposition to develop colorectal cancer, whereas the term "control cell" typically denotes a (healthy) wild-type cell not having characteristics of such a cancerous phenotype. However, in some applications, for example, when comparing cells exhibiting different cancerous or pre-cancerous states, the cells having the less severe disease characteristics are typically considered the "control cells".

Typically, the target and control cells used are derived from biological samples collected from the subjects to be diagnosed for the presence or the predisposition to develop colorectal cancer. Furthermore, in order to corroborate the data obtained "comparative samples" may also be collected from subjects having a given known disease state. The biological samples may include body tissues and fluids, such as blood, sputum, and urine. Furthermore, the biological sample may contain a cell extract derived from or a cell population including an epithelial cell, preferably a cancerous epithelial cell or an epithelial cell derived from tissue suspected to be cancerous. Even more preferably the biological sample comprises a cell population derived from a glandular tissue. Furthermore, the cell may be purified from the obtained body tissues and fluids if necessary, and then used as the biological sample. According to the present invention, the expression level of the nucleic acid markers of the present invention is determined in the subject-derived biological sample(s).

The sample used for detection in the in vitro methods of the present invention should generally be collected in a clinically acceptable manner, preferably in a way that nucleic acids (in particular RNA) or proteins are preserved. The samples to be analyzed are typically colorectal biopsies or resections. Intact cells or a cell lysate from tumor tissue may also detach from the colon without intervention and will end up in the feces. Accordingly, stool samples are also considered as a suitable source for isolating RNA. Furthermore, colorectal adenocarcinoma cells may migrate into other tissues. Hence, blood and other types of sample can be used as well. A biopsy or resection may contain a majority of adenoma cells and only a minority of adenocarcinoma cells. To increase the signal/background ratio, a resection can be divided into different sub-samples prior to analysis (for example, by laser-capture microdissection). Even if the total number of carcinoma cells in the biopsy or resection is limited, at least one of the sub-samples may contain an increased ratio of adenocarcinoma versus adenoma cells. Samples, in particular after initial processing may be pooled. However, also non-pooled samples may be used.

The term "microRNA" (or "miRNA"), as used herein, is given its ordinary meaning in the art (reviewed, e.g. in Bartel, D. P. (2004) *Cell* 23, 281-292; He, L. and Hannon, G. J. (2004) *Nat. Rev. Genet.* 5, 522-531). Accordingly, a "microRNA" denotes a RNA molecule derived from a genomic locus that is processed from transcripts that can form local RNA precursor miRNA structures. The mature miRNA is usually 20, 21, 22, 23, 24, or 25 nucleotides in length, although other numbers of nucleotides may be present as well, for example 18, 19, 26 or 27 nucleotides.

The miRNA encoding sequence has the potential to pair with flanking genomic sequences, placing the mature miRNA within an imperfect RNA duplex (herein also referred to as stem-loop or hairpin structure or as pre-miRNA), which serves as an intermediate for miRNA processing from a longer precursor transcript. This processing typically occurs through the consecutive action of two specific endonucleases termed Drosha and Dicer, respectively. Drosha generates from the primary transcript (herein also denoted "pri-miRNA") a miRNA precursor (herein also denoted "pre-miRNA") that typically folds into a hairpin or stem-loop structure. From this miRNA precursor a miRNA duplex is excised by means of Dicer that comprises the mature miRNA at one arm of the hairpin or stem-loop structure and a similar-sized segment (commonly referred to miRNA*) at the other arm. The miRNA is then guided to its target mRNA to exert its function, whereas the miRNA* is degraded. In addition, miRNAs are typically derived from a segment of the genome that is distinct from predicted protein-coding regions.

The term "miRNA precursor" (or "precursor miRNA" or "pre-miRNA"), as used herein, refers to the portion of a miRNA primary transcript from which the mature miRNA is processed. Typically, the pre-miRNA folds into a stable hairpin (i.e. a duplex) or a stem-loop structure. The hairpin structures typically range from 50 to 80 nucleotides in length, preferably from 60 to 70 nucleotides (counting the miRNA residues, those pairing to the miRNA, and any intervening segment(s) but excluding more distal sequences).

The term "nucleic acid molecule encoding a microRNA sequence", as used herein, denotes any nucleic acid molecule coding for a microRNA (miRNA). Thus, the term does not only refer to mature miRNAs but also to the respective precursor miRNAs and primary miRNA transcripts as defined above. Furthermore, the present invention is not restricted to RNA molecules but also includes corresponding DNA molecules encoding a microRNA, e.g. DNA molecules generated by reverse transcribing a miRNA sequence. A nucleic acid molecule encoding a microRNA sequence according to the invention typically encodes a single miRNA sequence (i.e. an individual miRNA). However, it is also possible that such nucleic acid molecule encodes two or more miRNA sequences (i.e. two or more miRNAs), for example a transcriptional unit comprising two or more miRNA sequences under the control of common regulatory sequences such as a promoter or a transcriptional terminator.

The term "nucleic acid molecule encoding a microRNA sequence", as used herein, is also to be understood to include "sense nucleic acid molecules" (i.e. molecules whose nucleic acid sequence (5'→3') matches or corresponds to the encoded miRNA (5'→3') sequence) and "anti-sense nucleic acid molecules" (i.e. molecules whose nucleic acid sequence is complementary to the encoded miRNA (5'→3') sequence or, in other words, matches the reverse complement (3'→5') of the encoded miRNA sequence). The term "complementary", as used herein, refers to the capability of an "anti-sense" nucleic acid molecule sequence of forming base pairs, preferably Watson-Crick base pairs, with the corresponding "sense" nucleic acid molecule sequence (having a sequence complementary to the anti-sense sequence).

Within the scope of the present invention, two nucleic acid molecules (i.e. the "sense" and the "anti-sense" molecule) may be perfectly complementary, that is, they do not contain any base mismatches and/or additional or missing nucleotides. Alternatively, the two molecules comprise one or more base mismatches or differ in their total numbers of nucleotides (due to additions or deletions). Preferably, the "complementary" nucleic acid molecule comprises at least ten contiguous nucleotides showing perfect complementarity with a sequence comprised in corresponding "sense" nucleic acid molecule.

Accordingly, the plurality of nucleic acid molecules encoding a miRNA sequence that are comprised in a diagnostic kit of the present invention may include one or more "sense nucleic acid molecules" and/or one or more "anti-sense nucleic acid molecules". In case, the diagnostic kit includes one or more "sense nucleic acid molecules" (i.e. the miRNA sequences as such), said molecules are to be considered to constitute the totality or at least a subset of differentially expressed miRNAs (i.e. molecular markers) being indicative for the presence of or the disposition to develop a particular condition, here colorectal cancer, preferably colorectal cancer manifested as an adenocarcinoma. On the other hand, in case a diagnostic kit includes one or more "anti-sense nucleic acid molecules" (i.e. sequences complementary to the miRNA sequences), said molecules may comprise inter alia probe molecules (for performing hybridization assays) and/or oligonucleotide primers (e.g., for reverse transcription or PCR applications) that are suitable for detecting and/or quantifying one or more particular (complementary) miRNA sequences in a given sample.

A plurality of nucleic acid molecules as defined within the present invention may comprise at least two, at least ten, at least 50, at least 100, at least 200, at least 500, at least 1.000, at least 10.000 or at least 100.000 nucleic acid molecules, each molecule encoding a miRNA sequence.

The term "differentially expressed", as used herein, denotes an altered expression level of a particular miRNA in the target cells as compared to the healthy control cells, which may be an up-regulation (i.e. an increased miRNA concentration in the target cells) or a down-regulation (i.e. a reduced or abolished miRNA concentration in the target cells). In other words, the nucleic acid molecule is activated to a higher or lower level in the target cells than in the control cells.

Within the scope of the present invention, a nucleic acid molecule is to considered differentially expressed if the respective expression levels of this nucleic acid molecule in target cells and control cells typically differ by at least 5% or at least 10%, preferably by at least 20% or at least 25%, and most preferably by at least 30% or at least 50%. Thus, the latter values correspond to an at least 1.3-fold or at least 1.5-fold up-regulation of the expression level of a given nucleic acid molecule in the target cells compared to the wild-type control cells or vice versa an at least 0.7-fold or at least 0.5-fold down-regulation of the expression level in the target cells, respectively.

The term "expression level", as used herein, refers to extent to which a particular miRNA sequence is transcribed from its genomic locus, that is, the concentration of a miRNA in the one or more cells to be analyzed.

As outlined above, the term "control cell" typically denotes a (healthy) wild-type cell not having characteristics of a CRC phenotype. However, in some applications, for example, when comparing cells exhibiting different cancerous or pre-cancerous states, the cells having the less severe disease characteristics are typically considered the "control cells".

The determining of expression levels typically follows established standard procedures well known in the art (cf., for example, Sambrook, J. et al. (1989) *Molecular Cloning: A Laboratory Manual.* 2nd Ed., Cold Spring Harbor Laboratory Press, Cold Spring Harbor, N.Y.; Ausubel, F. M. et al. (2001) *Current Protocols in Molecular Biology.* Wiley & Sons, Hoboken, N.J.). Determination may occur at the RNA level, for example by Northern blot analysis using miRNA-specific probes, or at the DNA level following reverse transcription (and cloning) of the RNA population, for example by quantitative PCR or real-time PCR techniques. The term "determining", as used herein, includes the analysis of any nucleic acid molecules encoding a microRNA sequence as described above. However, due to the short half-life of pri-miRNAs and pre-mRNAs typically the concentration of only the mature miRNA is measured.

In specific embodiments, the standard value of the expression levels obtained in several independent measurements of a given sample (for example, two, three, five or ten measurements) and/or several measurements within a population of target cells or control cells is used for analysis. The standard value may be obtained by any method known in the art. For example, a range of mean±2 SD (standard deviation) or mean±3 SD may be used as standard value.

The difference between the expression levels obtained for one or more target cells and one or more control cells may be normalized to the expression level of further control nucleic acids, e.g. housekeeping genes whose expression levels are known not to differ depending on the disease states of the cell. Exemplary housekeeping genes include inter alia β-actin, glycerinaldehyde 3-phosphate dehydrogenase, and ribosomal protein P1.

In preferred embodiments, the control nucleic acid for normalizing the expression levels obtained is another miRNA known to be stably expressed during the various non-cancerous and (pre-)cancerous states of the cell.

However, instead of determining in any experiment the expression levels for one or more control cells it may also be possible to define based on experimental evidence and/or prior art data on or more cut-off values for a particular cell phenotype (i.e. a disease state). In such scenario, the respective expression levels for the one or more target cells can be determined by using a stably expressed control miRNA for normalization. If the "normalized" expression levels calculated are higher than the respective cutoff value defined, then this finding would be indicative for an up-regulation of gene expression. Vice versa, if the "normalized" expression levels calculated are lower than the respective cutoff value defined, then this finding would be indicative for a down-regulation of gene expression.

In the context of the present invention, the term "identifying one or more mammalian target cells exhibiting or having a predisposition to develop colorectal cancer" is intended to also encompass predictions and likelihood analysis (in the sense of "diagnosing"). The compositions and methods disclosed herein are intended to be used clinically in making decisions concerning treatment modalities, including therapeutic intervention, diagnostic criteria such as disease stages, and disease monitoring and surveillance for the disease. According to the present invention, an intermediate result for examining the condition of a subject may be provided. Such intermediate result may be combined with additional information to assist a doctor, nurse, or other practitioner to diagnose that a subject suffers from the disease. Alternatively, the present invention may be used to detect cancerous cells in a subject-derived tissue, and provide a doctor with useful information to diagnose that the subject suffers from the disease.

Within the present invention, one or more differentially expressed nucleic acid molecules identified together represent a nucleic acid expression signature that is indicative for the presence of or the predisposition to develop colorectal cancer in the target cells. The term "expression signature", as used herein, denotes a set of nucleic acid molecules (e.g., miRNAs), wherein the expression level of the individual nucleic acid molecules differs between the (cancerous) target cells and the (non-cancerous) control cells. Herein, a nucleic acid expression signature is also referred to as a set of markers and represents a minimum number of (different) nucleic acid molecules, each encoding a miRNA sequence that is capable for identifying a phenotypic state of a target cell.

In specific embodiments, the nucleic acid expression signature comprises at least three nucleic acid molecules, each encoding a (different) miRNA sequence. Preferably, the nucleic acid expression signature comprises at least five or at least eight (different) nucleic acid molecules. Particularly preferably, the nucleic acid signature comprises at least ten or at least twelve (different) nucleic acid molecules.

In other specific embodiments, the nucleic acid expression signature e.g. for the use of identifying a predepostion to develop colorectal adenoma, as further defined herein may comprise at least two (different) nucleic acid molecules, preferably at least four (different) nucleic acid molecules.

In further specific embodiments, the nucleic acid expression signature e.g. for the use of identifying a predeposition to develop colorectal carcinoma, as further defined herein may comprise at least six (different) nucleic acid molecules, preferably at least twelve (different) nucleic acid molecules, and particularly preferably at least thirty-two (different) nucleic acid molecules.

In other specific embodiments, the nucleic acid expression signature e.g. for the use of identifying a predepostion to develop colorectal adenoma and carcinoma, as further defined herein may comprise at least four (different) nucleic acid molecules, preferably at least eight (different) nucleic acid molecules, and particularly preferably at least fourteen (different) nucleic acid molecules.

Typically, the nucleic acid molecules comprised in the nucleic acid expression signature are human sequences (hereinafter designated "hsa" (*Homo sapiens*)).

In further preferred embodiments, the nucleic acid expression signature comprises at least one nucleic acid molecule encoding a miRNA sequence whose expression is up-regulated (i.e. its concentration is increased) in the one or more target cells compared to the one or more control cells and at least one nucleic acid molecule encoding a miRNA sequence whose expression is down-regulated (i.e. its concentration is reduced) in the one or more target cells compared to the one or more control cells.

In preferred embodiments of the invention, the nucleic acid expression signature of the diagnostic kit comprises any one or more human target cell-derived nucleic acid molecules encoding microRNA sequences selected from the group consisting of hsa-miR-224 (SEQ ID NO:1), hsa-miR-96 (SEQ ID NO:2), hsa-miR-21 (SEQ ID NO:3), hsa-miR-182 (SEQ ID NO:4), hsa-miR-183 (SEQ ID NO:5), hsa-miR-221 (SEQ ID NO:6), hsa-miR-497 (SEQ ID NO:7), hsa-miR-106b (SEQ ID NO:8), hsa-miR-106a (SEQ ID NO:9), hsa-miR-18b (SEQ ID NO:10), hsa-miR-30a (SEQ ID NO:11) hsa-miR-135b (SEQ ID NO:12), hsa-miR-93 (SEQ ID NO:13), hsa-miR-17 (SEQ ID NO:14), hsa-miR-20b (SEQ ID NO:15), and hsa-miR-24 (SEQ ID NO:16) (cf. FIG. 1).

The nucleic acid sequences of the above-referenced miRNAs are listed in Table 1.

TABLE 1

| miRNA | Sequence (5'→3') | |
|---|---|---|
| hsa-miR-224 | caagucacuag ugguuccguu | (SEQ ID NO: 1) |
| hsa-miR-96 | uuuggcacuagc acauuuuugcu | (SEQ ID NO: 2) |
| hsa-miR-21 | uagcuuaucaga cugauguuga | (SEQ ID NO: 3) |
| hsa-miR-182 | uuuggcaauggu agaacucacacu | (SEQ ID NO: 4) |
| hsa-miR-183 | uauggcacuggu agaauucacu | (SEQ ID NO: 5) |
| hsa-miR-221 | agcuacauugc ugcuggguuuc | (SEQ ID NO: 6) |
| hsa-miR-497 | cagcagcacacu gugguuugu | (SEQ ID NO: 7) |
| hsa-miR-106a | aaaagugcuuac agugcagguag | (SEQ ID NO: 8) |
| hsa-miR-106b | uaaagugcugac agugcagau | (SEQ ID NO: 9) |
| hsa-miR-18b | uaaggugcaucu agugcaguuag | (SEQ ID NO: 10) |
| hsa-miR-30a | uguaaacauccu cgacuggaag | (SEQ ID NO: 11) |
| hsa-miR-135b | uauggcuuuuca uuccuauguga | (SEQ ID NO: 12) |
| hsa-miR-93 | caaagugcuguu cgugcagguag | (SEQ ID NO: 13) |

TABLE 1-continued

| miRNA | Sequence (5'→3') | |
|---|---|---|
| hsa-miR-17 | caaagugcuuac agugcagguag | (SEQ ID NO: 14) |
| hsa-miR-20b | caaagugcucau agugcagguag | (SEQ ID NO: 15) |
| hsa-miR-24 | uggcucaguuca gcaggaacag | (SEQ ID NO: 16) |
| hsa-miR-423-5p | ugaggggcagag agcgagacuuu | (SEQ ID NO: 17) |
| hsa-let-7a | ugagguaguagg uuguauaguu | (SEQ ID NO: 18) |

For normalizing the expression levels obtained for the nucleic acid molecules encoding microRNA sequences that are comprised in the nucleic acid expression signature the miRNA hsa-miR-423-5p (SEQ ID NO: 17) may be preferably used, which is stably expressed in colorectal tissues. For calibration purposes (i.e. the establishment of standard concentration curves), the miRNA hsa-let-7a (SEQ ID: 18) may be preferably employed.

The terms "one or more of the plurality of nucleic acid molecules" and "any one or more human target cell-derived nucleic acid molecules", as used herein, may relate to any subgroup of the plurality of nucleic acid molecules, e.g., any one, any two, any three, any four, any five, any six, any seven, any eight, any nine, any ten, and so forth nucleic acid molecules, each encoding a microRNA sequence that are comprised in the nucleic acid expression signature, as defined herein.

In preferred embodiments of the invention, the nucleic acid expression signature comprises nucleic acid molecules encoding hsa-miR-224 (SEQ ID NO:1), hsa-miR-183 (SEQ ID NO:5), and hsa-miR-18b (SEQ ID NO:10). In other words, the nucleic acid expression signature includes at least nucleic acid molecules encoding hsa-miR-224, hsa-miR-183, and hsa-miR-18b but may contain one or more additional nucleic acid molecules encoding any further miRNA sequences that are differentially expressed in the target cells and in one or more control cells analyzed, particularly one or more additional nucleic acid molecules encoding any one of the remaining miRNA sequences referred to above (i.e., hsa-miR-96, hsa-miR-21, hsa-miR-182, hsa-miR-221, hsa-miR-497, hsa-miR-106b, hsa-miR-106a, hsa-miR-30a, hsa-miR-135b, hsa-miR-93, hsa-miR-17, hsa-miR-20b, and hsa-miR-24).

In other preferred embodiments of the invention, the nucleic acid expression signature further (that is, in addition to hsa-miR-224, hsa-miR-183, and hsa-miR-18b) comprises nucleic acid molecules encoding hsa-miR-96 (SEQ ID NO:2), hsa-miR-182 (SEQ ID NO:4), and hsa-miR-106a (SEQ ID NO:9). Thus, in other words, the nucleic acid expression signature includes at least nucleic acid molecules encoding hsa-miR-224, hsa-miR-183, hsa-miR-18b, hsa-miR-96, hsa-miR-182, and hsa-miR-106a but may contain one or more additional nucleic acid molecules encoding any further miRNA sequences that are differentially expressed in the target cells and in one or more control cells analyzed, particularly one or more additional nucleic acid molecules encoding any one of the remaining miRNA sequences referred to above (i.e., hsa-miR-21, hsa-miR-221, hsa-miR-497, hsa-miR-106b, hsa-miR-30a, hsa-miR-135b, hsa-miR-93, hsa-miR-17, hsa-miR-20b, and hsa-miR-24).

In a particularly preferred embodiment of the invention, the nucleic acid expression signature comprises nucleic acid molecules encoding hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, and hsa-miR-30a.

In specific embodiments, the nucleic acid expression signature comprises nucleic acid molecules encoding hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, and hsa-miR-30a, and further comprises nucleic acid molecules encoding hsa-miR-135b, hsa-miR-93, hsa-miR-17, hsa-miR-20b, and hsa-miR-24.

In further particularly preferred embodiments, the expression of the nucleic acid molecules encoding hsa-miR-224, hsa-miR-96, hsa-miR-21, hsa-miR-182, hsa-miR-183, hsa-miR-221, hsa-miR-106b, hsa-miR-106a, hsa-miR-18b, hsa-miR-135b, hsa-miR-93, hsa-miR-17, hsa-miR-20b, and hsa-miR-24 is up-regulated and the expression of the nucleic acid molecules hsa-miR-497 and hsa-miR-30a is down-regulated in the in the one or more target cells compared to the one or more control cells.

In further embodiments of the invention, the nucleic acid expression signature includes at least any one or more nucleic acid molecules encoding the miRNAs specified above and also contains one or more additional nucleic acid molecules encoding any further miRNA sequences that are differentially expressed in the target cells and in one or more control cells analyzed, particularly any one or more human target cell-derived nucleic acid molecules encoding microRNA sequences selected from the group consisting of miR-374a (SEQ ID NO:19), hsa-miR-21* (SEQ ID NO:20), hsa-miR-34a (SEQ ID NO:21), hsa-miR-203 (SEQ ID NO:22), hsa-miR-29b (SEQ ID NO:23), hsa-miR-145 (SEQ ID NO:24), hsa-miR-195 (SEQ ID NO:25), hsa-miR-27a (SEQ ID NO:26), hsa-miR-30e* (SEQ ID NO:27), hsa-miR-30c (SEQ ID NO:28), hsa-miR-29c (SEQ ID NO:29), hsa-miR-342-3p (SEQ ID NO:30), hsa-miR-125a-3p (SEQ ID NO:31), hsa-miR-23a (SEQ ID NO:32), hsa-miR-31 (SEQ ID NO:33), hsa-miR-375 (SEQ ID NO:34), hsa-miR-551b (SEQ ID NO:35), hsa-miR-572 (SEQ ID NO:36), hsa-miR-638 (SEQ ID NO:37), hsa-miR-650 (SEQ ID NO:38), hsa-miR-7 (SEQ ID NO:39), hsa-miR-939 (SEQ ID NO:40), hsa-miR-150 (SEQ ID NO:41), hsa-miR-18a (SEQ ID NO:42), hsa-miR-19a (SEQ ID NO:43), hsa-miR-424 (SEQ ID NO:44), hsa-miR-552 (SEQ ID NO:45), hsa-miR-92a (SEQ ID NO:46), hsa-miR-1 (SEQ ID NO:47), hsa-miR-133b (SEQ ID NO:48), hsa-miR-20a (SEQ ID NO:49), hsa-miR-378 (SEQ ID NO:50), hsa-miR-378* (SEQ ID NO:51), hsa-miR-181c (SEQ ID NO:52), hsa-miR-592 (SEQ ID NO:53), hsa-miR-452 (SEQ ID NO:54), hsa-miR-139-5p (SEQ ID NO:55), hsa-miR-192 (SEQ ID NO:56), hsa-miR-194 (SEQ ID NO:57), hsa-miR-374b (SEQ ID NO:58), hsa-miR-95 (SEQ ID NO:59), hsa-miR-139-3p (SEQ ID NO:60), hsa-miR-29a (SEQ ID NO:61), hsa-miR-455-3p (SEQ ID NO:62), hsa-miR-25 (SEQ ID NO:63), hsa-miR-130b (SEQ ID NO:64), hsa-miR-17* (SEQ ID NO:65), hsa-miR-20a* (SEQ ID NO:66), hsa-miR-215 (SEQ ID NO:67), hsa-miR-10b (SEQ ID NO:68), hsa-miR-19b (SEQ ID NO:69), hsa-miR-451 (SEQ ID NO:70), hsa-miR-143 (SEQ ID NO:71), hsa-miR-145* (SEQ ID NO:72), hsa-miR-22 (SEQ ID NO:73), hsa-miR-222 (SEQ ID NO:74), hsa-miR-122 (SEQ ID NO:75), has-miR-199b-5p (SEQ ID NO:76), hsa-miR-365 (SEQ ID NO:77), hsa-miR-660 (SEQ ID NO:78), hsa-miR-100 (SEQ ID NO:79), hsa-miR-107 (SEQ ID NO:80), hsa-miR-148b (SEQ ID NO:81), hsa-miR-204 (SEQ ID NO:82), hsa-miR-376c (SEQ ID NO:83), hsa-miR-625 (SEQ ID NO:84), hsamiR-429 (SEQ ID NO:85), hsa-miR-127-3p (SEQ ID NO:86), hsa-miR-199b-3p (SEQ ID NO:87), hsa-miR-26b (SEQ ID NO:88), hsa-miR-31* (SEQ ID NO:89), hsa-miR-483-3p (SEQ ID NO:90), hsa-miR-483-5p (SEQ ID NO:91), hsa-miR-503 (SEQ ID NO:92), hsa-miR-513c (SEQ ID NO:93), hsa-miR-26a (SEQ ID NO:94), hsa-miR-1225-5p (SEQ ID NO:95), hsa-miR-128 (SEQ ID NO:96), hsa-miR-134 (SEQ ID NO:97), hsa-miR-194* (SEQ ID NO:98), hsa-miR-29b-1* (SEQ ID NO:99), hsa-miR-30e (SEQ ID NO:100), hsa-miR-338-3p (SEQ ID NO:101), hsa-miR-34b* (SEQ ID NO:102), hsa-miR-623 (SEQ ID NO:103), hsa-miR-662 (SEQ ID NO:104), hsa-miR-98 (SEQ ID NO:105), hsa-miR-99a (SEQ ID NO:106), hsa-miR-19b-1* (SEQ ID NO:107), hsa-miR-335 (SEQ ID NO:108), hsa-miR-766 (SEQ ID NO:109), hsa-miR-550* (SEQ ID NO:110), hsa-miR-151-3p (SEQ ID NO:111), hsa-miR-301a (SEQ ID NO:112), hsa-miR-335* (SEQ ID NO:113), hsa-miR-342-5p (SEQ ID NO:114), hsa-miR-132 (SEQ ID NO:115), hsa-miR-135a* (SEQ ID NO:116), hsa-miR-146b-5p (SEQ ID NO:117), hsa-miR-192* (SEQ ID NO:118), hsa-miR-23b (SEQ ID NO:119), hsa-miR-29c* (SEQ ID NO:120), hsa-miR-376a (SEQ ID NO:121), hsa-miR-486-5p (SEQ ID NO:122), and hsa-miR-196b (SEQ ID NO:123).

In specific embodiments of the invention, the nucleic acid expression signature, as defined above, is for the further use of particularly discriminating adenomas and includes at least any one or more nucleic acid molecules encoding microRNA sequences selected from the group consisting of hsa-miR-100, hsa-miR-107, hsa-miR-148b, hsa-miR-204, hsa-miR-376c, hsa-miR-625, hsa-miR-429, hsa-miR-127-3p, hsa-miR-199b-3p (SEQ ID NO:79 to SEQ ID NO:87).

In other specific embodiments of the invention, the nucleic acid expression signature, as defined above, is for the further use of particularly discriminating adenocarcimas classified as Dukes A and includes at least any one or more nucleic acid molecules encoding microRNA sequences selected from the group consisting of hsa-miR-26b, hsa-miR-31*, hsa-miR-483-3p, hsa-miR-483-5p, hsa-miR-503, hsa-miR-513c, hsa-miR-26a (SEQ ID NO:88 to SEQ ID NO:94):

In further specific embodiments of the invention, the nucleic acid expression signature, as defined above, is for the further use of particularly discriminating adenocarcimas classified as Dukes B and includes at least any one or more nucleic acid molecules encoding microRNA sequences selected from the group consisting of hsa-miR-1225-5p, hsa-miR-128, hsa-miR-134, hsa-miR-194*, hsa-miR-29b-1*, hsa-miR-30e, hsa-miR-338-3p, hsa-miR-34b*, hsa-miR-623, hsa-miR-662, hsa-miR-98, hsa-miR-99a, hsa-miR-19b-1*, hsa-miR-335, hsa-miR-766, hsa-miR-550* (SEQ ID:95 to SEQ ID:110):

In further specific embodiments of the invention, the nucleic acid expression signature, as defined above, is for the further use of particularly discriminating adenocarcimas classified as Dukes C and includes at least any one or more nucleic acid molecules encoding microRNA sequences selected from the group consisting of hsa-miR-151-3p, hsa-miR-301a, hsa-miR-335*, hsa-miR-342-5p (SEQ ID NO:111 to SEQ ID NO:114).

In other specific embodiments of the invention, the nucleic acid expression signature, as defined above, is for the further use of particularly discriminating adenocarcimas classified as Dukes D and includes at least any one or more nucleic acid molecules encoding microRNA sequences selected from the group consisting of hsa-miR-132, hsa-miR-135a*, hsa-miR-146b-5p, hsa-miR-192*, hsa-miR-23b, hsa-miR-29c*, hsa-miR-376a, hsa-miR-486-5p, hsa-miR-196b (SEQ ID NO:115 to SEQ ID NO:123).

In further preferred embodiments of the invention, the nucleic acid expression signature of the diagnostic kit for exhibiting or having a predisposition to develop colorectal adenoma comprises any one or more human target cell-derived nucleic acid molecules encoding microRNA sequences selected from the group consisting of hsa-miR-376a (SEQ ID NO:121), hsa-miR-429 (SEQ ID NO:85), hsa-miR-451 (SEQ ID NO:70) and hsa-miR-99a (SEQ ID NO:106).

Preferably, the nucleic acid expression signature of the diagnostic kit for exhibiting or having a predisposition to develop colorectal adenoma comprises any one or more human target cell-derived nucleic acid molecules encoding microRNA sequences selected from the group consisting of hsa-miR-376a (SEQ ID NO:121) and hsa-miR-99a (SEQ ID NO:106).

The nucleic acid sequences of the above-referenced miRNAs are listed in Table 2.

TABLE 2

| miRNA | Sequence (5' to 3') | |
|---|---|---|
| hsa-miR-376a | aucauagagg aaaauccacg u | (SEQ ID NO: 121) |
| hsa-miR-429 | uaauacuguc ugguaaaacc gu | (SEQ ID NO: 85) |
| hsa-miR-451 | aaaccguuac cauuacugag uu | (SEQ ID NO: 70) |
| hsa-miR-99a | aacccguaga uccgaucuug ug | (SEQ ID NO: 79) |

Particularly preferably, the expression of any one or more of the nucleic acid molecules encoding hsa-miR-429 is up-regulated and the expression of any one or more of the nucleic acid molecules hsa-miR-376a, hsa-miR-451, and hsa-miR-99a is down-regulated in the in the one or more target cells compared to the one or more control cells (cf. FIG. 5).

In further embodiments of the invention, the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p (SEQ ID NO:55), hsa-miR-497 (SEQ ID NO:7), hsa-miR-378* (SEQ ID NO:51), hsa-miR-182 (SEQ ID NO:4), hsa-miR-20b (SEQ ID NO:15), hsa-miR-17* (SEQ ID NO:65), hsa-miR-376c (SEQ ID NO:83), hsa-miR-20a* (SEQ ID NO:66), hsa-miR-638 (SEQ ID NO:37), hsa-miR-335* (SEQ ID NO:113), hsa-miR-342-5p (SEQ ID NO:114), hsa-miR-34b* (SEQ ID NO:102), hsa-miR-145* (SEQ ID NO:72), and hsa-miR-552 (SEQ ID NO:45).

Preferably. the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p (SEQ ID NO:55), hsa-miR-497 (SEQ ID NO:7), hsa-miR-378* (SEQ ID NO:51), hsa-miR-182 (SEQ ID NO:4), hsa-miR-20b (SEQ ID NO:15), hsa-miR-17* (SEQ ID NO:65), hsa-miR-376c (SEQ ID NO:83), hsa-miR-20a* (SEQ ID NO:66).

More preferably, the nucleic acid expression signature of the diagnostic kit for exhibiting or having a predisposition to develop colorectal adenoma and carcinoma comprises any one or more human target cell-derived nucleic acid molecules encoding microRNA sequences selected from the group consisting of hsa-miR-139-5p (SEQ ID NO:55), hsa-miR-497 (SEQ ID NO:7), hsa-miR-378* (SEQ ID NO:51), hsa-miR-182 (SEQ ID NO:4).

The nucleic acid sequences of the above-referenced miRNAs are listed in Table 3.

TABLE 3

| miRNA | Sequence (5' to 3') | |
|---|---|---|
| hsa-miR-139-5p | ucuacagugc acgugucucc ag | (SEQ ID NO: 55) |
| hsa-miR-497 | cagcagcaca cugugguuug u | (SEQ ID NO: 7) |
| hsa-miR-378* | cuccugacuc cagguccugu gu | (SEQ ID NO: 51) |
| hsa-miR-182 | uuuggcaaug guagaacuca cacu | (SEQ ID NO: 6) |
| hsa-miR-20b | caaagugcuc auagugcagg uag | (SEQ ID NO: 15) |
| hsa-miR-17* | acugcaguga aggcacuugu ag | (SEQ ID NO: 65) |
| hsa-miR-376c | aacauagagg aaauuccacg u | (SEQ ID NO: 83) |
| hsa-miR-20a* | acugcauuau gagcacuuaa ag | (SEQ ID NO: 66) |
| hsa-miR-638 | agggaucgcg ggcggguggc ggccu | (SEQ ID NO: 37) |
| hsa-miR-335* | uuuuucauua uugcuccuga cc | (SEQ ID NO: 113) |
| hsa-miR-342-5p | aggggugcua ucugugauug a | (SEQ ID NO: 114) |
| hsa-miR-34b* | uaggcagugu cauuagcuga uug | (SEQ ID NO: 102) |
| hsa-miR-145* | ggauuccugg aaauacuguu cu | (SEQ ID NO: 72) |
| hsa-miR-552 | aacaggugac ugguuagaca a | (SEQ ID NO: 45) |

Particularly preferably, the expression of any one or more of the nucleic acid molecules encoding hsa-miR-182, hsa-miR-20b, hsa-miR-17*, hsa-miR-20a*, hsa-miR-335*, hsa-miR-34b*, and hsa-miR-552 is up-regulated and the expression of any one or more of the nucleic acid molecules hsa-miR-139-5p, hsa-miR-497, hsa-miR-378*, hsa-miR-376c, hsa-miR-638, hsa-miR-342-5p, and hsa-miR-145*is down-regulated in the in the one or more target cells compared to the one or more control cells (cf. FIG. 5).

In other embodiments of the invention, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424 (SEQ ID NO:44), hsa-miR-378 (SEQ ID NO:50), hsa-miR-375 (SEQ ID NO:34), hsa-miR-139-3p (SEQ ID NO:60), hsa-miR-18b (SEQ ID NO:10), hsa-miR-18a (SEQ ID NO:42), hsa-miR-650 (SEQ ID NO:38), hsa-miR-194* (SEQ ID NO:98), hsa-miR-194 (SEQ ID NO:57), hsa-miR-29c (SEQ ID NO:120), hsa-miR-939 (SEQ ID NO:40), hsa-miR-181c (SEQ ID NO:52), hsa-miR-513c (SEQ ID NO:93), hsa-miR-572 (SEQ ID NO:36), hsa-miR-130b (SEQ ID NO:64), hsa-miR-30e (SEQ ID NO:100), hsa-miR-455-3p (SEQ ID NO:62), hsa-miR-192* (SEQ ID NO:118), hsa-miR-301a (SEQ ID NO:112), hsa-miR-452 (SEQ ID NO:54), hsa-miR-98 (SEQ ID NO:105), hsa-miR-486-5p (SEQ ID NO:122), hsa-miR-662 (SEQ ID NO:104), hsa-miR-19b (SEQ ID NO:69), hsa-miR-30e* (SEQ ID NO:27), hsa-miR-151-3p (SEQ ID NO:111), hsa-miR-29c* (SEQ ID NO:120), hsa-miR-623 (SEQ ID NO:103), hsa-miR-550* (SEQ ID NO:110), hsa-miR-134 (SEQ ID NO:97), hsa-miR-128 (SEQ ID NO:96), and hsa-miR-21* (SEQ ID NO:20).

Preferably, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424 (SEQ ID NO:44), hsa-miR-378 (SEQ ID NO:50), hsa-miR-375 (SEQ ID NO:34), hsa-miR-139-3p (SEQ ID NO:60), hsa-miR-18b (SEQ ID NO:10), hsa-miR-18a (SEQ ID NO:42), hsa-miR-650 (SEQ ID NO:38), hsa-miR-194* (SEQ ID NO:98), hsa-miR-194 (SEQ ID NO:57), hsa-miR-29c (SEQ ID NO:120), hsa-miR-939 (SEQ ID NO:40), hsa-miR-181c (SEQ ID NO:52).

More preferably, the nucleic acid expression signature of the diagnostic kit for exhibiting or having a predisposition to develop colorectal carcinoma comprises any one or more human target cell-derived nucleic acid molecules encoding microRNA sequences selected from the group consisting of hsa-miR-424 (SEQ ID NO:44), hsa-miR-378 (SEQ ID NO:50), hsa-miR-375 (SEQ ID NO:34), hsa-miR-139-3p (SEQ ID NO:60), hsa-miR-18b (SEQ ID NO:10), hsa-miR-18a (SEQ ID NO:42).

The nucleic acid sequences of the above-referenced miRNAs are listed in Table 4.

TABLE 4

| miRNA | Sequence (5' to 3') | |
|---|---|---|
| hsa-miR-424 | cagcagcaau ucauguuuug aa | (SEQ ID NO: 44) |
| hsa-miR-378 | acuggacuug gagucagaag g | (SEQ ID NO: 50) |
| hsa-miR-375 | uuuguucguu cggcucgcgu ga | (SEQ ID NO: 34) |
| hsa-miR-139-3p | ggagacgcgg cccuguugga gu | (SEQ ID NO: 60) |
| hsa-miR-18b | uaaggugcau cuagugcagu uag | (SEQ ID NO: 10) |
| hsa-miR-18a | uaaggugcau cuagugcaga uag | (SEQ ID NO: 42) |
| hsa-miR-650 | aggaggcagc gcucucagga c | (SEQ ID NO: 38) |
| hsa-miR-194* | ccaguggggc ugcuguuauc ug | (SEQ ID NO: 98) |
| hsa-miR-194 | uguaacagca acuccaugug ga | (SEQ ID NO: 57) |
| hsa-miR-29c | uagcaccauu ugaaaucggu ua | (SEQ ID NO: 29) |
| hsa-miR-939 | uggggagcug aggcucuggg ggug | (SEQ ID NO: 40) |
| hsa-miR-181c | aacauucaac cugucgguga gu | (SEQ ID NO: 52) |

TABLE 4-continued

| miRNA | Sequence (5' to 3') | |
|---|---|---|
| hsa-miR-513c | uucucaagga ggugucguuu au | (SEQ ID NO: 93) |
| hsa-miR-572 | guccgcucgg cgguggccca | (SEQ ID NO: 36) |
| hsa-miR-130b | cagugcaaug augaaagggc au | (SEQ ID NO: 64) |
| hsa-miR-30e | uguaaacauc cuugacugga ag | (SEQ ID NO: 100) |
| hsa-miR-455-3p | gcaguccaug ggcauauaca c | (SEQ ID NO: 62) |
| hsa-miR-192* | cugccaauuc cauaggucac ag | (SEQ ID NO: 118) |
| hsa-miR-301a | cagugcaaua guauugucaa agc | (SEQ ID NO: 112) |
| hsa-miR-452 | aacuguuugc agaggaaacu ga | (SEQ ID NO: 54) |
| hsa-miR-98 | ugagguagua aguuguauug uu | (SEQ ID NO: 105) |
| hsa-miR-486-5p | uccuguacug agcugcccg ag | (SEQ ID NO: 122) |
| hsa-miR-662 | ucccacguug uggcccagca g | (SEQ ID NO: 104) |
| hsa-miR-19b | ugugcaaauc caugcaaaac uga | (SEQ ID NO: 69) |
| hsa-miR-30e* | cuuucagucg gauguuuaca gc | (SEQ ID NO: 27) |
| hsa-miR-151-3p | cuagacugaa gcuccuugag g | (SEQ ID NO: 111) |
| hsa-miR-29c* | ugaccgauuu cuccuggugu uc | (SEQ ID NO: 120) |
| hsa-miR-623 | aucccuugca ggggcuguug ggu | (SEQ ID NO: 103) |
| hsa-miR-550* | ugucuuacuc ccucaggcac au | (SEQ ID NO: 110) |
| hsa-miR-134 | ugugacuggu ugaccagagg gg | (SEQ ID NO: 97) |
| hsa-miR-128 | ucacagugaa ccggucucuu u | (SEQ ID NO: 96) |
| hsa-miR-21* | caacaccagu cgaugggcug u | (SEQ ID NO: 20) |

Particularly preferably, the expression of any one or more of the nucleic acid molecules encoding hsa-miR-424, hsa-miR-18b, hsa-miR-18a, hsa-miR-181c, hsa-miR-130b, hsa-miR-455-3p, hsa-miR-301a, hsa-miR-452, hsa-miR-98, hsa-miR-19b; hsa-miR-151-3p, hsa-miR-550*, hsa-miR-128, and hsa-miR-21* is up-regulated and the expression of any one or more of the nucleic acid molecules hsa-miR-378, hsa-miR-375, hsa-miR-139-3p, hsa-miR-650, hsa-miR-194*, hsa-miR-194, hsa-miR-29c, hsa-miR-939, hsa-miR-513c, hsa-miR-572, hsa-miR-30e, hsa-miR-192*, hsa-miR-486-5p, hsa-miR-662, hsa-miR-30e*, hsa-miR-29c*, hsa-miR-623, and hsa-miR-134 is down-regulated in the in the one or more target cells compared to the one or more control cells (cf. FIG. 5).

In further embodiments of the present invention, the nucleic acid expression signature comprises at least any one or more nucleic acid molecules encoding miRNAs specified above and also contains one or more additional nucleic acid molecules encoding any further miRNA sequences that are differentially expressed in the target cells and in one or more control cells analyzed, particularly any one or more human taget cell-derived nucleic acid molecules encoding miRNA sequences selected from the group consisting of SEQ ID NO: 1 to SEQ ID NO: 123.

All miRNA sequences disclosed herein have been deposited in the miRBase database www<<.>>mirbase<<.>>org; see also Griffiths-Jones S. et al. (2008) *Nucl. Acids Res.* 36, D154-D158). In a second aspect, the present invention relates to a method for identifying one or more mammalian target cells exhibiting or having a predisposition to develop colorectal cancer, the method comprising:

(a) determining in the one or more target cells the expression levels of a plurality of nucleic acid molecules, each nucleic acid molecule encoding a microRNA sequence;
(b) determining the expression levels of the plurality of nucleic acid molecules in one or more control cells; and
(c) identifying from the plurality of nucleic acid molecules one or more nucleic acid molecules that are differentially expressed in the target and control cells by comparing the respective expression levels obtained in steps (a) and (b), wherein the one or more differentially expressed nucleic acid molecules together represent a nucleic acid expression signature, as defined herein, that is indicative for the presence of or the predisposition to develop colorectal cancer.

Preferably, the colorectal cancer is manifested as an adenocarcinoma.

In preferred embodiments of the invention, the method is for the further use of identifying a progression of an adenoma to an adenocarcinoma or a predisposition for a progression of an adenoma to an adenocarcinoma.

The method of the present invention comprises determining and comparing the expression levels of a plurality of nucleic acid molecules encoding a microRNA sequence both in one or more target cells supposed to exhibit or to have a predisposition to develop colorectal cancer and in one or more control cells, i.e. typically wild-type cells not showing the characteristics of such a cancerous phenotype (cf. also the discussion above).

In a third aspect, the invention relates to a method for preventing or treating colorectal cancer, preferably manifested as an adenocarcinoma, in one or more mammalian target cells, the method comprising:

(a) identifying in one or more target cells a nucleic acid expression signature by using a method, as defined herein; and
(b) modifying in the one or more cells the expression of one or more nucleic acid molecules encoding a microRNA sequence that is/are comprised in the nucleic acid expression signature in such way that the expression of a nucleic acid molecule whose expression is up-regulated in the one or more target cells is down-regulated and the expression of a nucleic acid molecule whose expression is down-regulated in the one or more target cells is up-regulated.

The term "modifying the expression of a nucleic acid molecule encoding a miRNA sequence", as used herein, denotes any manipulation of a particular nucleic acid molecule resulting in an altered expression level of said molecule, that is, the production of a different amount of corresponding miRNA as compared to the expression of the "wild-type" (i.e. the unmodified control). The term "different amount", as used herein, includes both a higher amount and a lower amount than determined in the unmodified control. In other words, a manipulation, as defined herein, may either up-regulate (i.e. activate) or down-regulate (i.e. inhibit) the expression (i.e. particularly transcription) of a nucleic acid molecule.

Within the present invention, expression of one or more nucleic acid molecules encoding a microRNA sequence comprised in the nucleic acid expression signature is modified in such way that the expression of a nucleic acid molecule whose expression is up-regulated in the one or more target cells is down-regulated and the expression of a nucleic acid molecule whose expression is down-regulated in the one or more target cells is up-regulated. In other words, the modification of expression of a particular nucleic acid molecule encoding a miRNA sequence occurs in an anti-cyclical pattern to the regulation of said molecule in the one or more cancerous target cells in order to interfere with the "excess activity" of an up-regulated molecule and/or to restore the "deficient activity" of a down-regulated molecule in the one or more target cells.

In a preferred embodiment of the inventive method, down-regulating the expression of a nucleic acid molecule comprises introducing into the one or more target cells a nucleic acid molecule encoding a sequence that is complementary to the microRNA sequence encoded by nucleic acid molecule to be down-regulated.

The term "introducing into a cell", as used herein, refers to any manipulation allowing the transfer of one or more nucleic acid molecules into a cell. Examples of such techniques include inter alia transfection or transduction techniques all of them well established in the art (cf., for example, Sambrook, J. et al. (1989) *Molecular, Cloning: A Laboratory Manual*, 2nd ed., Cold Spring Harbor Laboratory Press, Cold Spring Harbor, N.Y.; Ausubel, F. M. et al. (2001) *Current Protocols in Molecular Biology*, Wiley & Sons, Hoboken, N.J.).

The term "complementary sequence", as used herein, is to be understood that the "complementary" nucleic acid molecule (herein also referred to as an "anti-sense nucleic acid molecule") introduced into the one or more cells is capable of forming base pairs, preferably Watson-Crick base pairs, with the up-regulated endogenous "sense" nucleic acid molecule.

Two nucleic acid molecules (i.e. the "sense" and the "anti-sense" molecule) may be perfectly complementary, that is, they do not contain any base mismatches and/or additional or missing nucleotides. In other embodiments, the two molecules comprise one or more base mismatches or differ in their total numbers of nucleotides (due to additions or deletions). In further embodiments, the "complementary" nucleic acid molecule comprises at least ten contiguous nucleotides showing perfect complementarity with a sequence comprised in the up-regulated "sense" nucleic acid molecule.

The "complementary" nucleic acid molecule (i.e. the nucleic acid molecule encoding a nucleic acid sequence that is complementary to the microRNA sequence encoded by nucleic acid molecule to be down-regulated) may be a naturally occurring DNA- or RNA molecule or a synthetic nucleic acid molecule comprising in its sequence one or more modified nucleotides which may be of the same type or of one or more different types.

For example, it may be possible that such a nucleic acid molecule comprises at least one ribonucleotide backbone unit and at least one deoxyribonucleotide backbone unit. Furthermore, the nucleic acid molecule may contain one or more modifications of the RNA backbone into 2'-O-methyl group or 2'-O-methoxyethyl group (also referred to as "2'-O-methylation"), which prevented nuclease degradation in the culture media and, importantly, also prevented endonucleolytic cleavage by the RNA-induced silencing complex nuclease, leading to irreversible inhibition of the miRNA. Another possible modification—which is functionally equivalent to 2'-O-methylation—involves locked nucleic acids (LNAs) representing nucleic acid analogs containing one or more LNA nucleotide monomers with a bicyclic furanose unit locked in an RNA-mimicking sugar conformation (cf., e.g., Orom, U. A. et al. (2006) *Gene* 372, 137-141).

Another class of silencers of miRNA expression was recently developed. These chemically engineered oligonucleotides, named "antagomirs", represent single-stranded 23-nucleotide RNA molecules conjugated to cholesterol (Krutzfeldt, J. et al. (2005) *Nature* 438, 685-689). As an alternative to such chemically modified oligonucleotides, microRNA inhibitors that can be expressed in cells, as RNAs produced from transgenes, were generated as well. Termed "microRNA sponges", these competitive inhibitors are transcripts expressed from strong promoters, containing multiple, tandem binding sites to a microRNA of interest (Ebert, M. S. et al. (2007) *Nat. Methods* 4, 721-726).

In particularly preferred embodiments of the inventive method, the one or more nucleic acid molecules whose expression is to be down-regulated encode microRNA sequences selected from the group consisting of hsa-miR-224, hsa-miR-96, hsa-miR-21, hsa-miR-182, hsa-miR-183, hsa-miR-221, hsa-miR-106b, hsa-miR-106a, and hsa-miR-18b.

In a further preferred embodiment of the inventive method, up-regulating the expression of a nucleic acid molecule comprises introducing into the one or more target cells a nucleic acid molecule encoding the microRNA sequence encoded by nucleic acid molecule to be up-regulated. In other words, the up-regulation of the expression of a nucleic acid molecule encoding a miRNA sequence is accomplished by introducing into the one or more cells another copy of said miRNA sequence (i.e. an additional "sense" nucleic acid molecule). The "sense" nucleic acid molecule to be introduced into the one or more target cells may comprise the same modification as the "anti-sense" nucleic acid molecules described above.

In a particularly preferred embodiment, the one or more nucleic acid molecules whose expression is to be up-regulated encode microRNA sequences selected from the group consisting of hsa-miR-497 and hsa-miR-30a.

The "sense" and/or the "anti-sense" nucleic acid molecules to be introduced into the one or more target cells in order to modify the expression of one or more nucleic acid molecules encoding a microRNA sequence that is/are comprised in the nucleic acid expression signature may be operably linked to a regulatory sequence in order to allow expression of the nucleotide sequence.

In order to unravel any potential implication of the miR-NAs identified in the cancerous or pre-cancerous samples preliminary functional analyses may be performed with respect to the identification of mRNA target sequences to which the miRNAs may bind. Based on the finding that miR-NAs may be involved in both tumor suppression and tumorigenesis (reviewed, e.g., in Esquela-Kerscher, A. and Slack, F. J (2006) supra; Calin, G. A. and Croce, C. M. (2007) supra; Blenkiron, C. and Miska, E. A. (2007) supra) it is likely to speculate that mRNA target sites for such miRNAs include tumor suppressor genes as well as oncogenes.

A nucleic acid molecule is referred to as "capable of expressing a nucleic acid molecule" or capable "to allow expression of a nucleotide sequence" if it comprises sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed (and/or the sequences to be expressed among each other) are connected in a way that enables gene expression.

The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Furthermore, the expression of the nucleic molecules, as defined herein, may also be influenced by the presence, e.g., of modified nucleotides (cf. the discussion above). For example, locked nucleic acid (LNA) monomers are thought to increase the functional half-life of miRNAs in vivo by enhancing the resistance to degradation and by stabilizing the miRNA-target duplex structure that is crucial for silencing activity (cf., e.g., Naguibneva, I. et al. (2006) *Biomed. Pharmacother.* 60, 633-638).

Therefore, a nucleic acid molecule of the invention to be introduced into the one or more cells provided may include a regulatory sequence, preferably a promoter sequence, and optionally also a transcriptional termination sequence.

The promoters may allow for either a constitutive or an inducible gene expression. Suitable promoters include inter alia the *E. coli* lacUV5 and tet (tetracycline-responsive) promoters, the T7 promoter as well as the SV40 promoter or the CMV promoter.

The nucleic acid molecules of the invention may also be comprised in a vector or other cloning vehicles, such as plasmids, phagemids, phages, cosmids or artificial chromosomes. In a preferred embodiment, the nucleic acid molecule is comprised in a vector, particularly in an expression vector. Such an expression vector can include, aside from the regulatory sequences described above and a nucleic acid sequence encoding a genetic construct as defined in the invention, replication and control sequences derived from a species compatible with the host that is used for expression as well as selection markers conferring a selectable phenotype on transfected cells. Large numbers of suitable vectors such as pSUPER and pSUPERIOR are known in the art, and are commercially available.

In a forth aspect, the invention relates to a pharmaceutical composition for the prevention and/or treatment of colorectal cancer, preferably manifested as an adenocarcinoma, in one or more mammalian target cells, the composition comprising one or more nucleic acid molecules, each nucleic acid molecule encoding a sequence that is at least partially complementary to a microRNA sequence encoded by a nucleic acid molecule whose expression is up-regulated in the one or more target cells, as defined herein, and/or that corresponds to a microRNA sequence encoded by a nucleic acid molecule whose expression is down-regulated in the one or more target cells, as defined herein.

In a final aspect, the invention is directed to the use of such a pharmaceutical composition for the manufacture of a medicament for the prevention and/or treatment of colorectal cancer, preferably manifested as an adenocarcinoma.

In the context of the present invention, suitable pharmaceutical compositions include those suitable for oral, rectal, nasal, topical (including buccal and sub-lingual), peritoneal and parenteral (including intramuscular, subcutaneous and intravenous) administration, or for administration by inhalation or insufflation. Administration may be local or systemic. Preferably, administration is accomplished via the oral, rectal or intravenous routes. The formulations may be packaged in discrete dosage units.

Pharmaceutical compositions according to the present invention include any pharmaceutical dosage forms established in the art, such as inter alia capsules, microcapsules, cachets, pills, tablets, powders, pellets, multi-particulate formulations (e.g., beads, granules or crystals), aerosols, sprays, foams, solutions, dispersions, tinctures, syrups, elixirs, suspensions, water-in-oil emulsions such as ointments, and oil-in water emulsions such as creams, lotions, and balms.

The ("sense" and "anti-sense") nucleic acid molecules described above can be formulated into pharmaceutical compositions using pharmacologically acceptable ingredients as well as established methods of preparation (Gennaro, A. L. and Gennaro, A. R. (2000) *Remington: The Science and Practice of Pharmacy*, 20th Ed., Lippincott Williams & Wilkins, Philadelphia, Pa.; Crowder, T. M. et al. (2003) *A Guide to Pharmaceutical Particulate Science*. Interpharm/CRC, Boca Raton, Fla.; Niazi, S. K. (2004) *Handbook of Pharmaceutical Manufacturing Formulations*, CRC Press, Boca Raton, Fla.).

In order to prepare the pharmaceutical compositions, pharmaceutically inert inorganic or organic excipients (i.e. carriers) can be used. To prepare e.g. pills, tablets, capsules or granules, for example, lactose, talc, stearic acid and its salts, fats, waxes, solid or liquid polyols, natural and hardened oils may be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils. The pharmaceutical composition may also contain additives, such as, for example, fillers, binders, wetting agents, glidants, stabilizers, preservatives, emulsifiers, and furthermore solvents or solubilizers or agents for achieving a depot effect. The latter is to be understood that the nucleic acid molecules may be incorporated into slow or sustained release or targeted delivery systems, such as liposomes, nanoparticles, and microcapsules.

To target most tissues within the body, clinically feasible noninvasive strategies are required for directing such pharmaceutical compositions, as defined herein, into cells. In the past years, several approaches have achieved impressive therapeutic benefit following intravenous injection into mice and primates using reasonable doses of siRNAs without apparent limiting toxicities.

One approach involves covalently coupling the passenger strand (miRNA* strand) of the miRNA to cholesterol or derivatives/conjugates thereof to facilitate uptake through ubiquitously expressed cell-surface LDL receptors (Soutschek, J. et al. (2004) *Nature* 432, 173-178). Alternatively, unconjugated, PBS-formulated locked-nucleic-acid-modified oligonucleotides (LNA-antimiR) may be used for systemic delivery (Elmen, J. et al. (2008) *Nature* 452, 896-899).

Another strategy for delivering miRNAs involves encapsulating the miRNAs into specialized liposomes formed using polyethylene glycol to reduce uptake by scavenger cells and enhance time spent in the circulation. These specialized nucleic acid particles (stable nucleic acid-lipid particles or SNALPs) delivered miRNAs effectively to the liver (and not to other organs (cf., e.g., Zimmermann, T. S. et al. (2006) *Nature* 441, 111-114). Recently, a new class of lipid-like delivery molecules, termed lipidoids (synthesis scheme based upon the conjugate addition of alkylacrylates or alkyl-acrylamides to primary or secondary amines) has been described as delivery agents for RNAi therapeutics (Akinc, A. et al. (2008) *Nat. Biotechnol.* 26, 561-569).

A further cell-specific targeting strategy involves the mixing of miRNAs with a fusion protein composed of a targeting antibody fragment linked to protamine, the basic protein that nucleates DNA in sperm and binds miRNAs by charge (Song, E. et al. (2005) *Nat. Biotechnol.* 23, 709-717). Multiple modifications or variations of the above basic delivery approaches have recently been developed. These techniques are known in the art and reviewed, e.g., in de Fougerolles, A. et al. (2007) *Nat. Rev. Drug Discov.* 6, 443-453; Kim, D. H. and Rossi, J. J. (2007) *Nat. Genet.* 8, 173-184).

The invention is further described by the figures and the following examples, which are solely for the purpose of illustrating specific embodiments of this invention, and are not to be construed as limiting the scope of the invention in any way.

EXAMPLES

Example 1

Sample Collection and Preparation

The principal method steps for identifying one or more target cells in a patient's sample exhibiting or having a predisposition to develop colorectal cancer are shown in FIG. 2.

Surgical specimens were snap-frozen in liquid nitrogen at or immediately after collection. Samples may be stored at −80° C. The following clinical samples were used: 51 normal tissues, 13 inflammatory adenomatous polyps, 16 tubular adenomas, and 59 adenocarcinomas (13 Dukes A, 19 Dukes B, 19 Dukes C, 5 Dukes D, and 3 hepatic metastases).

Patient data (age, sex, imaging data, therapy, other medical conditions, family history, and the like) were derived from the hospital databases for matching the various samples collected. Pathologic follow-up (for example, histological analysis via hematoxylin and eosin (H&E) staining) was used for evidently determining the disease state (i.e. healthy control, adenoma, adenocarcinoma or intermediate state) of a given sample as well as to ensure a consistent classification of the specimens.

Laser-capture micro-dissection was optionally performed for each cancerous sample in order to specifically isolate tumor cell populations (about 200.000 cells). In brief, a transparent transfer film is applied to the surface of a tissue section or specimen. Under a microscope, the thin tissue section is viewed through the glass slide on which it is mounted and clusters of cells are identified for isolation. When the cells of choice are in the center of the field of view, a near IR laser diode integral with the microscope optics is activated. The pulsed laser beam activates a spot on the transfer film, fusing the film with the underlying cells of choice. The transfer film with the bonded cells is then lifted off the thin tissue section (reviewed, e.g., in Emmert-Buck, M. R. et al. (1996). *Science* 274, 998-1001; Espina, V. et al. (2007) *Expert Rev. Mol. Diagn.* 7, 647-657).

The preparation of the cryostat sections and the capturing step using a laser capture microspope (Arcturus Veritas™ Laser Capture Microdissection Instrument (Molecular Devices, Inc., Sunnyvale, Calif., USA) were performed essentially according to the instructions of the manufacturer.

The purification of miRNAs from the clinical samples was performed using the mirVana™ miRNA Isolation Kit (Ambion, Inc., Austin, Tex., USA) according to the manufacturer's instruction.

Example 2

Analysis of the miRNA Expression Profile in the Samples

A qualitative analysis of the miRNAs (differentially) expressed in a particular sample may optionally be performed using the Agilent miRNA microarray platform (Agilent Technologies, Santa Clara, Calif., USA) according to the manufacturer's instructions. The raw data obtained for single-color (CY3) hybridization were normalized by applying a Quantile method and using the R software known in the art.

The quantitative analysis (verification) of the miRNA expression data obtained was typically performed via real-time quantitative RT-PCR employing a TaqMan MicroRNA assay (Applied Biosystems, Foster City, Calif., USA) according to the manufacturer's instructions.

Alternatively, the quantification of the miRNAs may be performed by using real-time quantitative RT-PCR employing SYBR Green I (Sigma Aldrich Corporation, St. Louis, Mo., USA), an asymmetrical cyanine dye binding to double-stranded DNA. The resulting DNA-dye-complex absorbs blue light ($\lambda_{max}$=488 nm) and emits green light ($\lambda_{max}$=522 nm).

A standard concentration curve with synthetic hsa-let-7a miRNA (SEQ ID NO: 18) was established for miRNA quantification, and one stable internal miRNA (hsa-miR-423-5p, SEQ ID NO: 17) was used for normalization during the data analysis.

Prior to miRNA expression analysis, a synthesized heterogenous miRNA may be added ("spiked-in") to the samples at certain ratio with respect to the total RNA concentration as an internal positive control for quantitative analysis. Such a "spike-in" miRNA may be a plant miRNA, for example, ath-miR168a, ath-miR162a, ppt-miR898b, or smo-miR1100, that has a low homology to human gene or transcript sequences. Alternatively, the "spike-in" miRNA may be any sequence 18 nt. to 30 nt. in length that is less than 70% homolog to human gene or transcript sequences.

For assessing whether a particular miRNA is differentially expressed in cancerogenous target cells as compared to healthy control cells the following criteria were used:
  (i) p-value (probability value) of ≤0.05 with a change in expression level of ≥2 in at least 50% of the tumor samples; and
  (ii) p-value of ≤0.05/295 (the factor 295 is due to a Bonferroni correction, since 295 human miRNAs revealed a positive signal on the Agilent miRNA microarray).

In case, at least one of these criteria was fulfilled, the miRNA was considered to be differentially expressed in the target and control cells, respectively.

For quantitative determination, the 11 miRNAs listed in FIG. 1 and Table 1 were selected: hsa-miR-224 (SEQ ID NO:1), hsa-miR-96 (SEQ ID NO:2), hsa-miR-21 (SEQ ID NO:3), hsa-miR-182 (SEQ ID NO:4), hsa-miR-183 (SEQ ID NO:5), hsa-miR-221 (SEQ ID NO:6), hsa-miR-497 (SEQ ID NO:7), hsa-miR-106b (SEQ ID NO:8), hsa-miR-106a (SEQ ID NO:9), hsa-miR-18b (SEQ ID NO:10), hsa-miR-30a (SEQ ID NO:11) hsa-miR-135b (SEQ ID NO:12), hsa-miR-93 (SEQ ID NO:13), hsa-miR-17 (SEQ ID NO:14), hsa-miR-20b (SEQ ID NO:15), and hsa-miR-24 (SEQ ID NO:16).

As a first step, the miRNAs were reverse transcribed following standard procedures using the oligonucleotide primers listed in Table 5. The 3'-ends of the primers are complementary to the 8 terminal nucleotides at 3'-ends of the respective miRNAs (shown in lower case letters and in bold). The 5'-ends of the primers have a common sequence for subsequently performing the real-time PCR (shown in capital letters).

TABLE 5

| miRNA | Primer for reverse transcription (5'→3') | |
|---|---|---|
| hsa-miR-224 | TGTAAAACGACGGCCAG TACTTGGTAaacggaac | (SEQ ID NO: 124) |
| hsa-miR-96 | TGTAAAACGACGGCCAG TACTTGGTAagcaaaaa | (SEQ ID NO: 125) |
| hsa-miR-21 | TGTAAAACGACGGCCAG TACTTGGTAtcaacatc | (SEQ ID NO: 126) |
| hsa-miR-182 | TGTAAAACGACGGCCAG TACTTGGTAagtgtgag | (SEQ ID NO: 127) |
| hsa-miR-183 | TGTAAAACGACGGCCAG TACTTGGTAagtgaatt | (SEQ ID NO: 128) |
| hsa-miR-221 | TGTAAAACGACGGCCAG TACTTGGTAgaaaccca | (SEQ ID NO: 129) |
| hsa-miR-497 | TGTAAAACGACGGCCAG TACTTGGTAacaaacca | (SEQ ID NO: 130) |
| hsa-miR-106a | TGTAAAACGACGGCCAG TACTTGGTActacctgc | (SEQ ID NO: 131) |
| hsa-miR-106b | TGTAAAACGACGGCCAG TACTTGGTAatctgcac | (SEQ ID NO: 132) |
| hsa-miR-18b | TGTAAAACGACGGCCAG TACTTGGTActaactgc | (SEQ ID NO: 133) |
| hsa-miR-30a | TGTAAAACGACGGCCAG TACTTGGTActtccagt | (SEQ ID NO: 134) |
| hsa-miR-135b | TGTAAAACGACGGCCAG TACTTGGTAtcacatag | (SEQ ID NO: 135) |
| hsa-miR-93 | TGTAAAACGACGGCCAG TACTTGGTActacctgc | (SEQ ID NO: 136) |
| hsa-miR-17 | TGTAAAACGACGGCCAG TACTTGGTActacctgc | (SEQ ID NO: 137) |
| hsa-miR-20b | TGTAAAACGACGGCCAG TACTTGGTActacctgc | (SEQ ID NO: 138) |
| hsa-miR-24 | TGTAAAACGACGGCCAGT ACTTGGTActgttcctg | (SEQ ID NO: 139) |

TABLE 5-continued

| miRNA | Primer for reverse transcription (5'→3') | |
|---|---|---|
| hsa-miR-423-5p | TGTAAAACGACGGCCAG TACTTGGTAaaagtctc | (SEQ ID NO: 140) |
| hsa-let-7a | TGTAAAACGACGGCCAG TACTTGGTAaactatac | (SEQ ID NO: 141) |

The reaction mix (per sample) for performing reverse transcription includes:

| | |
|---|---|
| RNA sample | 1.0 µl (10 ng) |
| 10 mM dNTPs | 1.5 µl |
| Reverse Transcriptase (50 U/µl) | 1.0 µl |
| 10× Reverse Transcription Buffer | 1.5 µl |
| RNase Inhibitor, 20 U/µl | 0.2 µl |
| RT primer (10 µM) | 0.3 µl |
| Nuclease-free water | 9.5 µl |

Reverse transcription was performed in a PCR thermal cycler (for example, the 7500 Real-Time PCR System, Applied Biosystems, Inc., Foster City, Calif., USA) using the following parameters:

| Step Type | Time (min) | Temperature (° C.) |
|---|---|---|
| HOLD | 30 | 16 |
| HOLD | 30 | 42 |
| HOLD | 5 | 85 |
| HOLD | ∞ | 4 |

After synthesis of the second cDNA strand according to established standard procedures the real-time PCR is performed. The 5' (up-stream) oligonucleotide primers used for PCR amplification are listed in Table 6. The universal 3' (downstream) primer has the sequence 5'-TGTAAAAC-GACGGCCAG-3' (SEQ ID NO: 160) that is complementary to the 5'-ends of the primers used for reverse transcription (cf. Table 5).

The reaction mix (per sample) for performing real-time PCR includes:

| | |
|---|---|
| RT product | 2.0 µl |
| 10× PCR buffer (with dNTPs/Mg$^{2+}$) | 2.0 µl |
| miRNA qPCR primers (10 µM each) | 0.3 µl |
| 20× SYBR Green I | 1.0 µl |
| Taq DNA polymerase (5 U/µl) | 0.2 µl |
| Nuclease-free water | 14.5 µl |

TABLE 6

| miRNA | Up-stream real-time PCR primer(5'→3') | |
|---|---|---|
| hsa-miR-224 | CAAGTCACTAGTGGT TCCG | (SEQ ID NO: 142) |
| hsa-miR-96 | TTTGGCACTAGCACA TTTTTG | (SEQ ID NO: 143) |
| hsa-miR-21 | TAGCTTATCAGACTG ATGTTGA | (SEQ ID NO: 144) |

TABLE 6-continued

| miRNA | Up-stream real-time PCR primer(5'→3') | |
|---|---|---|
| hsa-miR-182 | TTTGGCAATGGTAGAACTCAC | (SEQ ID NO: 145) |
| hsa-miR-183 | TATGGCACTGGTAGAATTCAC | (SEQ ID NO: 146) |
| hsa-miR-221 | AGCTACATTGTCTGCTGG | (SEQ ID NO: 147) |
| hsa-miR-497 | CAGCAGCACACTGTGG | (SEQ ID NO: 148) |
| hsa-miR-106a | AAAAGTGCTTACAGTGCAG | (SEQ ID NO: 149) |
| hsa-miR-106b | TAAAGTGCTGACAGTGCA | (SEQ ID NO: 150) |
| hsa-miR-18b | TAAGGTGCATCTAGTGCAG | (SEQ ID NO: 151) |
| hsa-miR-135b | TGTAAACATCCTCGACTGG | (SEQ ID NO: 152) |
| hsa-miR-93 | TATGGCTTTTCATTCCTATG | (SEQ ID NO: 153) |
| hsa-miR-17 | CAAAGTGCTGTTCGTGC | (SEQ ID NO: 154) |
| hsa-miR-20b | CAAAGTGCTTACAGTGCA | (SEQ ID NO: 155) |
| hsa-miR-24 | CAAAGTGCTCATAGTGC | (SEQ ID NO: 156) |
| hsa-miR-24 | TGGCTCAGTTCAGCAGG | (SEQ ID NO: 157) |
| hsa-miR-423-5p | TGAGGGGCAGAGAGC | (SEQ ID NO: 158) |
| hsa-let-7a | TGAGGTAGTAGGTTGTAT | (SEQ ID NO: 159) |

Real-time PCR was performed in a PCR thermal cycler (for example, the 7500 Real-Time PCR System, Applied Biosystems, Inc., Foster City, Calif., USA) using the following parameters:

| Step Type | Time | Temperature (° C.) |
|---|---|---|
| HOLD | 3 min | 96 |
| CYCLES | 15 s | 95 |
| CYCLES | 1 min | 60 |

40 cycles in total

The respective data were collected at 60° C. and absorption wavelength of 490 nm and an emission wavelength of 530 nm. The calculation of the Ct value for each PCR reaction and the subsequent quantification of the miRNA were performed according to the manufacturer's instructions.

Typically, at least three independent experiments were performed for each measurement and the miRNA expression level determined represents the mean value of the respective individual data obtained. The mean expression levels of the 11 miRNAs selected were normalized against the mean expression level of the stably expressed control miRNA hsa-mir-423-5p (SEQ ID NO:17) using the formula:

$\log_2([\text{miRNA expression level}]/[\text{hsa-miR-423-5p expression level}])$.

Figure 3:
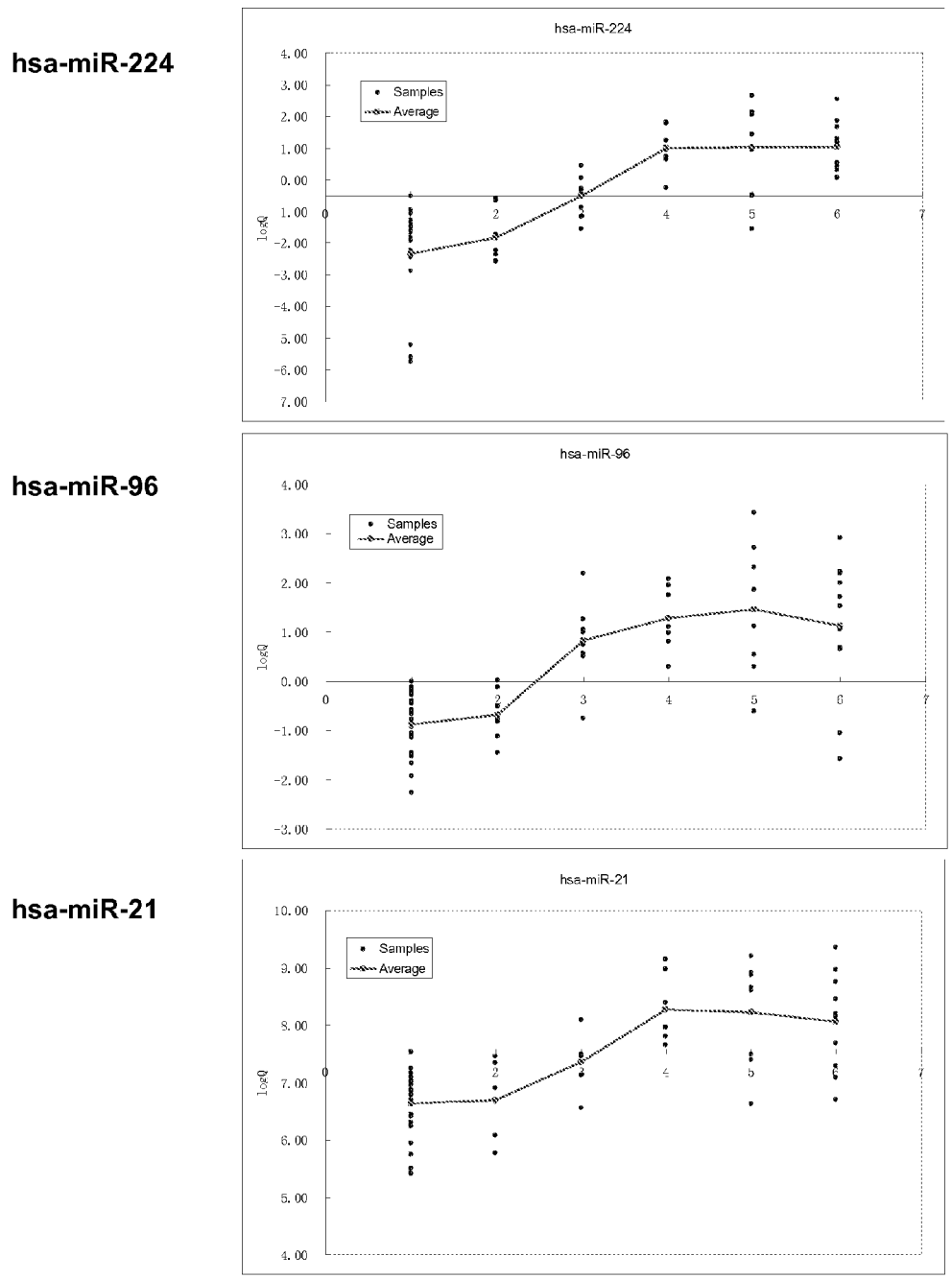
FIG. 3 depicts the respective expression levels of the 16 human miRNAs shown in FIG. 1 in different colorectal specimens. The expression levels were determined by using the methods according to the invention. Sample 1 constitutes normal (healthy) colorectal tissue, sample 2 is derived from an inflammatory adenomatous polyp, sample 3 from a tubular adenoma, and samples 4 to 6 from various adenocarcinomas classified according to the Dukes system (sample 4: Dukes A, sample 5: Dukes B, and sample 6: Dukes C). The respective data obtained were normalized against the expression level of the miRNA hsa-miR-423-5p stably expressed in all tissue samples tested.
Figure 3:
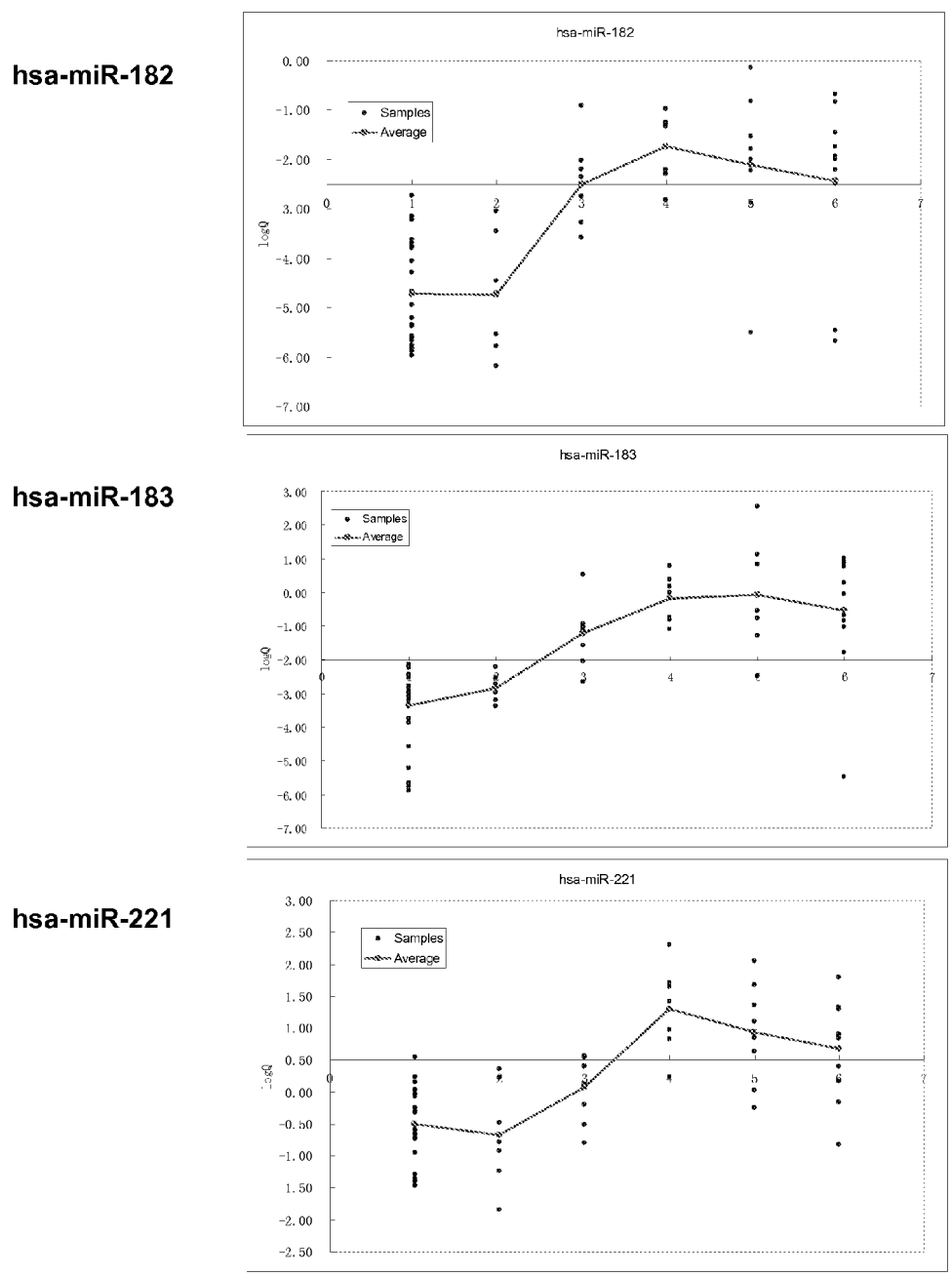
Figure 3:
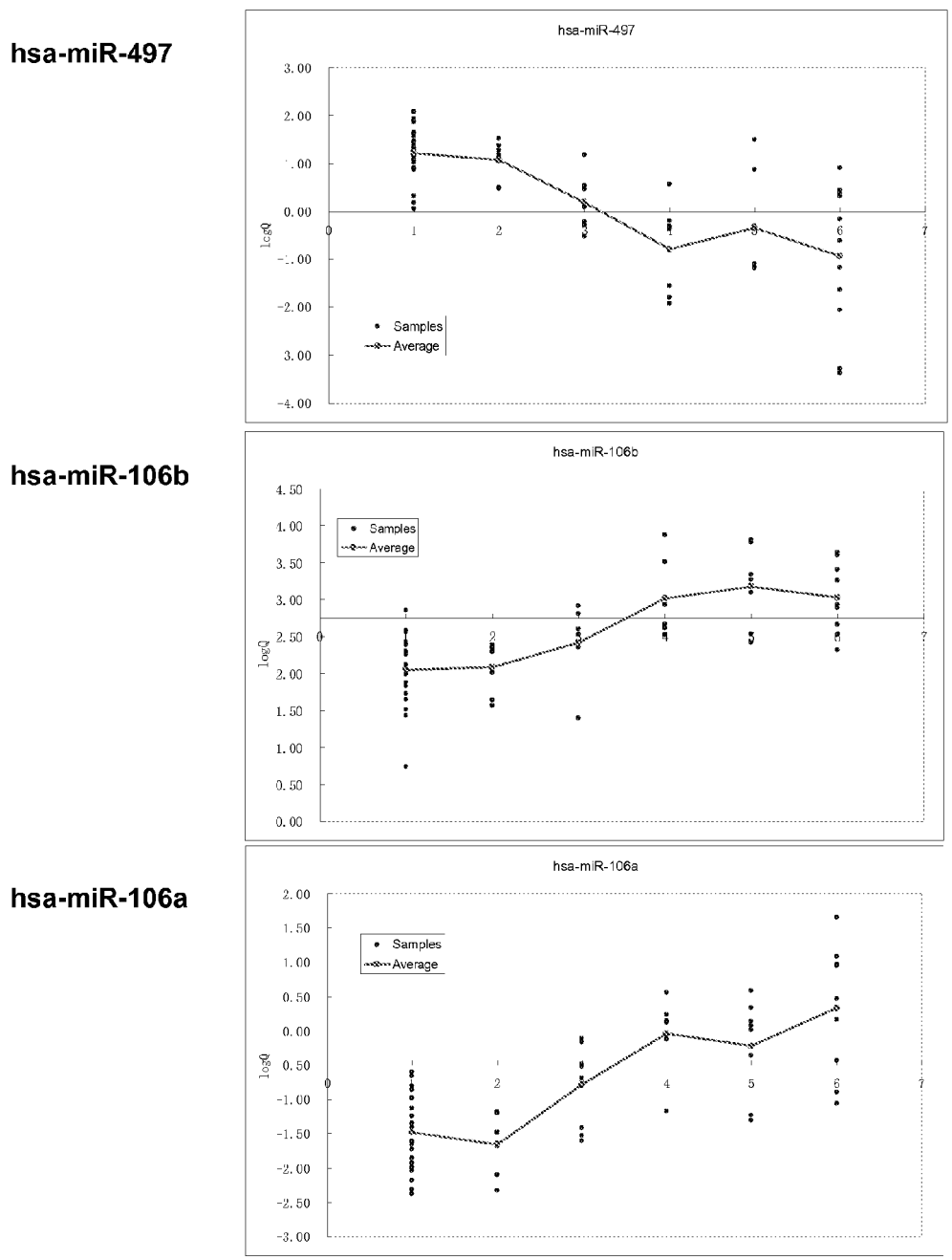
Figure 3:
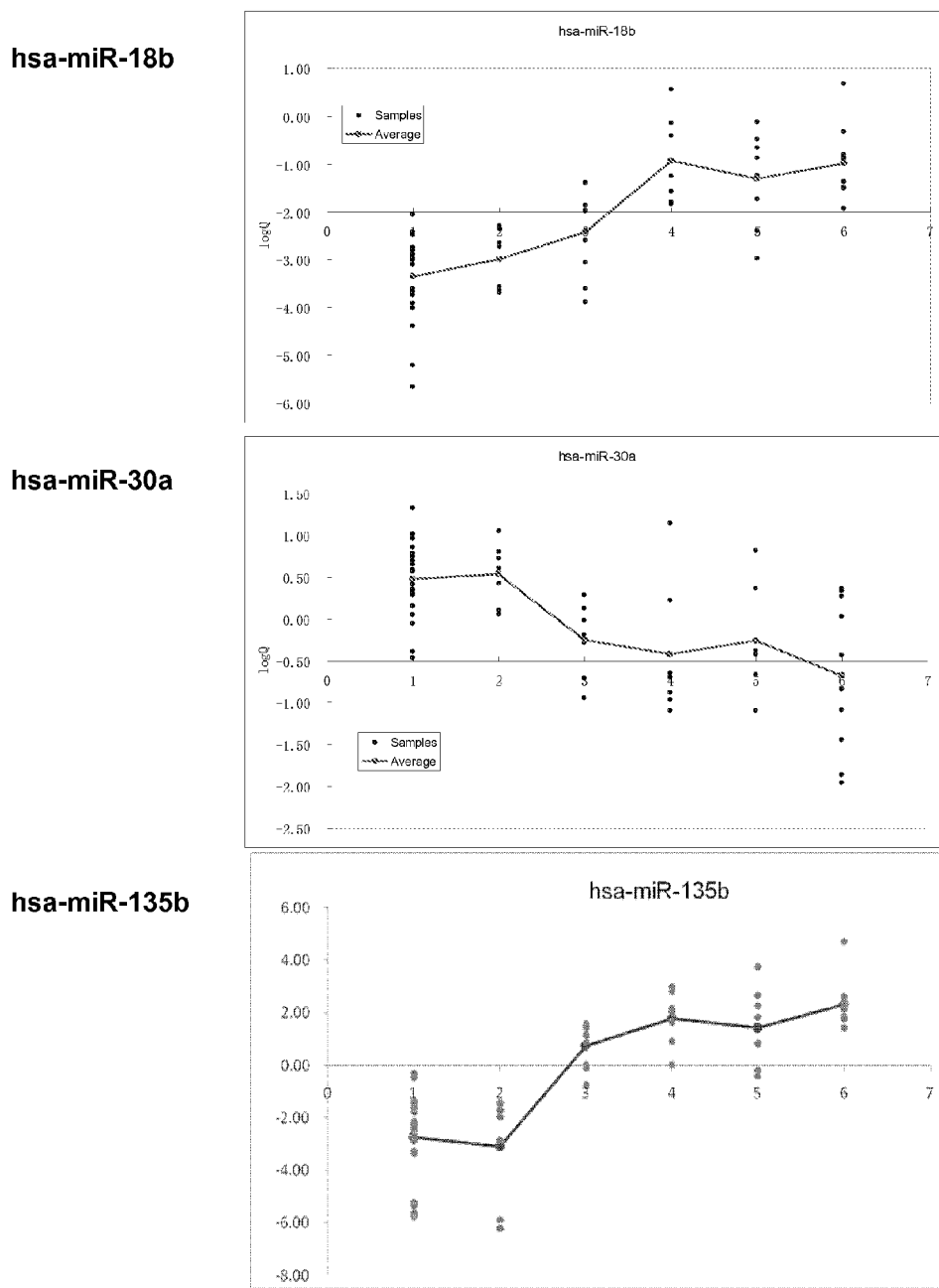
Figure 3:
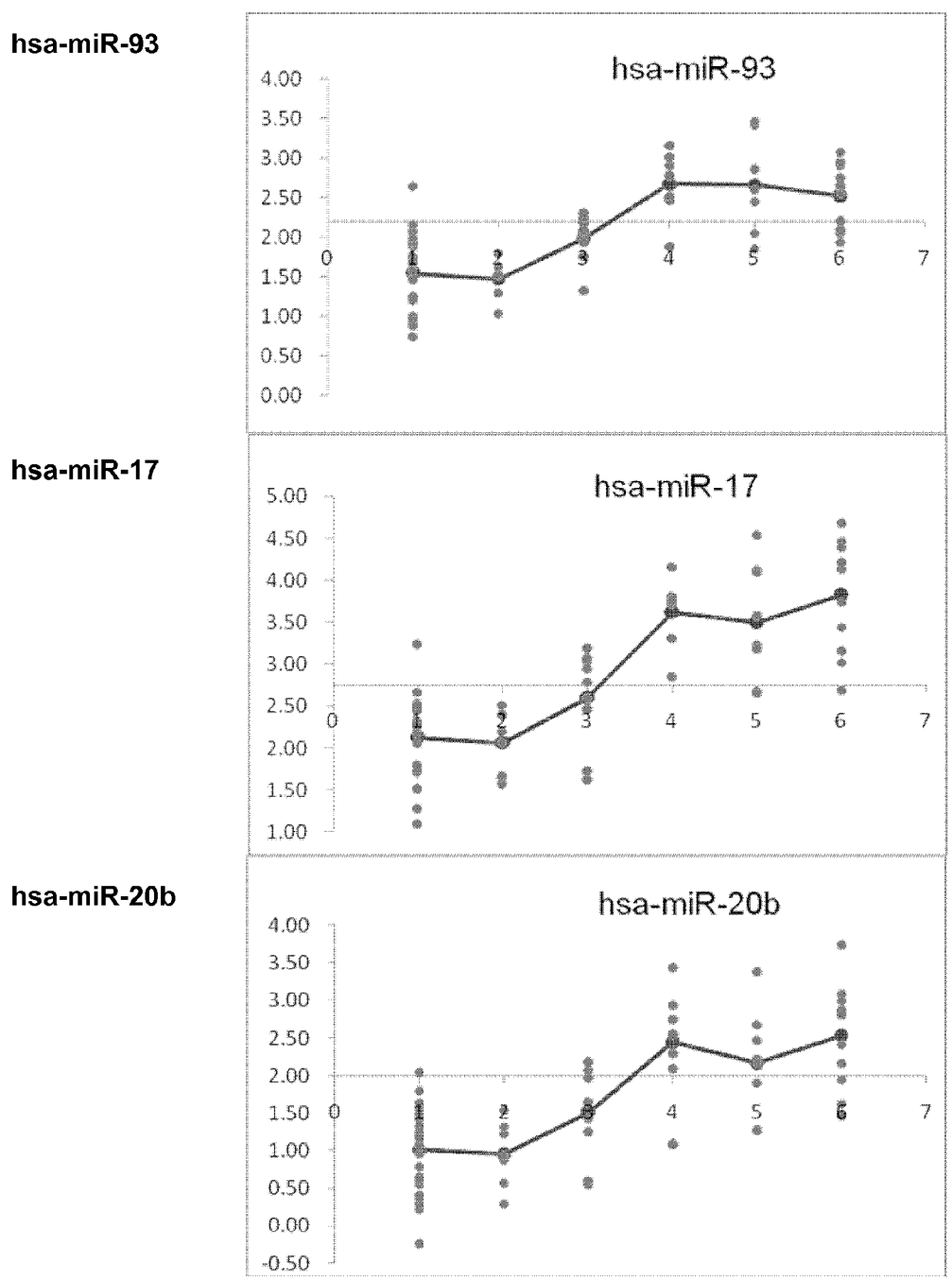
Figure 3:
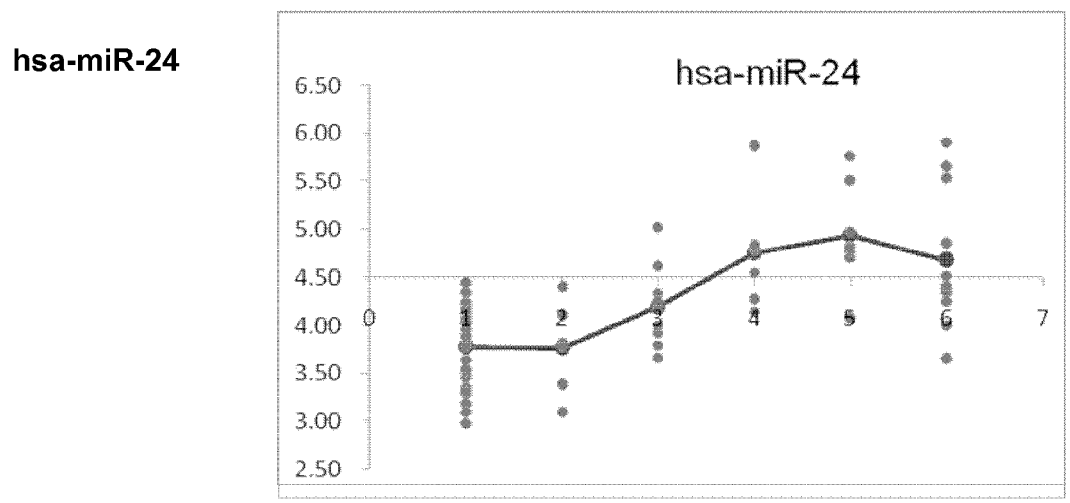

The respective expression levels of said 16 miRNAs (exemplary data) at different stages of colorectal cancer are shown in FIG. 3. The following samples were used: Sample 1 constitutes normal (healthy) colorectal tissue, sample 2 is derived from an inflammatory adenomatous polyp, sample 3 from a tubular adenoma, and samples 4 to 6 from various adenocarcinomas classified according to the Dukes system (sample 4: Dukes A, sample 5: Dukes B, and sample 6: Dukes C).

The individual circles represent the values determined in the individual experiments (samples). The curves indicate the mean expression levels in each sample. The results obtained are summarized in Table 7. The following abbreviations are used to indicate the different disease stages: CON, normal (healthy) colorectal tissue; POL, inflammatory adenomatous polyp; ADE, tubular adenoma; and ACA, adenocarcinoma. The miRNA expression values given for ACA represent the mean of the determinations obtained for the Dukes A, Dukes B, and Dukes C carcinomas analyzed (the three columns from the right in Table 7).

TABLE 7 miRNA expression at different stages of CRC

| miRNA | CON | POL | ADE | ACA | Dukes A | Dukes B | Dukes C |
|---|---|---|---|---|---|---|---|
| hsa-miR-224 | −2.41 | −1.83 | −0.52 | 0.95 | 0.98 | 1.02 | 1.01 |
| hsa-miR-96 | −0.87 | −0.68 | 0.82 | 1.18 | 1.28 | 1.46 | 1.12 |
| hsa-miR-21 | 6.70 | 6.62 | 7.35 | 8.12 | 8.27 | 8.22 | 8.06 |
| hsa-miR-182 | −4.75 | −4.73 | −2.51 | −2.22 | −1.74 | −2.11 | −2.43 |
| hsa-miR-183 | −3.39 | −2.85 | −1.23 | −0.41 | −0.19 | −0.09 | −0.55 |
| hsa-miR-221 | −0.67 | −0.55 | 0.07 | 0.91 | 1.30 | 0.93 | 0.68 |
| hsa-miR-497 | 1.19 | 1.06 | 0.20 | −0.63 | −0.80 | −0.35 | −0.94 |
| hsa-miR-106b | 2.08 | 2.05 | 2.42 | 3.03 | 3.02 | 3.18 | 3.02 |
| hsa-miR-106a | −1.51 | −1.66 | −0.78 | 0.02 | −0.04 | −0.22 | 0.33 |
| hsa-miR-18b | −3.37 | −2.99 | −2.42 | −1.14 | −0.93 | −1.32 | −0.98 |
| hsa-miR-30a | 0.46 | 0.54 | −0.25 | −0.43 | −0.42 | −0.26 | −0.68 |
| hsa-miR-135b | −2.73 | −3.07 | 0.76 | 1.92 | 1.80 | 1.44 | 2.34 |
| hsa-miR-93 | 1.55 | 1.47 | 1.99 | 2.61 | 2.67 | 2.66 | 2.53 |
| hsa-miR-17 | 2.12 | 2.06 | 2.60 | 3.67 | 3.62 | 3.51 | 3.83 |
| hsa-miR-20b | 1.01 | 0.96 | 1.52 | 2.40 | 2.44 | 2.17 | 2.54 |
| hsa-miR-24 | 3.77 | 3.77 | 4.20 | 4.78 | 4.75 | 4.93 | 4.68 |

The results obtained demonstrate that the expression of hsa-miR-224, hsa-miR-96, hsa-miR-21, hsa-miR-182, hsa-miR-183, hsa-miR-221, hsa-miR-106b, hsa-miR-106a, and hsa-miR-18b is successively up-regulated depending on the progression of the disease (CON<POL<ADE<ACA), whereas the expression of hsa-miR-497 and hsa-miR-30a is successively down-regulated depending on the progression of the disease (CON>POL>ADE>ACA).

Furthermore, the expression of hsa-miR-135b, hsa-miR-93, hsa-miR-17, hsa-miR-20b, and hsa-miR-24 is also up-regulated depending on the progression of the disease. However, the values obtained in the CON and POL samples are essentially the same (CON≈/<POL<ADE<ACA). Thus, these additional miRNAs also represent suitable diagnostic markers for discriminating non-cancerous and cancerous states.

Thus, the respective subsets of the 11 or 16 miRNAs selected for analysis together represent a unique miRNA expression signature for expression profiling of colorectal cancer that does not only allow the identification of a cancerogenous state as such but also enables the discrimination between different disease stages.

When a cut-off value is used for each miRNA for statistical data analysis (cf. Table 8), the results obtained allow not only identify CRC, particularly an adenocarcinoma, both with high sensitivity and accuracy but also to reliably discriminate the different stages in the progression of CRC.

Hence, the miRNA expression signatures defined herein do not run out in the mere identification of CRC, particularly of an adenocarcinoma, but also enable a reliably risk assessment of patients exhibiting or being supposed to have a pre-cancerous state (i.e. an inflammatory adenomatous polyp or an adenoma) whether or not the pre-cancerous state will progress in a carcinoma.

In other words, the miRNA expression signatures as defined herein enable a prediction of disease progression for patients having a predisposition to develop colorectal cancer, preferably an adenocarcinoma or a predisposition for a progression of an adenoma to an adenocarcinoma.

TABLE 8

Sensitivity/specificity of the miRNA signature

| miRNA | Cut-off | SPECIFICITY | | SENSITIVITY | | | | |
|---|---|---|---|---|---|---|---|---|
| | | CON | POL | ADE | ACA | Dukes A | Dukes B | Dukes C |
| miR-224 | >−0.5 | 100% | 100% | 66.7% | 96.2% | 100% | 87.5% | 100% |
| miR-96 | >0.25 | 100% | 100% | 88.9% | 88.5% | 100% | 87.5% | 81.8% |
| miR-21 | >7.5 | 95.7% | 100% | 11.1% | 76.9% | 100% | 62.5% | 72.7% |
| miR-182 | >−2.5 | 100% | 100% | 55.6% | 80.8% | 85.7% | 75.0% | 81.8% |
| miR-183 | >−2.0 | 100% | 100% | 77.8% | 92.3% | 100% | 87.5% | 90.9% |
| miR-221 | >0.5 | 95.7% | 100% | 22.2% | 73.1% | 85.7% | 75.0% | 63.6% |
| miR-497 | <0 | 100% | 100% | 33.3% | 73.1% | 85.7% | 75.0% | 63.6% |
| miR-106b | >2.75 | 95.7% | 100% | 22.2% | 69.2% | 57.1% | 75.0% | 72.7% |
| miR-106a | >−0.5 | 100% | 100% | 44.4% | 80.8% | 85.7% | 75.0% | 81.8% |
| miR-18b | >−2.0 | 100% | 100% | 55.6% | 92.3% | 100% | 75.0% | 100% |
| miR-30a | <−0.5 | 100% | 100% | 22.2% | 50.0% | 71.4% | 25.0% | 54.5% |
| miR-30a | >0 | 100% | 100% | 77.8% | 92.3% | 100% | 75.0% | 100% |
| miR-30a | >2.25 | 95.7% | 100% | 33.3% | 76.9% | 85.0% | 75.0% | 72.7% |
| miR-30a | >2.75 | 95.7% | 100% | 55.6% | 88.5% | 100% | 75.0% | 90.9% |
| miR-30a | >2.0 | 95.7% | 100% | 22.2% | 73.1% | 85.7% | 62.5% | 72.7% |
| miR-30a | >4.5 | 100% | 100% | 22.2% | 69.2% | 71.4% | 87.5% | 45.5% |

Figure 4:
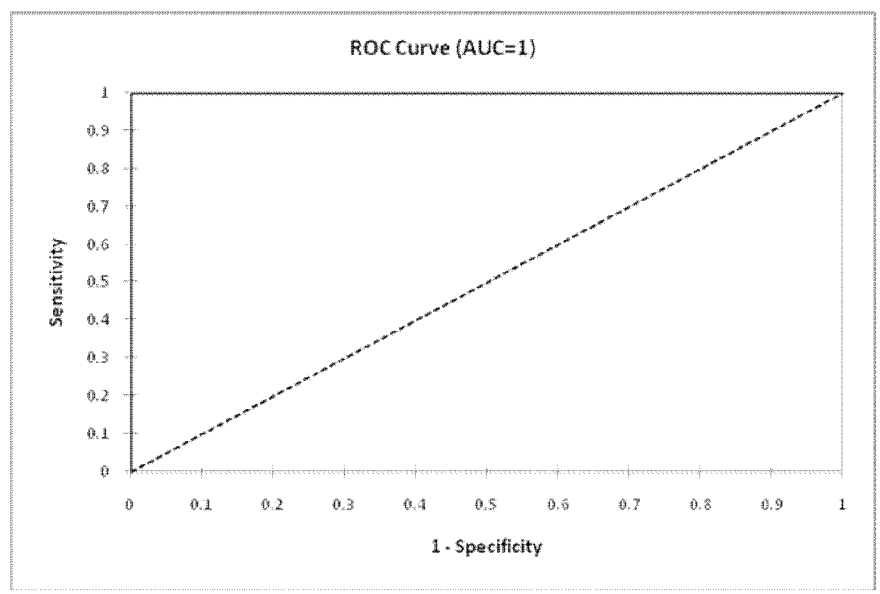
FIG. 4 depicts a receiver operating characteristic (ROC) curve for the signature of the 16 human miRNAs shown in FIG. 1. The ROC curve is based on the analysis of 138 samples—51 normal tissues/inflammatory polyps and 67 colorectal neoplasms. The area under the curve is 1, indicating a good diagnostic impact of the miRNA signature tested.

If the 16 miRNAs defined above are used together as a panel/signature (cf. Tables 9 and 10 as well as FIG. 4), this signature allows for a discrimination of adenomas/adenocarcinomas from normal tissues/inflammatory polyps with a high sensitivity and accuracy, thus emphasizing the impact of a panel of biomarkers in order to enhance the selectivity of CRC detection. Table 9 shows the multivariate analysis for the panel/signature of the 16 miRNAs as defined herein based on 138 clinical samples—51 normal tissues/inflammatory polyps (39 CON, 12 POL) and 67 colorectal neoplasms (11 ADE, 56 ACA). Table 10 depicts the cross-validation results in these samples, indicating high sensitivity and specificity of the panel in such a distinction. Again, the following abbreviations are used to indicate the different disease stages: CON, normal (healthy) colorectal tissue; POL, inflammatory adenomatous polyp; ADE, tubular adenoma; and ACA, adenocarcinoma.

TABLE 9

Multivariate analysis (Wilks' Lambda Criterion)

| Lambda | 0.159 |
|---|---|
| Probability | <0.0001 |

TABLE 10

Confusion matrix for the cross-validation results

| | ADE/ACA | CON/POL | Total | % correct |
|---|---|---|---|---|
| ADE/ACA | 67 | 0 | 67 | 100% |
| CON/POL | 2 | 49 | 51 | 96.08% |
| Total | 69 | 49 | 118 | 98.31% |

Such a risk assessment of cancer progression is of significant clinical importance in several respects. The identification of the miRNA expression signatures of the present invention provides a unique molecular marker that allows the detection of CRC at an early disease stage (that is, at a stage where the presence of malignant cells is not yet detectable by in situ techniques or microscopic analysis of biopsy or resection material), where CRC still can be efficiently treated markedly. Furthermore, the prediction of cancer progression may be used to guide the therapy decision in patients exhibiting a pre-cancerous state of CRC.

For the remaining miRNA sequences disclosed herein (SEQ ID NO:19 to SEQ ID NO:123) the respective expression data are listed in the following Table 11. In the column "ID", the abbreviation "k" denotes a known miRNA, whereas "n" denotes a newly identified miRNA. The expression levels and the degree of differential expression are listed in the columns "geometric mean" ("NOR" is normal tissue, "TUM" is tumor tissue, "F" is fold). The clinical samples were as described above: normal tissue, adenoma, adenocarcinoma Dukes A-D, and hepatic metastases.

TABLE 11

| ID | hsa-miRNA | TUMOR | T-TEST | | GEOMETRIC MEAN | | |
|---|---|---|---|---|---|---|---|
| | | | P-VAL | Q-VAL | NOR | TUM | F |
| k | hsa-miR-100 | adenoma | 0.000 | 0.017 | 36 | 16 | 0.4 |
| k | hsa-miR-148b | adenoma | 0.000 | 0.015 | 27 | 36 | 1.3 |
| k | hsa-miR-204 | adenoma | 0.000 | 0.006 | 9 | 6 | 0.6 |
| n | hsa-miR-107 | adenoma | 0.000 | 0.003 | 342 | 425 | 1.2 |
| n | hsa-miR-376c | adenoma | 0.000 | 0.006 | 25 | 14 | 0.6 |
| n | hsa-miR-625 | adenoma | 0.000 | 0.018 | 14 | 26 | 1.8 |
| n | hsa-miR-429 | adenoma | 0.000 | 0.025 | 305 | 450 | 1.5 |
| n | hsa-miR-127-3p | adenoma | 0.000 | 0.039 | 13 | 10 | 0.8 |
| n | hsa-miR-199b-3p | adenoma | 0.000 | 0.048 | 336 | 194 | 0.6 |
| n | hsa-miR-26b | Dukes A | 0.000 | 0.000 | 545 | 299 | 0.5 |
| n | hsa-miR-31* | Dukes A | 0.015 | 4.549 | 5 | 10 | 2.0 |

TABLE 11-continued

| | | | T-TEST | | GEOMETRIC MEAN | | |
|---|---|---|---|---|---|---|---|
| ID | hsa-miRNA | TUMOR | P-VAL | Q-VAL | NOR | TUM | F |
| n | hsa-miR-483-3p | Dukes A | 0.013 | 3.926 | 6 | 28 | 4.6 |
| n | hsa-miR-483-5p | Dukes A | 0.001 | 0.317 | 43 | 85 | 2.0 |
| n | hsa-miR-503 | Dukes A | 0.000 | 0.009 | 5 | 9 | 1.6 |
| n | hsa-miR-513c | Dukes A | 0.000 | 0.001 | 17 | 10 | 0.6 |
| n | hsa-miR-26a | Dukes A | 0.000 | 0.032 | 696 | 399 | 0.6 |
| n | hsa-miR-1225-5p | Dukes B | 0.002 | 0.469 | 230 | 135 | 0.6 |
| n | hsa-miR-128 | Dukes B | 0.000 | 0.020 | 16 | 24 | 1.5 |
| n | hsa-miR-134 | Dukes B | 0.005 | 1.555 | 76 | 39 | 0.5 |
| n | hsa-miR-194* | Dukes B | 0.000 | 0.003 | 14 | 10 | 0.7 |
| n | hsa-miR-29b-1* | Dukes B | 0.000 | 0.003 | 8 | 13 | 1.5 |
| n | hsa-miR-30e | Dukes B | 0.000 | 0.002 | 141 | 96 | 0.7 |
| n | hsa-miR-338-3p | Dukes B | 0.008 | 2.412 | 64 | 39 | 0.6 |
| n | hsa-miR-34b* | Dukes B | 0.000 | 0.005 | 13 | 22 | 1.8 |
| n | hsa-miR-623 | Dukes B | 0.000 | 0.012 | 17 | 11 | 0.7 |
| n | hsa-miR-662 | Dukes B | 0.000 | 0.003 | 11 | 8 | 0.7 |
| n | hsa-miR-98 | Dukes B | 0.000 | 0.002 | 22 | 38 | 1.7 |
| k | hsa-miR-99a | Dukes B | 0.004 | 1.199 | 13 | 27 | 2.0 |
| n | hsa-miR-19b-1* | Dukes B | 0.000 | 0.027 | 6 | 8 | 1.3 |
| n | hsa-miR-335 | Dukes B | 0.000 | 0.029 | 14 | 20 | 1.4 |
| n | hsa-miR-766 | Dukes B | 0.000 | 0.040 | 21 | 17 | 0.8 |
| n | hsa-miR-550* | Dukes B | 0.000 | 0.043 | 7 | 10 | 1.5 |
| n | hsa-miR-151-3p | Dukes C | 0.000 | 0.003 | 29 | 49 | 1.7 |
| n | hsa-miR-301a | Dukes C | 0.000 | 0.001 | 15 | 26 | 1.8 |
| n | hsa-miR-335* | Dukes C | 0.000 | 0.002 | 8 | 12 | 1.5 |
| n | hsa-miR-342-5p | Dukes C | 0.000 | 0.004 | 11 | 8 | 0.7 |
| n | hsa-miR-132 | Dukes D | 0.023 | 6.648 | 23 | 8 | 0.4 |
| n | hsa-miR-135a* | Dukes D | 0.002 | 0.609 | 11 | 23 | 2.0 |
| n | hsa-miR-146b-5p | Dukes D | 0.003 | 0.878 | 75 | 30 | 0.4 |
| n | hsa-miR-192* | Dukes D | 0.028 | 8.352 | 52 | 23 | 0.4 |
| n | hsa-miR-23b | Dukes D | 0.036 | 10.538 | 695 | 352 | 0.5 |
| n | hsa-miR-29c* | Dukes D | 0.002 | 0.608 | 12 | 5 | 0.4 |
| n | hsa-miR-376a | Dukes D | 0.001 | 0.320 | 16 | 7 | 0.4 |
| n | hsa-miR-486-5p | Dukes D | 0.022 | 6.394 | 12 | 5 | 0.5 |
| n | hsa-miR-196b | Dukes D | 0.012 | 3.504 | 88 | 302 | 3.4 |
| k | hsa-miR-30c | Dukes A | 0.000 | 0.007 | 177 | 98 | 0.6 |
| | | Dukes C | 0.000 | 0.015 | 173 | 115 | 0.7 |
| n | hsa-miR-768-5p | Dukes A | 0.000 | 0.109 | 112 | 48 | 0.4 |
| | | Dukes B | 0.000 | 0.000 | 126 | 63 | 0.5 |
| k | hsa-miR-125a-3p | Dukes A | 0.005 | 1.615 | 58 | 33 | 0.6 |
| | | Dukes B | 0.000 | 0.014 | 42 | 21 | 0.5 |
| | | Dukes C | 0.000 | 0.008 | 62 | 33 | 0.5 |
| k | hsa-miR-21 | adenoma | 0.000 | 0.001 | 5583 | 8820 | 1.6 |
| | | Dukes B | 0.000 | 0.000 | 5581 | 9692 | 1.7 |
| | | Dukes C | 0.000 | 0.000 | 4462 | 9173 | 2.1 |
| n | hsa-miR-24 | adenoma | 0.000 | 0.000 | 597 | 804 | 1.3 |
| | | Dukes B | 0.000 | 0.000 | 601 | 1027 | 1.7 |
| | | Dukes C | 0.000 | 0.000 | 546 | 1028 | 1.9 |
| n | hsa-miR-374a | adenoma | 0.000 | 0.043 | 76 | 120 | 1.6 |
| | | Dukes B | 0.000 | 0.034 | 65 | 104 | 1.6 |
| n | hsa-miR-21* | adenoma | 0.000 | 0.041 | 22 | 42 | 1.9 |
| | | Dukes C | 0.000 | 0.041 | 27 | 46 | 1.7 |
| k | hsa-miR-182 | adenoma | 0.000 | 0.002 | 7 | 10 | 1.4 |
| | | Dukes A | 0.000 | 0.013 | 7 | 13 | 1.9 |
| | | Dukes B | 0.000 | 0.002 | 7 | 11 | 1.6 |
| | | Dukes C | 0.000 | 0.001 | 6 | 11 | 1.8 |
| k | hsa-miR-34a | adenoma | 0.000 | 0.014 | 155 | 278 | 1.8 |
| | | Dukes B | 0.000 | 0.002 | 137 | 257 | 1.9 |
| k | hsa-miR-203 | adenoma | 0.000 | 0.000 | 73 | 182 | 2.5 |
| | | Dukes B | 0.004 | 1.204 | 69 | 124 | 1.8 |
| | | Dukes C | 0.002 | 0.539 | 54 | 121 | 2.3 |
| n | hsa-miR-23a | Dukes A | 0.000 | 0.004 | 908 | 1475 | 1.6 |
| | | Dukes B | 0.000 | 0.000 | 827 | 1522 | 1.8 |
| | | Dukes C | 0.000 | 0.000 | 747 | 1582 | 2.1 |
| k | hsa-miR-31 | Dukes A | 0.003 | 0.996 | 5 | 19 | 3.5 |
| | | Dukes B | 0.010 | 2.898 | 6 | 17 | 2.6 |
| | | Dukes C | 0.000 | 0.009 | 9 | 31 | 3.5 |
| n | hsa-miR-375 | Dukes A | 0.000 | 0.006 | 338 | 39 | 0.1 |
| | | Dukes B | 0.000 | 0.000 | 267 | 57 | 0.2 |
| | | Dukes C | 0.000 | 0.002 | 265 | 52 | 0.2 |
| n | hsa-miR-551b | Dukes A | 0.000 | 0.000 | 9 | 6 | 0.7 |
| | | Dukes B | 0.000 | 0.011 | 9 | 6 | 0.7 |
| | | Dukes C | 0.000 | 0.001 | 8 | 5 | 0.7 |

TABLE 11-continued

| ID | hsa-miRNA | TUMOR | T-TEST P-VAL | Q-VAL | GEOMETRIC MEAN NOR | TUM | F |
|---|---|---|---|---|---|---|---|
| n | hsa-miR-572 | Dukes A | 0.000 | 0.027 | 75 | 29 | 0.4 |
|  |  | Dukes B | 0.000 | 0.000 | 78 | 24 | 0.3 |
|  |  | Dukes C | 0.000 | 0.000 | 84 | 31 | 0.4 |
| n | hsa-miR-638 | Dukes A | 0.000 | 0.043 | 835 | 287 | 0.3 |
|  |  | Dukes B | 0.000 | 0.000 | 954 | 207 | 0.2 |
|  |  | Dukes C | 0.000 | 0.000 | 1102 | 304 | 0.3 |
| n | hsa-miR-650 | Dukes A | 0.000 | 0.003 | 16 | 8 | 0.5 |
|  |  | Dukes B | 0.000 | 0.001 | 16 | 8 | 0.5 |
|  |  | Dukes C | 0.000 | 0.001 | 17 | 9 | 0.5 |
| n | hsa-miR-7 | Dukes A | 0.002 | 0.562 | 49 | 109 | 2.2 |
|  |  | Dukes B | 0.000 | 0.029 | 33 | 73 | 2.2 |
|  |  | Dukes C | 0.000 | 0.020 | 34 | 71 | 2.1 |
| n | hsa-miR-801 | Dukes A | 0.000 | 0.114 | 87 | 39 | 0.4 |
|  |  | Dukes B | 0.000 | 0.000 | 78 | 26 | 0.3 |
|  |  | Dukes C | 0.000 | 0.038 | 73 | 39 | 0.5 |
| k | hsa-miR-93 | Dukes A | 0.000 | 0.013 | 89 | 163 | 1.8 |
|  |  | Dukes B | 0.000 | 0.004 | 80 | 146 | 1.8 |
|  |  | Dukes C | 0.000 | 0.000 | 84 | 173 | 2.1 |
| n | hsa-miR-939 | Dukes A | 0.001 | 0.245 | 157 | 75 | 0.5 |
|  |  | Dukes B | 0.000 | 0.002 | 146 | 51 | 0.3 |
|  |  | Dukes C | 0.000 | 0.002 | 175 | 77 | 0.4 |
| k | hsa-miR-29b | adenoma | 0.000 | 0.016 | 391 | 612 | 1.6 |
|  |  | Dukes A | 0.003 | 0.805 | 387 | 668 | 1.7 |
|  |  | Dukes B | 0.000 | 0.000 | 361 | 731 | 2.0 |
|  |  | Dukes C | 0.000 | 0.000 | 314 | 771 | 2.5 |
|  |  | hepatic metastases | 0.043 | 12.588 | 842 | 2749 | 3.3 |
| k | hsa-miR-135b | adenoma | 0.000 | 0.000 | 14 | 94 | 6.8 |
|  |  | Dukes A | 0.000 | 0.001 | 19 | 136 | 7.3 |
|  |  | Dukes B | 0.000 | 0.000 | 14 | 143 | 10.4 |
|  |  | Dukes C | 0.000 | 0.000 | 15 | 151 | 10.2 |
|  |  | Dukes D | 0.003 | 0.792 | 8 | 106 | 13.6 |
|  |  | hepatic metastases | 0.035 | 10.365 | 10 | 515 | 52.1 |
| k | hsa-miR-183 | adenoma | 0.000 | 0.003 | 11 | 27 | 2.4 |
|  |  | Dukes A | 0.000 | 0.007 | 12 | 35 | 2.8 |
|  |  | Dukes B | 0.000 | 0.000 | 11 | 33 | 2.9 |
|  |  | Dukes C | 0.000 | 0.000 | 11 | 31 | 3.0 |
|  |  | Dukes D | 0.026 | 7.772 | 10 | 30 | 3.0 |
|  |  | hepatic metastases | 0.001 | 0.224 | 13 | 56 | 4.4 |
| k | hsa-miR-195 | adenoma | 0.000 | 0.003 | 265 | 128 | 0.5 |
|  |  | Dukes A | 0.000 | 0.000 | 311 | 61 | 0.2 |
|  |  | Dukes B | 0.000 | 0.000 | 246 | 86 | 0.3 |
|  |  | Dukes C | 0.000 | 0.000 | 236 | 68 | 0.3 |
|  |  | Dukes D | 0.000 | 0.147 | 329 | 70 | 0.2 |
|  |  | hepatic metastases | 0.021 | 6.332 | 344 | 52 | 0.2 |
| k | hsa-miR-145 | adenoma | 0.000 | 0.016 | 506 | 237 | 0.5 |
|  |  | Dukes A | 0.010 | 3.023 | 446 | 200 | 0.4 |
|  |  | Dukes B | 0.000 | 0.012 | 438 | 189 | 0.4 |
|  |  | Dukes C | 0.001 | 0.395 | 530 | 254 | 0.5 |
|  |  | Dukes D | 0.002 | 0.666 | 846 | 222 | 0.3 |
|  |  | hepatic metastases | 0.013 | 3.751 | 609 | 149 | 0.2 |
| k | hsa-miR-224 | adenoma | 0.000 | 0.005 | 16 | 43 | 2.7 |
|  |  | Dukes A | 0.000 | 0.001 | 21 | 78 | 3.7 |
|  |  | Dukes B | 0.000 | 0.000 | 17 | 80 | 4.8 |
|  |  | Dukes C | 0.000 | 0.000 | 17 | 91 | 5.2 |
|  |  | Dukes D | 0.000 | 0.017 | 15 | 179 | 12.1 |
|  |  | hepatic metastases | 0.004 | 1.153 | 17 | 305 | 17.7 |
| k | hsa-miR-96 | adenoma | 0.000 | 0.000 | 35 | 110 | 3.2 |
|  |  | Dukes A | 0.000 | 0.018 | 36 | 110 | 3.1 |
|  |  | Dukes B | 0.000 | 0.000 | 34 | 118 | 3.5 |
|  |  | Dukes C | 0.000 | 0.002 | 30 | 99 | 3.3 |
|  |  | Dukes D | 0.003 | 0.952 | 28 | 82 | 2.9 |
|  |  | hepatic metastases | 0.002 | 0.636 | 48 | 199 | 4.1 |
| n | hsa-miR-27a | adenoma | 0.000 | 0.016 | 389 | 626 | 1.6 |
|  |  | Dukes B | 0.000 | 0.000 | 380 | 697 | 1.8 |
|  |  | Dukes C | 0.000 | 0.000 | 317 | 717 | 2.3 |
|  |  | hepatic metastases | 0.034 | 10.134 | 425 | 977 | 2.3 |
| k | hsa-miR-342-3p | Dukes A | 0.000 | 0.118 | 131 | 67 | 0.5 |
|  |  | Dukes C | 0.000 | 0.017 | 143 | 74 | 0.5 |
|  |  | Dukes D | 0.060 | 17.601 | 148 | 68 | 0.5 |
|  |  | hepatic metastases | 0.014 | 4.029 | 137 | 53 | 0.4 |
| n | hsa-miR-30e* | Dukes A | 0.000 | 0.000 | 24 | 13 | 0.5 |
|  |  | Dukes D | 0.033 | 9.719 | 19 | 8 | 0.4 |
|  |  | hepatic metastases | 0.018 | 5.291 | 26 | 11 | 0.4 |
| n | hsa-miR-29c | Dukes A | 0.000 | 0.002 | 620 | 299 | 0.5 |
|  |  | Dukes C | 0.000 | 0.000 | 554 | 358 | 0.6 |
|  |  | Dukes D | 0.004 | 1.178 | 550 | 230 | 0.4 |

TABLE 11-continued

| ID | hsa-miRNA | TUMOR | T-TEST P-VAL | T-TEST Q-VAL | GEOMETRIC MEAN NOR | GEOMETRIC MEAN TUM | GEOMETRIC MEAN F |
|---|---|---|---|---|---|---|---|
| n | hsa-miR-150 | Dukes A | 0.007 | 1.960 | 127 | 49 | 0.4 |
| | | Dukes B | 0.000 | 0.082 | 116 | 55 | 0.5 |
| | | Dukes C | 0.000 | 0.000 | 155 | 38 | 0.2 |
| | | Dukes D | 0.017 | 4.937 | 125 | 29 | 0.2 |
| k | hsa-miR-18a | Dukes A | 0.000 | 0.007 | 20 | 60 | 3.1 |
| | | Dukes B | 0.000 | 0.001 | 18 | 50 | 2.7 |
| | | Dukes C | 0.000 | 0.000 | 17 | 55 | 3.2 |
| | | Dukes D | 0.026 | 7.625 | 15 | 37 | 2.5 |
| n | hsa-miR-181c | Dukes B | 0.000 | 0.009 | 11 | 18 | 1.7 |
| | | Dukes D | 0.005 | 1.572 | 6 | 13 | 2.2 |
| n | hsa-miR-592 | Dukes B | 0.001 | 0.262 | 7 | 15 | 2.1 |
| | | Dukes D | 0.011 | 3.341 | 6 | 22 | 3.9 |
| k | hsa-miR-106b | Dukes B | 0.000 | 0.000 | 155 | 278 | 1.8 |
| | | Dukes C | 0.000 | 0.000 | 140 | 303 | 2.2 |
| n | hsa-miR-139-5p | Dukes B | 0.000 | 0.002 | 9 | 7 | 0.7 |
| | | Dukes C | 0.000 | 0.000 | 10 | 6 | 0.6 |
| k | hsa-miR-192 | Dukes B | 0.000 | 0.000 | 3730 | 1775 | 0.5 |
| | | Dukes C | 0.000 | 0.000 | 3286 | 1569 | 0.5 |
| k | hsa-miR-194 | Dukes B | 0.000 | 0.000 | 1774 | 909 | 0.5 |
| | | Dukes C | 0.000 | 0.005 | 1686 | 1033 | 0.6 |
| n | hsa-miR-374b | Dukes B | 0.000 | 0.005 | 42 | 73 | 1.7 |
| | | Dukes C | 0.002 | 0.473 | 42 | 64 | 1.5 |
| k | hsa-miR-95 | Dukes B | 0.000 | 0.004 | 18 | 36 | 2.0 |
| | | Dukes C | 0.000 | 0.036 | 18 | 35 | 2.0 |
| k | hsa-miR-25 | Dukes B | 0.000 | 0.017 | 97 | 171 | 1.8 |
| | | Dukes C | 0.001 | 0.188 | 97 | 171 | 1.8 |
| | | Dukes D | 0.023 | 6.911 | 157 | 308 | 2.0 |
| k | hsa-miR-19b | Dukes C | 0.000 | 0.000 | 446 | 920 | 2.1 |
| | | Dukes D | 0.005 | 1.349 | 499 | 1090 | 2.2 |
| k | hsa-miR-10b | Dukes C | 0.000 | 0.017 | 152 | 78 | 0.5 |
| | | hepatic metastases | 0.026 | 7.775 | 347 | 61 | 0.2 |
| n | hsa-miR-451 | Dukes C | 0.011 | 3.261 | 315 | 163 | 0.5 |
| | | Dukes D | 0.049 | 14.483 | 916 | 196 | 0.2 |
| | | hepatic metastases | 0.020 | 5.897 | 623 | 97 | 0.2 |
| k | hsa-miR-143 | Dukes D | 0.020 | 5.773 | 132 | 32 | 0.2 |
| | | hepatic metastases | 0.010 | 3.009 | 101 | 30 | 0.3 |
| n | hsa-miR-145* | Dukes D | 0.005 | 1.573 | 23 | 6 | 0.3 |
| | | hepatic metastases | 0.029 | 8.575 | 19 | 5 | 0.3 |
| n | hsa-miR-22 | Dukes D | 0.008 | 2.303 | 914 | 503 | 0.6 |
| | | hepatic metastases | 0.014 | 4.186 | 979 | 412 | 0.4 |
| k | hsa-miR-222 | Dukes D | 0.007 | 2.174 | 14 | 28 | 2.0 |
| | | hepatic metastases | 0.004 | 1.155 | 13 | 48 | 3.6 |
| n | hsa-miR-122 | hepatic metastases | 0.007 | 2.009 | 5 | 83 | 16.6 |
| n | hsa-miR-199b-5p | hepatic metastases | 0.018 | 5.409 | 63 | 14 | 0.2 |
| n | hsa-miR-365 | hepatic metastases | 0.004 | 1.125 | 66 | 177 | 2.7 |
| n | hsa-miR-660 | hepatic metastases | 0.049 | 14.597 | 37 | 84 | 2.3 |
| k | hsa-miR-106a | Dukes A | 0.000 | 0.026 | 15 | 31 | 2.0 |
| | | Dukes B | 0.000 | 0.000 | 13 | 27 | 2.1 |
| | | Dukes C | 0.000 | 0.000 | 15 | 37 | 2.5 |
| | | Dukes D | 0.019 | 5.558 | 8 | 21 | 2.6 |
| | | hepatic metastases | 0.007 | 1.939 | 11 | 37 | 3.5 |
| k | hsa-miR-18b | Dukes A | 0.000 | 0.067 | 9 | 18 | 2.1 |
| | | Dukes B | 0.000 | 0.000 | 9 | 16 | 1.7 |
| | | Dukes C | 0.000 | 0.000 | 8 | 15 | 1.8 |
| | | Dukes D | 0.033 | 9.659 | 7 | 18 | 2.4 |
| | | hepatic metastases | 0.048 | 14.170 | 10 | 23 | 2.4 |
| k | hsa-miR-19a | Dukes A | 0.017 | 5.136 | 187 | 318 | 1.7 |
| | | Dukes B | 0.000 | 0.049 | 183 | 329 | 1.8 |
| | | Dukes C | 0.000 | 0.001 | 161 | 351 | 2.2 |
| | | Dukes D | 0.001 | 0.429 | 161 | 412 | 2.6 |
| | | hepatic metastases | 0.012 | 3.403 | 215 | 420 | 2.0 |
| n | hsa-miR-20b | Dukes A | 0.000 | 0.023 | 63 | 135 | 2.2 |
| | | Dukes B | 0.000 | 0.000 | 54 | 130 | 2.4 |
| | | Dukes C | 0.000 | 0.000 | 54 | 150 | 2.8 |
| | | Dukes D | 0.001 | 0.240 | 68 | 188 | 2.8 |
| | | hepatic metastases | 0.001 | 0.153 | 99 | 318 | 3.2 |
| n | hsa-miR-424 | Dukes A | 0.000 | 0.048 | 30 | 91 | 3.0 |
| | | Dukes B | 0.000 | 0.002 | 31 | 80 | 2.6 |
| | | Dukes C | 0.000 | 0.001 | 24 | 68 | 2.8 |
| | | Dukes D | 0.048 | 14.279 | 37 | 191 | 5.2 |
| | | hepatic metastases | 0.104 | 30.746 | 45 | 350 | 7.8 |
| n | hsa-miR-552 | Dukes A | 0.001 | 0.392 | 9 | 24 | 2.6 |
| | | Dukes B | 0.000 | 0.006 | 10 | 27 | 2.8 |
| | | Dukes C | 0.000 | 0.000 | 8 | 28 | 3.4 |
| | | Dukes D | 0.035 | 10.264 | 9 | 46 | 5.1 |
| | | hepatic metastases | 0.023 | 6.662 | 12 | 90 | 7.5 |

TABLE 11-continued

| ID | hsa-miRNA | TUMOR | T-TEST P-VAL | T-TEST Q-VAL | GEOMETRIC MEAN NOR | GEOMETRIC MEAN TUM | GEOMETRIC MEAN F |
|---|---|---|---|---|---|---|---|
| k | hsa-miR-92a | Dukes A | 0.000 | 0.099 | 244 | 487 | 2.0 |
| | | Dukes B | 0.000 | 0.007 | 235 | 478 | 2.0 |
| | | Dukes C | 0.000 | 0.000 | 234 | 595 | 2.5 |
| | | Dukes D | 0.000 | 0.095 | 275 | 1129 | 4.1 |
| | | hepatic metastases | 0.003 | 0.984 | 288 | 859 | 3.0 |
| k | hsa-miR-1 | Dukes A | 0.000 | 0.013 | 37 | 12 | 0.3 |
| | | Dukes B | 0.000 | 0.000 | 29 | 11 | 0.4 |
| | | Dukes C | 0.000 | 0.001 | 26 | 11 | 0.4 |
| | | Dukes D | 0.004 | 1.078 | 81 | 8 | 0.1 |
| | | hepatic metastases | 0.014 | 4.049 | 66 | 7 | 0.1 |
| k | hsa-miR-133b | Dukes A | 0.000 | 0.016 | 30 | 12 | 0.4 |
| | | Dukes B | 0.000 | 0.000 | 26 | 11 | 0.4 |
| | | Dukes C | 0.000 | 0.001 | 28 | 11 | 0.4 |
| | | Dukes D | 0.014 | 4.155 | 47 | 6 | 0.1 |
| | | hepatic metastases | 0.012 | 3.603 | 28 | 5 | 0.2 |
| k | hsa-miR-17 | Dukes A | 0.000 | 0.001 | 125 | 321 | 2.6 |
| | | Dukes B | 0.000 | 0.000 | 113 | 289 | 2.6 |
| | | Dukes C | 0.000 | 0.000 | 113 | 364 | 3.2 |
| | | Dukes D | 0.002 | 0.703 | 166 | 484 | 2.9 |
| | | hepatic metastases | 0.002 | 0.487 | 256 | 624 | 2.4 |
| k | hsa-miR-20a | Dukes A | 0.000 | 0.003 | 355 | 839 | 2.4 |
| | | Dukes B | 0.000 | 0.001 | 359 | 840 | 2.3 |
| | | Dukes C | 0.000 | 0.000 | 349 | 1015 | 2.9 |
| | | Dukes D | 0.001 | 0.198 | 364 | 1099 | 3.0 |
| | | hepatic metastases | 0.016 | 4.592 | 591 | 1468 | 2.5 |
| n | hsa-miR-221 | Dukes A | 0.000 | 0.001 | 34 | 80 | 2.4 |
| | | Dukes B | 0.000 | 0.001 | 28 | 62 | 2.2 |
| | | Dukes C | 0.000 | 0.000 | 28 | 66 | 2.3 |
| | | Dukes D | 0.001 | 0.426 | 34 | 98 | 2.9 |
| | | hepatic metastases | 0.011 | 3.252 | 37 | 149 | 4.0 |
| k | hsa-miR-30a | Dukes A | 0.000 | 0.014 | 55 | 26 | 0.5 |
| | | Dukes B | 0.000 | 0.003 | 51 | 30 | 0.6 |
| | | Dukes C | 0.000 | 0.010 | 52 | 29 | 0.6 |
| | | Dukes D | 0.000 | 0.015 | 57 | 23 | 0.4 |
| | | hepatic metastases | 0.015 | 4.515 | 53 | 32 | 0.6 |
| k | hsa-miR-378 | Dukes A | 0.000 | 0.002 | 108 | 42 | 0.4 |
| | | Dukes B | 0.000 | 0.000 | 104 | 44 | 0.4 |
| | | Dukes C | 0.000 | 0.001 | 104 | 40 | 0.4 |
| | | Dukes D | 0.009 | 2.736 | 125 | 44 | 0.4 |
| | | hepatic metastases | 0.066 | 19.340 | 132 | 29 | 0.2 |
| n | hsa-miR-378* | Dukes A | 0.000 | 0.001 | 26 | 12 | 0.5 |
| | | Dukes B | 0.000 | 0.000 | 27 | 14 | 0.5 |
| | | Dukes C | 0.000 | 0.000 | 25 | 12 | 0.5 |
| | | Dukes D | 0.002 | 0.687 | 24 | 8 | 0.3 |
| | | hepatic metastases | 0.003 | 0.929 | 26 | 5 | 0.2 |
| k | hsa-miR-497 | Dukes A | 0.000 | 0.000 | 102 | 25 | 0.2 |
| | | Dukes B | 0.000 | 0.000 | 90 | 34 | 0.4 |
| | | Dukes C | 0.000 | 0.000 | 81 | 27 | 0.3 |
| | | Dukes D | 0.005 | 1.501 | 138 | 34 | 0.2 |
| | | hepatic metastases | 0.031 | 9.019 | 160 | 23 | 0.1 |
| n | hsa-miR-452 | Dukes B | 0.000 | 0.011 | 8 | 14 | 1.6 |
| | | Dukes D | 0.049 | 14.567 | 5 | 13 | 2.5 |
| | | hepatic metastases | 0.043 | 12.776 | 5 | 20 | 4.1 |
| k | hsa-miR-139-3p | Dukes B | 0.000 | 0.000 | 19 | 11 | 0.6 |
| | | Dukes C | 0.000 | 0.000 | 18 | 11 | 0.6 |
| | | hepatic metastases | 0.046 | 13.500 | 23 | 7 | 0.3 |
| k | hsa-miR-29a | Dukes B | 0.000 | 0.006 | 839 | 1525 | 1.8 |
| | | Dukes C | 0.000 | 0.000 | 816 | 1623 | 2.0 |
| | | hepatic metastases | 0.046 | 13.684 | 1244 | 3302 | 2.7 |
| n | hsa-miR-455-3p | Dukes B | 0.000 | 0.002 | 20 | 46 | 2.3 |
| | | Dukes C | 0.000 | 0.036 | 21 | 41 | 2.0 |
| | | hepatic metastases | 0.036 | 10.700 | 13 | 47 | 3.5 |
| k | hsa-miR-130b | Dukes B | 0.000 | 0.001 | 30 | 59 | 2.0 |
| | | Dukes C | 0.000 | 0.022 | 27 | 48 | 1.8 |
| | | Dukes D | 0.006 | 1.715 | 30 | 63 | 2.1 |
| | | hepatic metastases | 0.008 | 2.346 | 36 | 76 | 2.1 |
| n | hsa-miR-17* | Dukes B | 0.000 | 0.000 | 12 | 23 | 1.9 |
| | | Dukes C | 0.000 | 0.000 | 12 | 23 | 1.9 |
| | | Dukes D | 0.012 | 3.624 | 7 | 20 | 2.9 |
| | | hepatic metastases | 0.020 | 6.006 | 8 | 38 | 4.8 |

TABLE 11-continued

| ID | hsa-miRNA | TUMOR | T-TEST | | GEOMETRIC MEAN | | |
| --- | --- | --- | --- | --- | --- | --- | --- |
| | | | P-VAL | Q-VAL | NOR | TUM | F |
| n | hsa-miR-20a* | Dukes B | 0.000 | 0.002 | 8 | 14 | 1.7 |
| | | Dukes C | 0.000 | 0.000 | 8 | 14 | 1.6 |
| | | Dukes D | 0.023 | 6.928 | 5 | 11 | 2.2 |
| | | hepatic metastases | 0.001 | 0.173 | 5 | 21 | 4.1 |
| k | hsa-miR-215 | Dukes B | 0.000 | 0.000 | 1781 | 779 | 0.4 |
| | | Dukes C | 0.000 | 0.000 | 1492 | 744 | 0.5 |
| | | Dukes D | 0.001 | 0.426 | 1936 | 761 | 0.4 |
| | | hepatic metastases | 0.050 | 14.809 | 2250 | 849 | 0.4 |

Example 3

Sample Collection and Preparation

Figure 6:
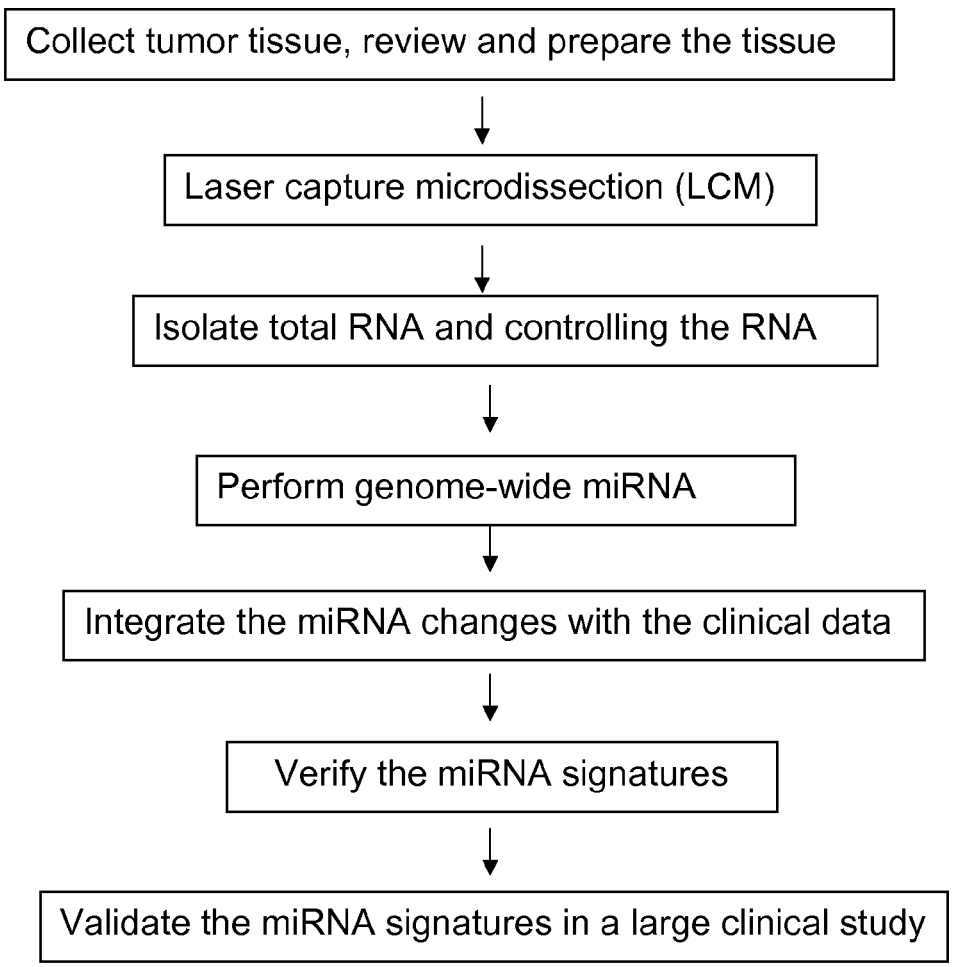
FIG. 6 depicts another flow chart schematically illustrating the essential method steps for determining an expression signature according to the present invention for identifying one or more target cells exhibiting or having a predisposition to develop hepatocellular cancer.
Figure 7:
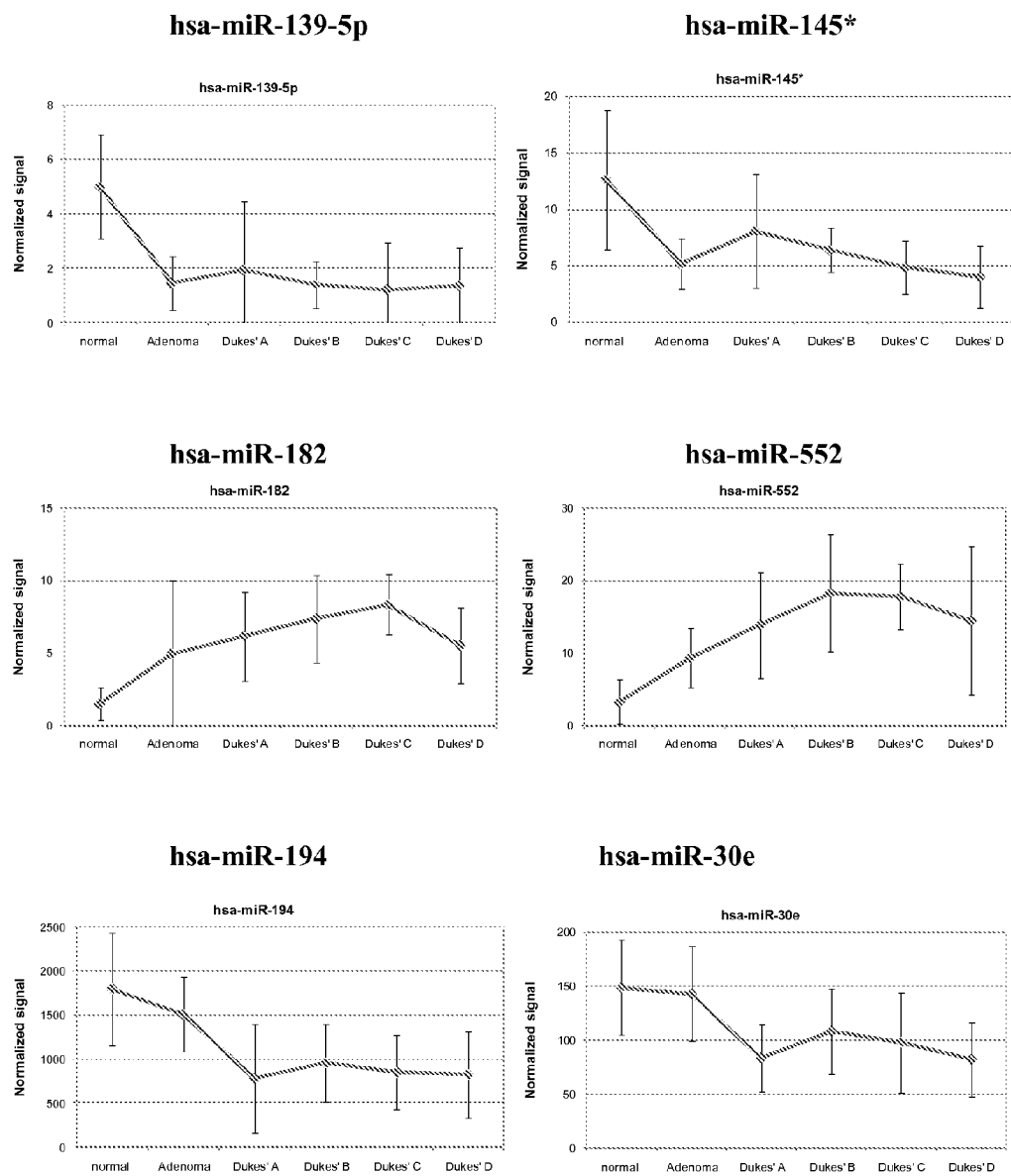
FIG. 7 depicts the respective expression levels of the 12 identified miRNAs in the transformation and progression of colorectal cancer. Potential clinical values are 1) Pre-cancer (adenoma) detection, 2) Early cancer (carcinoma) detection, 3) CRC risk assessment in patients with adenomas. Additionally, they are potential targets for drug development at the pre-cancer and early stages of CRC.
Figure 7:
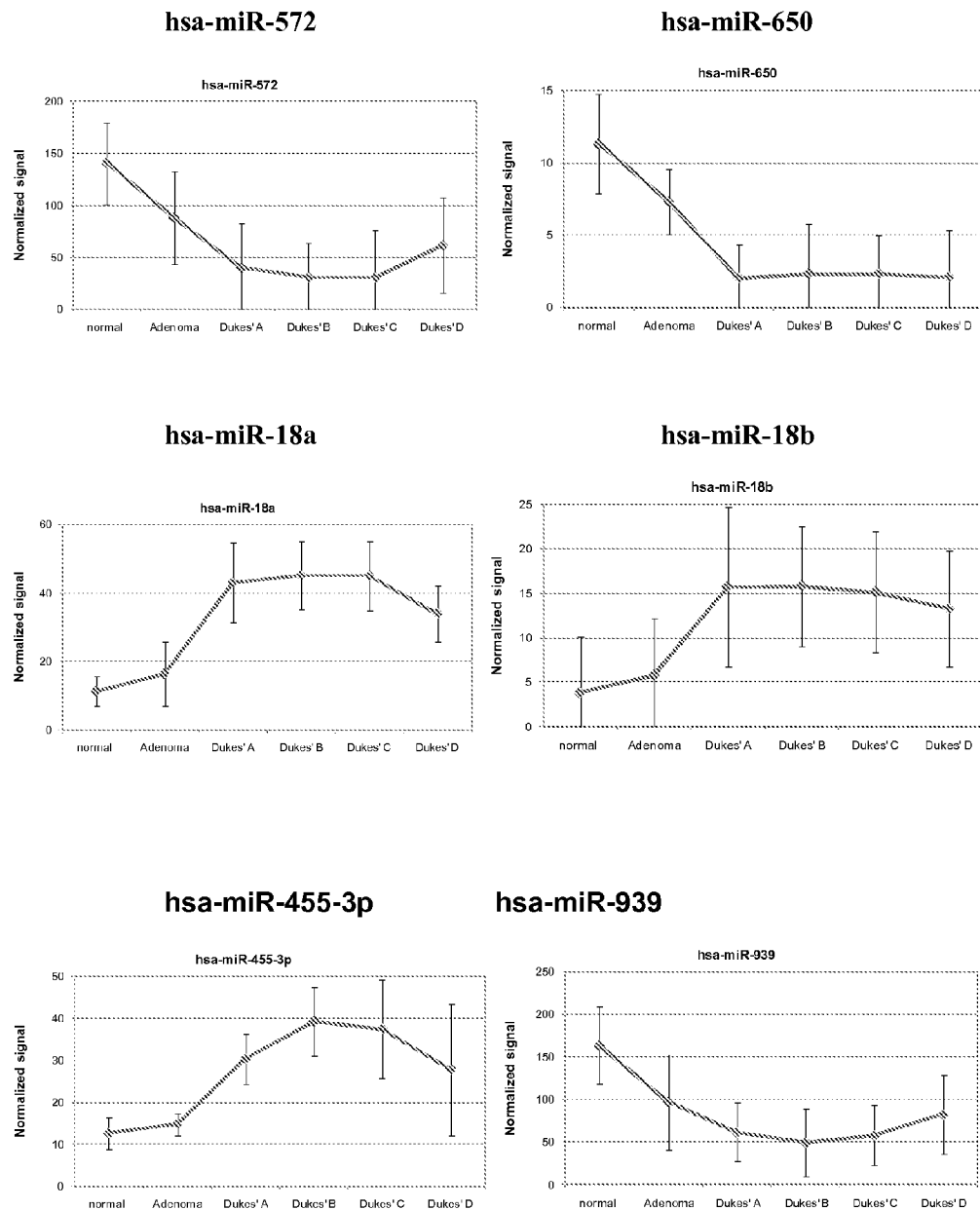

The principal method steps for identifying one or more target cells in a patient's sample exhibiting or having a predisposition to develop colorectal cancer are shown in FIG. 6.

225 tissue specimens from colorectal cancer patients were surgically resected. The tissues were procured immediately after surgery, embedded in optimum cutting temperature (OCT) compound, fast-frozen in liquid nitrogen and stored at −80° C. Baseline characteristics of the tumour specimens for the discovery and validation studies are shown in Table 12. Matched normal colorectal tissues (at least 10 cm from tumor loci), inflammatory polyps and adenomas were from the same patients who had carcinomas.

TABLE 12

Baseline characteristics of the tumour specimens

| Colorectal specimens | Discovery | Validation |
| --- | --- | --- |
| Control tissues | | |
| Normal | 40 | 34 |
| Inflammatory polyp | 10 | 8 |
| Adenoma | 15 | 13 |
| Carcinoma | | |
| Dukes' A | 12 | 8 |
| Dukes' B | 12 | 9 |
| Dukes' C | 16 | 15 |
| Dukes' D | 17 | 16 |
| No. of tissue specimens | 122 | 103 |

Patient data (age, sex, imaging data, therapy, other medical conditions, family history, and the like) were derived from the hospital databases for matching the various samples collected. Pathologic follow-up (for example, histological analysis via hematoxylin and eosin (H&E) staining) was used for evidently determining the disease state (i.e. healthy control, adenoma, adenocarcinoma or intermediate state) of a given sample as well as to ensure a consistent classification of the specimens.

Laser-capture micro-dissection was optionally performed for each cancerous sample in order to specifically isolate tumor cell populations (about 200.000 cells). In brief, a transparent transfer film is applied to the surface of a tissue section or specimen. Under a microscope, the thin tissue section is viewed through the glass slide on which it is mounted and clusters of cells are identified for isolation. When the cells of choice are in the center of the field of view, a near IR laser diode integral with the microscope optics is activated. The pulsed laser beam activates a spot on the transfer film, fusing the film with the underlying cells of choice. The transfer film with the bonded cells is then lifted off the thin tissue section (reviewed, e.g., in Emmert-Buck, M. R. et al. (1996). *Science* 274, 998-1001; Espina, V. et al. (2007) *Expert Rev. Mol. Diagn.* 7, 647-657).

The preparation of the cryostat sections and the capturing step using a laser capture microspope (Arcturus Veritas™ Laser Capture Microdissection Instrument (Molecular Devices, Inc., Sunnyvale, Calif., USA) were performed essentially according to the instructions of the manufacturer.

Total RNA was extracted from the tissue sections by using mirVana miRNA isolation kit according to the instructions from the manufacturer (Ambion, Austin, Tex.). The concentration was quantified by NanoDrop 1000 Spectrophotometer (NanoDrop Technologies, Waltham, Mass.). The quality control of RNA was performed by a 2100 Bioanalyzer using the RNA 6000 Pico LabChip kit (Agilent Technologies, Santa Clara, Calif.).

Example 4

Genome-Wide miRNA Analysis in the Samples

A qualitative analysis of the miRNAs (differentially) expressed in a particular sample may optionally be performed using the Agilent miRNA microarray platform (Agilent Technologies, Santa Clara, Calif., USA). The microarray contains probes for 723 human miRNAs from the Sanger database v.10.1. Total RNA (100 ng) derived from each of 225 LCM-selected colorectal samples were used as inputs for labeling via Cy3 incorporation. Microarray slides were scanned by XDR Scan (PMT100, PMT5). The labeling and hybridization were performed according to the protocols in the Agilent miRNA microarray system.

Example 5

Data Analysis of the Microarray Data

The raw data obtained for single-color (CY3) hybridization were normalized by applying a Quantile method and using GeneSpring GX10 software (Agilent Technologies, Santa Clara, Calif., USA) known in the art. Of the 723 miRNAs in the Agilent miRNA microarray, 285 miRNAs were selected as positive signals for all subsequent analysis Differential miRNA Expression Analysis.

Unpaired t-test after Fisher test (F-test) was used to identify basic miRNA signatures between control tissues vs. adenoma or carcinomas, respectively. The fold changes of miRNA expression levels between control tissues and tumor samples were calculated from the normalized values.

For the specificity and sensitivity of the individual miRNA as diagnostic biomarkers, MedCalc software was used to perform receiver operating characteristic (ROC) curve analysis of the individual miRNA in the control tissues vs. adenoma or control tissues vs. carcinomas, respectively. 95% confidence interval was used to determine the significance.

For assessing whether a particular miRNA is differentially expressed in cancerogenous target cells as compared to healthy control cells the following criteria were used:
(i) p-value (probability value) of <0.01 in both discovery and validation studies
(ii) AUC (accuracy as a diagnostic biomarker) AUC of >0.700 in both discovery and validation studies In case, the two criteria were fulfilled, the miRNA was considered to be differentially expressed in the target and control cells, respectively.

Disease State Progression Analysis:

for each neighboring transition along the stages of CRC, normal tissue to adenoma, adenoma to Duke's A/B Carcinoma and Duke's A/B to Duke's C/D carcinoma, the changes in the miRNA expression levels were estimated using two-sample t-tests along with multiple testing Bonferroni-Hochberg correction (Benjamini et al. (1995) *J. Royal Statistical Society Series B-Methodological.* 57, 289-300), with a false discovery rate chosen at 0.05.

Classification/Prediction Analysis:

three supervised classification algorithms (prediction analysis of microarray, genetic algorithm-SVM and one-loop Naïve Bayesian) were employed to predict colorectal adenoma and adenocarcinoma from the two datasets acquired on microarrays for the discovery and validation studies. Cross-validation methods were all utilized in all these machine learning processes.

Prediction Analysis of Microarray (Tibshirani et al. (2002). *Proc. Natl. Acad. Sci. USA.* 99, 6567-6572; http://www-stat.stanford.edui~tibs/PAM) was performed by using Nearest Shrunken Centroids algorithm with default parameters. In training data set from the discovery study, a 10-fold cross-validation was utilized to calculate the overall prediction accuracy and to find the minimal set of miRNAs as predictors. The miRNA predictors derived from training data set were then tested on the independent test dataset from the validation study. The reproducibility of the identified miRNA classifiers was assessed in this step.

One-loop Naïve Bayesian was performed according to the protocol previously described (Wessels et al. (2006) *Bioinformatics.* 21, 3755-3762) with minor modifications (parameter settings, choice of filtering criterion and classifier). The feature ranking was based on Pearson correlation to the outcome. The optimization of the number of features was used by calculating the balanced accuracy over a 10-fold inner evaluation loop with a naive Bayesian classifier Genetic algorithm (GA) wrapper around SVM was performed by using our evolutionary search tool, a feature selection method on a Genetic Algorithm (GA) (Schaffer et al. (2005) In: Janevski A, editor; pp. 1-8). The software is available at <<http>>:// www<<.>>csie<<.>>ntu<<.>>edu<<.>>tw/~cjlin/libsvm. A linear kernel was used for feature subset selection. In one GA configuration (1-loop) all discovery samples were available in the discovery process that was repeated 100 times. In another GA configuration (2-loop) a cross-validation was setup to split the discovery data 100 times into disjoint learning and (internal) validation (i.e. samples from the discovery set used to test for robustness of the output subsets) sets maintaining the distribution of the classes. Then, the search works only on the learning data and never sees the samples in the validation data until afterwards in validation. A validation dataset was used outside of the GA execution for final (external) validation. Table 13 shows the summary of the GA output and performance of the subsets that validated perfectly on the internal and external validation samples.

TABLE 13

| Clinical question | # subset discovered at least 2 times (in 2-loop) | #Learning samples (internal validation in 2-loop) | Average learning balanced error rate (in 2-loop) | #Validation samples | Average external validation balanced error rate (in 2-loop) | Average external validation sensitivity (in 2-loop) | Average xternal validation specificity (in 2-loop) |
|---|---|---|---|---|---|---|---|
| Adenoma vs. carcinoma | 353 | 72 (19) | 0 | 61 | 0 | 0.8278 | 0.9521 |
| Normal + polyp vs. adenoma + carcinoma | 279 | 122 (21) | 0.0024 | 103 | 0.0712 | 0.9723 | 0.905 |

Example 6

Verification of the Microarray Data

For verifying (and/or quantifying) the miRNA expression data acquired on microarrays, an established quantitative RT-PCR employing a TaqMan MicroRNA assay (Applied Bio systems, Foster City, Calif., USA) was used according to the manufacturer's instructions. Briefly, reverse transcription (RT) was performed with Taqman microRNA RT Kits according to the instruction from Applied Biosystem. 10 ng total RNA was reverse-transcripted in 15 ul RT solution mix that contains 1× Reverse Transcription Buffer, 1×RT primer, 1 nM dNTP, 4U RNase Inhibitor and 50U MultiScribe Reverse Transcriptase. Then the RT solutions were performed by using the thermal program of 16° C., 30 min; 42° C., 30 min; 85° C., 5 min on the PCR machine (Thermal cycler alpha engine, Bio-rad). Quantitative PCR was performed with TaqMan Universal PCR Master Mix kit and Taqman microRNA assays kits according to the instruction from Applied Biosystem. 2 ul RT products were PCR amplified in 1× TaqMan Universal PCR Master Mix, No AmpErase UNG, 1× TaqMan MicroRNA Assay mix. Each reaction was duplicated in triple. The real-time PCR was performed in Roch Light Cycling 480 machine with the program of 96° C., 5 min initial heating; then 45 or 50 cycles of 95° C., 15 s; 60° C., 60 s. Cp value was calculated with 2nd derivative method in LC480 software. Then miRNAs were absolutely quantified with the standard samples Cp values.

Figure 10:
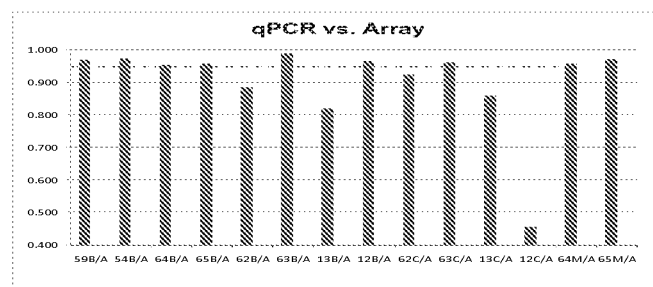
FIG. 10 depicts the experimental data on platform comparison with 17 miRNAs from 14 pairs of the colorectal tumor tissues.
Figure 11:
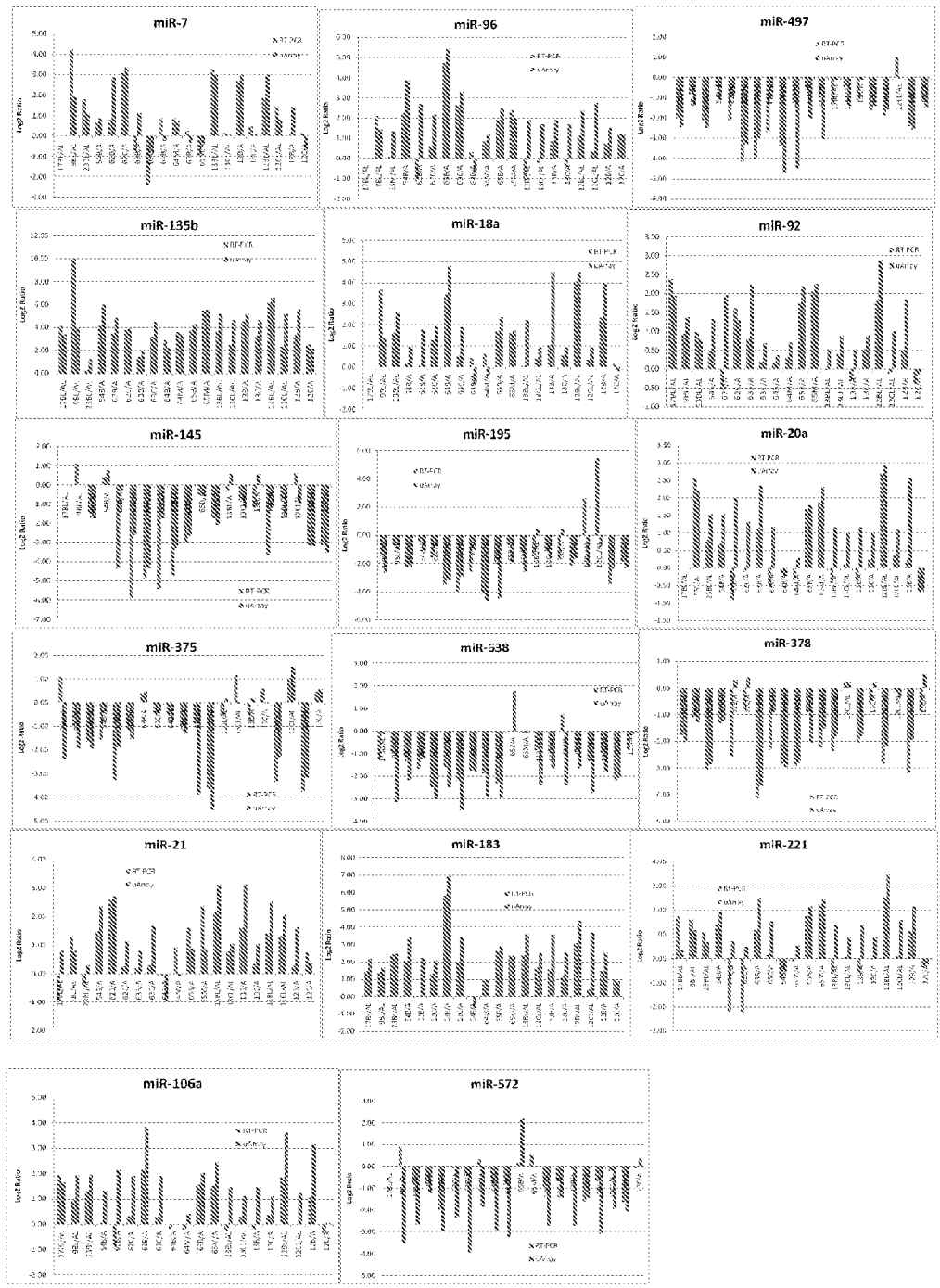
FIG. 11 depicts the expression patterns for each of 17 miRNAs.

The experimental data on platform comparison with 17 miRNAs from 14 pairs of the colorectal tumor tissues show in FIG. 10. The expression patterns for each of 17 miRNAs show in FIG. 11. The quantitative correlation (R) of fold change between Agilent miRNA microarrays and quantitative RT-PCR was 0.90. The results demonstrate that the miRNA signatures discovered using Agilent miRNA microarrays are highly reliable.

The experimental data in the differential miRNA expression analysis are summarized in Tables 14-17 below. Table 14-16 lists the identified miRNAs exhibiting a differential expression in colorectal adenoma and carcinoma. The abbreviation "Sen." denotes sensitivity, whereas "Spec" denotes specificity. "Fold" denotes a ratio of control tissues vs. tumor samples (adenoma or carcinoma). Particularly preferred miRNAs with RUC>0.900 (SEQ ID NO: 121, SEQ ID NO: 55, SEQ ID NO: 7, SEQ ID NO: 51, SEQ ID NO: 4, SEQ ID NO: 15, SEQ ID NO: 65, SEQ ID NO: 83, SEQ ID NO: 66 and SEQ ID NO: 44, SEQ ID NO: 50, SEQ ID NO: 34, SEQ ID NO: 60, SEQ ID NO: 10, SEQ ID NO: 42, SEQ ID NO: 38, SEQ ID NO: 98, SEQ ID NO: 57 and SEQ ID NO: 120 in Table 14, 15 and 16, respectively) are shown in bold. Table 17 lists the literature documented miRNAs in colorectal carcinoma. Of 45 known miRNAs in colorectal carcinomas, 38 (84%) were in the agreement related to the regulations between the invention and the published data.

TABLE 14

Validated identified miRNAs in colorectal adenoma

| | | Discovery | | | | | Validation | | | |
| | | t-test | | ROC analysis | | | t-test | | ROC analysis | |
| Name | tumor | p-val. | fold | Sen. | Spec. | AUC | p-value | fold | Sen. | Spec. | AUC |
| --- | --- | --- | --- | --- | --- | --- | --- | --- | --- | --- | --- |
| has-miR-376a | Adenoma | 2.9E−06 | 0.5 | 93% | 76% | 0.867 | 6.5E−04 | 0.2 | 85% | 88% | 0.893 |
| has-miRF-429 | Adenoma | 2.4E−03 | 1.4 | 67% | 88% | 0.794 | 3.0E−03 | 1.4 | 46% | 93% | 0.765 |
| has-miR-451 | Adenoma | 9.2E−03 | 0.7 | 80% | 78% | 0.830 | 3.5E−06 | 0.4 | 60% | 91% | 0.774 |
| has-miR-99a | Adenoma | 1.6E−09 | 0.3 | 100% | 78% | 0.587 | 4.7E−03 | 0.3 | 69% | 93% | 0.811 |

TABLE 15

Validated identified miRNAs in colorectal adenoma and carcinoma

| | | Discovery | | | | | Validation | | | |
| | | t-test | | ROC analysis | | | t-test | | ROC analysis | |
| Name | tumor | p-val. | fold | Sen. | Spec. | AUC | p-value | fold | Sen. | Spec. | AUC |
| --- | --- | --- | --- | --- | --- | --- | --- | --- | --- | --- | --- |
| hsa-miR-139-5p | Adenoma | 3.5E−10 | 0.3 | 87% | 88% | 0.943 | 4.1E−08 | 0.3 | 92% | 93% | 0.911 |
| | Carcinoma | 1.2E−14 | 0.3 | 77% | 100% | 0.917 | 1.3E−14 | 0.3 | 85% | 93% | 0.912 |
| hsa-miR-497 | Adenoma | 3.6E−05 | 0.5 | 80% | 86% | 0.902 | 3.4E−04 | 0.5 | 85% | 91% | 0.876 |
| | Carcinoma | 3.4E−21 | 0.3 | 90% | 100% | 0.95 | 9.6E−19 | 0.2 | 92% | 98% | 0.985 |
| hsa-miR-378* | Adenoma | 1.1E−05 | 0.5 | 73% | 84% | 0.847 | 8.6E−03 | 0.5 | 92% | 55% | 0.799 |
| | Carcinoma | 8.8E−19 | 0.2 | 83% | 98% | 0.959 | 1.4E−16 | 0.2 | 92% | 91% | 0.951 |
| hsa-miR-182 | Adenoma | 3.3E−10 | 3.6 | 80% | 94% | 0.921 | 4.5E−03 | 2.7 | 69% | 83% | 0.81 |
| | Carcinoma | 2.0E−15 | 4.2 | 91% | 72% | 0.897 | 2.6E−15 | 4.4 | 83% | 93% | 0.914 |
| hsa-miR-20b | Adenoma | 1.9E−19 | 2.8 | 73% | 90% | 0.791 | 6.0E−17 | 2.7 | 69% | 93% | 0.801 |
| | Carcinoma | 1.9E−19 | 2.8 | 86% | 96% | 0.928 | 6.0E−17 | 2.7 | 90% | 95% | 0.927 |
| hsa-miR-17* | Adenoma | 3.5E−13 | 3.1 | 93% | 60% | 0.77 | 2.4E−13 | 2.7 | 46% | 93% | 0.716 |
| | Carcinoma | 3.5E−13 | 3.1 | 88% | 82% | 0.889 | 2.4E−13 | 2.7 | 90% | 81% | 0.92 |
| hsa-miR-376c | Adenoma | 1.6E−06 | 0.4 | 93% | 84% | 0.921 | 5.6E−04 | 0.3 | 92% | 86% | 0.918 |
| | Carcinoma | 2.5E−05 | 0.6 | 68% | 74% | 0.748 | 5.7E−06 | 0.5 | 79% | 79% | 0.824 |
| hsa-miR-20a* | Adenoma | 7.2E−03 | 1.6 | 67% | 78% | 0.715 | 8.7E−03 | 2.1 | 69% | 95% | 0.788 |
| | Carcinoma | 2.0E−12 | 2.9 | 86% | 78% | 0.862 | 3.4E−12 | 3.1 | 81% | 91% | 0.895 |
| hsa-miR-638 | Adenoma | 5.2E−03 | 0.5 | 80% | 66% | 0.733 | 2.5E−03 | 0.5 | 85% | 74% | 0.786 |
| | Carcinoma | 2.0E−10 | 0.3 | 63% | 98% | 0.848 | 2.4E−10 | 0.3 | 77% | 88% | 0.867 |
| hsa-miR-335* | Adenoma | 6.3E−04 | 1.9 | 67% | 80% | 0.778 | 6.8E−03 | 1.8 | 77% | 71% | 0.722 |
| | Carcinoma | 1.7E−11 | 2.4 | 77% | 80% | 0.853 | 6.8E−10 | 2.4 | 90% | 71% | 0.848 |
| hsa-miR-342-5p | Adenoma | 7.0E−04 | 0.6 | 87% | 68% | 0.795 | 1.6E−03 | 0.5 | 85% | 67% | 0.777 |
| | Carcinoma | 3.2E−11 | 0.4 | 79% | 82% | 0.833 | 2.5E−09 | 0.4 | 90% | 67% | 0.833 |
| hsa-miR-34b* | Adenoma | 3.8E−07 | 2.2 | 80% | 86% | 0.885 | 4.6E−03 | 1.9 | 69% | 91% | 0.800 |
| | Carcinoma | 1.2E−07 | 1.9 | 74% | 84% | 0.808 | 5.7E−09 | 2.2 | 79% | 86% | 0.849 |
| hsa-miR-145* | Adenoma | 4.4E−07 | 0.5 | 80% | 84% | 0.888 | 6.7E−04 | 0.4 | 69% | 86% | 0.778 |
| | Carcinoma | 1.0E−06 | 0.5 | 68% | 90% | 0.809 | 1.0E−06 | 0.4 | 52% | 95% | 0.790 |
| hsa-miR-552 | Adenoma | 2.1E−09 | 4.1 | 73% | 80% | 0.843 | 6.3E−13 | 5.2 | 69% | 71% | 0.707 |
| | Carcinoma | 2.1E−09 | 4.1 | 68% | 98% | 0.81 | 6.3E−13 | 5.2 | 73% | 95% | 0.889 |

TABLE 16

Validated identified miRNAs in colorectal carcinoma

| | | Discovery | | | | | Validation | | | | |
|---|---|---|---|---|---|---|---|---|---|---|---|
| | | t-test | | ROC analysis | | | t-test | | ROC analysis | | |
| Name | tumor | p-val. | fold | Sen. | Spec. | AUC | p-value | fold | Sen. | Spec. | AUC |
| hsa-miR-424 | Carcinoma | 1.7E−21 | 3.9 | 84% | 98% | 0.954 | 1.2E−13 | 4.0 | 81% | 95% | 0.912 |
| hsa-miR-378 | Carcinoma | 1.2E−17 | 0.3 | 86% | 96% | 0.945 | 1.2E−10 | 0.4 | 88% | 91% | 0.909 |
| hsa-miR-375 | Carcinoma | 2.6E−17 | 0.2 | 90% | 94% | 0.936 | 5.0E−15 | 0.2 | 88% | 98% | 0.949 |
| hsa-miR-139-3p | Carcinoma | 3.1E−15 | 0.3 | 86% | 86% | 0.929 | 1.4E−14 | 0.3 | 96% | 81% | 0.944 |
| hsa-miR-18b | Carcinoma | 4.5E−15 | 3.9 | 83% | 96% | 0.904 | 1.8E−11 | 3.5 | 83% | 91% | 0.889 |
| hsa-miR-18a | Carcinoma | 3.4E−14 | 3.5 | 86% | 94% | 0.901 | 1.6E−12 | 3.6 | 83% | 91% | 0.915 |
| hsa-miR-650 | Carcinoma | 7.5E−16 | 0.2 | 88% | 84% | 0.895 | 3.4E−18 | 0.1 | 92% | 86% | 0.929 |
| hsa-miR-194* | Carcinoma | 1.2E−12 | 0.4 | 74% | 88% | 0.895 | 4.3E−08 | 0.5 | 85% | 69% | 0.835 |
| hsa-miR-194 | Carcinoma | 1.0E−11 | 0.4 | 77% | 88% | 0.879 | 6.0E−14 | 0.5 | 79% | 93% | 0.915 |
| hsa-miR-29c | Carcinoma | 2.8E−12 | 0.6 | 79% | 86% | 0.878 | 2.8E−13 | 0.5 | 92% | 79% | 0.914 |
| hsa-miR-365 | Carcinoma | 1.9E−10 | 1.9 | 63% | 100% | 0.879 | 3.2E−05 | 1.6 | 75% | 83% | 0.772 |
| hsa-miR-939 | Carcinoma | 1.9E−12 | 0.3 | 75% | 86% | 0.865 | 2.0E−06 | 0.4 | 83% | 69% | 0.808 |
| hsa-miR-181c | Carcinoma | 1.4E−09 | 2.2 | 79% | 90% | 0.852 | 1.8E−07 | 2.4 | 77% | 79% | 0.828 |
| hsa-miR-513c | Carcinoma | 4.4E−11 | 0.3 | 77% | 80% | 0.847 | 3.6E−06 | 0.4 | 94% | 55% | 0.781 |
| hsa-miR-572 | Carcinoma | 8.5E−12 | 0.3 | 70% | 98% | 0.846 | 7.0E−10 | 0.3 | 79% | 91% | 0.871 |
| hsa-miR-130b | Carcinoma | 2.0E−09 | 2.0 | 72% | 84% | 0.83 | 7.2E−10 | 2.3 | 77% | 88% | 0.856 |
| hsa-miR-30e | Carcinoma | 1.2E−08 | 0.6 | 74% | 82% | 0.826 | 1.7E−11 | 0.6 | 77% | 88% | 0.87 |
| hsa-miR-455-3p | Carcinoma | 5.8E−08 | 2.4 | 63% | 96% | 0.822 | 4.2E−08 | 3.0 | 85% | 81% | 0.865 |
| hsa-miR-192* | Carcinoma | 5.5E−09 | 0.4 | 67% | 96% | 0.821 | 4.2E−09 | 0.5 | 71% | 95% | 0.888 |
| hsa-miR-301a | Carcinoma | 2.7E−08 | 2.6 | 58% | 98% | 0.819 | 3.5E−08 | 2.2 | 81% | 71% | 0.825 |
| hsa-miR-452 | Carcinoma | 1.7E−08 | 2.2 | 70% | 86% | 0.815 | 2.2E−10 | 2.7 | 65% | 98% | 0.869 |
| hsa-miR-98 | Carcinoma | 1.7E−08 | 1.9 | 54% | 98% | 0.812 | 2.5E−07 | 1.9 | 63% | 91% | 0.807 |
| hsa-miR-486-5p | Carcinoma | 9.0E−10 | 0.4 | 60% | 86% | 0.811 | 8.9E−08 | 0.4 | 81% | 81% | 0.845 |
| hsa-miR-662 | Carcinoma | 1.4E−08 | 0.5 | 81% | 70% | 0.811 | 3.7E−05 | 0.6 | 83% | 64% | 0.761 |
| hsa-miR-19b | Carcinoma | 7.1E−07 | 1.6 | 68% | 80% | 0.777 | 4.4E−04 | 1.4 | 83% | 57% | 0.745 |
| hsa-miR-30e* | Carcinoma | 6.0E−06 | 0.6 | 81% | 70% | 0.771 | 1.0E−04 | 0.6 | 85% | 57% | 0.741 |
| hsa-miR-151-3p | Carcinoma | 3.1E−05 | 1.5 | 65% | 84% | 0.769 | 1.1E−11 | 1.7 | 77% | 98% | 0.875 |
| hsa-miR-29c* | Carcinoma | 1.9E−05 | 0.6 | 77% | 72% | 0.766 | 3.2E−06 | 0.6 | 71% | 83% | 0.792 |
| hsa-miR-623 | Carcinoma | 5.0E−06 | 0.5 | 68% | 78% | 0.766 | 3.9E−07 | 0.5 | 71% | 86% | 0.820 |
| hsa-miR-550- | Carcinoma | 1.3E−06 | 1.9 | 54% | 96% | 0.731 | 2.2E−06 | 2.0 | 52% | 95% | 0.753 |
| hsa-miR-134 | Carcinoma | 1.6E−04 | 0.5 | 74% | 66% | 0.722 | 2.7E−04 | 0.5 | 58% | 83% | 0.738 |
| hsa-miR-128 | Carcinoma | 4.6E−03 | 1.4 | 79% | 60% | 0.717 | 1.1E−03 | 1.5 | 44% | 91% | 0.714 |
| hsa-miR-21* | Carcinoma | 2.1E−04 | 1.5 | 60% | 82% | 0.709 | 8.0E−05 | 1.7 | 54% | 81% | 0.730 |

TABLE 17

Validated literature documented miRNAs in colorectal carcinoma

| | | Discovery | | Validation | |
|---|---|---|---|---|---|
| | tumor | p-val. | fold | p-val. | fold |
| hsa-miR-204 | Adenoma | 3.04E−14 | 0.3 | 5.13E−04 | 0.4 |
| hsa-miR-203 | Adenoma | 3.26E−09 | 2.6 | 2.92E−04 | 2.4 |
| hsa-miR-100 | Adenoma | 1.11E−13 | 0.3 | 1.35E−03 | 0.3 |
| hsa-miR-199b-5p | Adenoma | 7.56E−07 | 0.6 | 1.38E−03 | 0.6 |
| hsa-miR-135b | Adenoma | 1.08E−14 | 12.3 | 2.68E−11 | 8.1 |
| | Carcinoma | 5.05E−23 | 13.8 | 5.00E−22 | 14.2 |
| hsa-miR-133b | Adenoma | 4.59E−11 | 0.4 | 3.12E−08 | 0.2 |
| | Carcinoma | 5.26E−11 | 0.2 | 1.00E−17 | 0.1 |
| hsa-miR-1 | Adenoma | 5.55E−07 | 0.3 | 2.36E−06 | 0.3 |
| | Carcinoma | 1.37E−09 | 0.2 | 6.60E−16 | 0.1 |
| hsa-miR-30a | Adenoma | 3.89E−07 | 0.6 | 1.80E−04 | 0.5 |
| | Carcinoma | 1.59E−13 | 0.5 | 5.44E−13 | 0.5 |
| hsa-miR-106b | Adenoma | 1.08E−03 | 1.3 | 8.34E−05 | 1.5 |
| | Carcinoma | 2.52E−09 | 1.7 | 4.00E−12 | 1.8 |
| hsa-miR-342-3p | Adenoma | 5.33E−06 | 0.6 | 4.13E−06 | 0.6 |
| | Carcinoma | 1.03E−09 | 0.5 | 3.50E−11 | 0.5 |
| hsa-miR-143 | Adenoma | 1.04E−05 | 0.5 | 9.56E−05 | 0.4 |
| | Carcinoma | 5.91E−04 | 0.6 | 1.76E−06 | 0.4 |
| hsa-miR-224 | Adenoma | 2.85E−09 | 3.3 | 1.07E−05 | 3.3 |
| | Carcinoma | 3.75E−16 | 5.4 | 1.25E−22 | 8.4 |
| hsa-miR-195 | Adenoma | 1.45E−12 | 0.5 | 1.54E−04 | 0.5 |
| | Carcinoma | 2.84E−20 | 0.3 | 8.93E−21 | 0.2 |
| hsa-miR-24 | Adenoma | 3.60E−04 | 1.2 | 8.38E−03 | 1.3 |
| | Carcinoma | 2.13E−12 | 1.5 | 7.03E−18 | 1.8 |
| hsa-miR-20a | Adenoma | 7.27E−03 | 1.4 | 1.14E−03 | 1.5 |
| | Carcinoma | 1.20E−19 | 2.6 | 2.83E−17 | 2.6 |
| hsa-miR-183 | Adenoma | 8.75E−09 | 4.2 | 9.12E−04 | 3.5 |
| | Carcinoma | 2.25E−18 | 5.7 | 2.42E−16 | 5.3 |
| hsa-miR-192 | Adenoma | 4.60E−03 | 0.8 | 1.67E−03 | 0.6 |
| | Carcinoma | 1.68E−11 | 0.4 | 1.69E−15 | 0.4 |
| hsa-miR--93 | Adenoma | 4.09E−04 | 1.4 | 1.50E−04 | 1.7 |
| | Carcinoma | 5.60E−11 | 1.8 | 2.76E−13 | 2.1 |
| hsa-miR-96 | Adenoma | 5.40E−11 | 3.6 | 5.80E−10 | 3.6 |
| | Carcinoma | 1.77E−17 | 3.9 | 5.03E−12 | 3.4 |
| hsa-miR-145 | Adenoma | 1.49E−09 | 0.4 | 1.33E−06 | 0.3 |
| | Carcinoma | 1.41E−08 | 0.4 | 7.45E−10 | 0.3 |
| hsa-miR-27a | Adenoma | 9.20E−06 | 1.6 | 2.92E−06 | 1.4 |
| | Carcinoma | 3.35E−10 | 1.6 | 6.49E−09 | 1.7 |
| hsa-miR-95 | Adenoma | 3.94E−03 | 1.9 | 7.90E−06 | 3.2 |
| | Carcinoma | 3.12E−05 | 1.9 | 1.68E−06 | 2.7 |
| hsa-miR-148b | Carcinoma | 6.04E−03 | 1.3 | 5.01E−03 | 1.2 |
| hsa-miR-335 | Carcinoma | 1.84E−04 | 1.7 | 3.81E−04 | 1.6 |
| hsa-miR-7 | Carcinoma | 1.53E−08 | 2.5 | 7.81E−06 | 2.3 |
| hsa-miR-19a | Carcinoma | 2.96E−09 | 1.8 | 1.32E−05 | 1.6 |
| hsa-miR-338-3p | Carcinoma | 1.56E−03 | 0.6 | 5.66E−03 | 0.6 |
| hsa-miR-221 | Carcinoma | 1.21E−18 | 2.7 | 2.14E−15 | 3.0 |
| hsa-miR-23a | Carcinoma | 1.08E−16 | 1.7 | 6.64E−20 | 2.0 |
| hsa-miR-10b | Carcinoma | 3.17E−12 | 0.4 | 1.82E−07 | 0.5 |
| hsa-miR-150 | Carcinoma | 1.78E−11 | 0.3 | 4.52E−11 | 0.2 |
| hsa-miR-31 | Carcinoma | 2.59E−07 | 4.6 | 8.76E−07 | 6.0 |
| hsa-miR-29b | Carcinoma | 7.02E−05 | 1.5 | 6.67E−05 | 1.5 |
| hsa-miR-29a | Carcinoma | 9.25E−03 | 1.3 | 1.96E−03 | 1.3 |
| hsa-miR-106a | Carcinoma | 1.75E−11 | 3.0 | 1.21E−11 | 3.3 |

TABLE 17-continued

Validated literature documented miRNAs in colorectal carcinoma

| | | Discovery | | Validation | |
|---|---|---|---|---|---|
| | tumor | p-val. | fold | p-val. | fold |
| hsa-miR-25 | Carcinoma | 1.15E−10 | 1.8 | 3.41E−11 | 2.0 |
| hsa-miR-17 | Carcinoma | 4.84E−22 | 2.7 | 3.91E−18 | 2.9 |
| hsa-miR-21 | Carcinoma | 8.68E−08 | 2.1 | 2.73E−04 | 1.8 |
| hsa-miR-215 | Carcinoma | 1.54E−13 | 0.4 | 1.46E−18 | 0.4 |
| hsa-miR-196b | Carcinoma | 2.07E−03 | 1.7 | 6.17E−03 | 1.7 |
| hsa-miR-26b | Carcinoma | 4.31E−06 | 0.7 | 4.47E−03 | 0.8 |
| hsa-miR-132 | Carcinoma | 5.67E−03 | 0.7 | 1.56E−03 | 0.7 |
| hsa-miR-92a | Carcinoma | 1.52E−16 | 2.3 | 1.32E−17 | 2.5 |
| hsa-miR-125a-3p | Carcinoma | 5.86E−07 | 0.4 | 6.95E−05 | 0.5 |
| hsa-miR-30c | Carcinoma | 5.73E−08 | 0.6 | 5.74E−08 | 0.6 |

The experimental data in the disease state progression analysis are summarized in Tables 18-20 below. Table 18 lists validated miRNAs that changes in expression level with the transformation from normal to adenoma. "Fold" denotes a ratio of control tissues vs. adenoma. Table 19 lists validated miRNAs that changes in expression level with the adenoma to carcinoma Dukes' A/B transition. "Fold" denotes a ratio of adenoma vs. carcinoma Dukes' A/B. Table 20 lists a validated miRNA that consistently changes in expression level with normal to adenoma as well as adenoma to carcinoma Dukes'a A/B progression. Particularly preferred identified miRNAs (SEQ ID NO: 55, SEQ ID NO: 72, SEQ ID NO: 4, SEQ ID NO: 45, SEQ ID NO: 57, SEQ ID NO: 100, SEQ ID NO: 36, SEQ ID NO: 38, SEQ ID NO: 42, SEQ ID NO: 10, SEQ ID NO: 62 and SEQ ID NO: 40 in Table 18, 19 and 20, respectively) are shown in bold. In the column "ID", the abbreviation "k" denotes a known miRNA, whereas "n" denotes a newly identified miRNA in the transformation and progression of colorectal cancer.

TABLE 18

Validated miRNAs that changes in expression level with the transformation from normal to adenoma

| | | Discovery | | Validation | |
|---|---|---|---|---|---|
| ID | Name | p-val. | fold | p-val. | fold |
| | | Down regulation | | | |
| N | hsa-miR-139-5p | 4.1E−09 | 0.3 | 3.1E−08 | 0.3 |
| N | hsa-miR-145* | 4.9E−06 | 0.5 | 3.1E−03 | 0.4 |
| K | hsa-miR-133b | 5.0E−10 | 0.4 | 3.5E−05 | 0.2 |
| K | hsa-miR-145 | 3.0E−08 | 0.4 | 2.0E−05 | 0.3 |
| K | hsa-miR-195 | 3.0E−07 | 0.5 | 2.1E−04 | 0.5 |
| K | hsa-miR-342-3p | 1.6E−06 | 0.6 | 6.0E−03 | 0.6 |
| K | hsa-miR-143 | 1.9E−05 | 0.5 | 3.2E−04 | 0.4 |
| K | hsa-miR-1 | 6.9E−05 | 0.3 | 8.3E−05 | 0.3 |
| K | hsa-miR-30a | 1.2E−04 | 0.6 | 1.9E−04 | 0.5 |
| K | hsa-miR-99b | 7.5E−04 | 0.7 | 1.2E−02 | 0.5 |
| K | hsa-miR-26a | 1.2E−03 | 0.8 | 2.7E−02 | 0.8 |
| | | Up-regulation | | | |
| N | hsa-miR-182 | 8.1E−08 | 3.9 | 4.2E−03 | 2.4 |
| N | hsa-miR-552 | 3.7E−05 | 3.3 | 3.8E−02 | 2.0 |
| K | hsa-miR-135b | 5.7E−15 | 13.7 | 4.4E−08 | 7.9 |
| K | hsa-miR-96 | 1.6E−10 | 4.0 | 6.1E−06 | 3.4 |
| K | hsa-miR-203 | 8.3E−10 | 2.8 | 2.9E−05 | 2.6 |
| K | hsa-miR-183 | 2.8E−08 | 4.7 | 1.2E−03 | 3.2 |
| K | hsa-miR-34b* | 8.8E−06 | 2.3 | 1.9E−02 | 1.9 |
| K | hsa-miR-34a | 1.9E−05 | 2.0 | 4.8E−04 | 1.9 |
| K | hsa-miR-27a | 2.2E−05 | 1.6 | 1.8E−03 | 1.4 |
| K | hsa-miR-374a | 1.2E−04 | 1.6 | 3.3E−03 | 1.4 |
| k | hsa-miR-625 | 3.3E−04 | 2.1 | 6.1E−02 | 1.8 |
| k | hsa-miR-148a | 6.4E−04 | 1.5 | 4.0E−02 | 1.3 |

TABLE 19

Validated miRNAs that changes in expression level with adenoma to carcinoma Dukes' A/B transition transition

| | | Discovery | | Validation | |
|---|---|---|---|---|---|
| ID | Name | p-val. | fold | p-val. | fold |
| | | Down regulation | | | |
| n | hsa-miR-194 | 1.0E−04 | 0.5 | 4.0E−02 | 0.8 |
| n | hsa-miR-30e | 1.5E−04 | 0.7 | 2.0E−02 | 0.7 |
| n | hsa-miR-572 | 1.3E−04 | 0.3 | 3.4E−03 | 0.5 |
| n | hsa-miR-650 | 3.2E−05 | 0.2 | 2.1E−02 | 0.4 |
| k | hsa-miR-125a-3p | 4.8E−05 | 0.3 | 3.0E−02 | 0.5 |
| k | hsa-miR-200a | 4.8E−04 | 0.6 | 7.0E−03 | 0.8 |
| k | hsa-miR-215 | 2.6E−05 | 0.5 | 8.2E−04 | 0.7 |
| K | hsa-miR-801 | 1.3E−05 | 0.3 | 1.1E−01 | 0.6 |
| | | Up-regulation | | | |
| N | hsa-miR-18a | 4.3E−04 | 2.6 | 1.0E−02 | 2.7 |
| N | hsa-miR-18b | 2.8E−04 | 2.7 | 9.0E−03 | 2.7 |
| N | hsa-miR-455-3p | 2.5E−04 | 2.6 | 8.4E−03 | 2.0 |
| K | hsa-miR-193a-5p | 1.9E−04 | 1.8 | 1.2E−02 | 2.1 |
| K | hsa-miR-365 | 1.2E−04 | 1.9 | 8.6E−04 | 1.7 |
| K | hsa-miR-409-3p | 9.4E−04 | 2.0 | 1.3E−05 | 2.4 |

TABLE 20

Validated miRNA that consistently changes in expression level with normal to adenoma and adenoma to carcinoma Dukes'a A/B progression

| | | Discovery | | | | Validation | | | |
|---|---|---|---|---|---|---|---|---|---|
| | | Normal vs. adenoma | | Adenoma vs. carcinoma | | Normal vs. adenoma | | Adenoma vs. carcinoma | |
| ID | Name | p-val. | fold | p-val. | fold | p-val. | fold | p-val. | fold |
| n | hsa-miR-939 | 1.7E−03 | 0.5 | 5.0E−04 | 0.5 | 9.8E−03 | 0.6 | 5.0E−02 | 0.7 |

Figure 12:
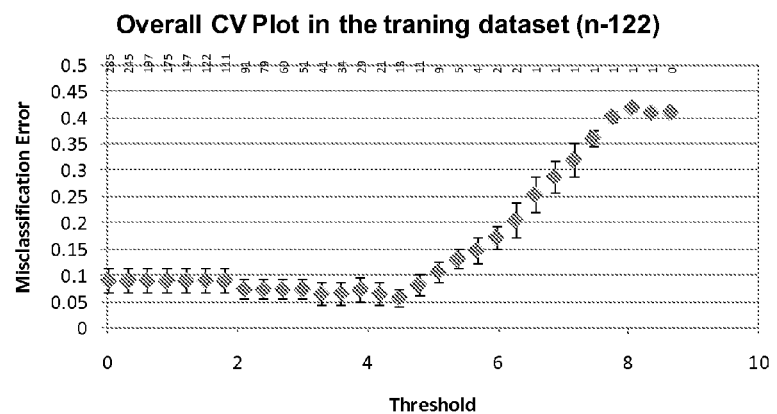
FIG. 12 depicts overall CV plot of level-1 classifiers in the training dataset (A), cross-validation confusion matrix in the training dataset (B) and the testing dataset (C).

In the prediction analysis, three panels of biomarkers for discriminating adenoma/carcinoma from normal/polyp conditions (named Level-1 classifiers) and three panels of biomarkers for further discriminating adenoma and carcinoma (named Level-2 classifiers) were generated by the three supervised classification algorithms. The expression data in the prediction analysis are summarized in Tables 21-30 and FIGS. 12 and 13. In the column "ID", the abbreviation "k" denotes a known miRNA, whereas "n" denotes a newly identified miRNA in the prediction of colorectal adenoma and carcinoma.

i) Level-1 Classifiers (Adenoma/Carcinoma Vs. Normal/Polyp)

Level-1 PAM classifier: a minimal set of 13 miRNAs were identified in the training dataset from the discovery study. The PAM scores for each miRNA correspond to their predictive power in discriminating adenoma/carcinoma and normal-polyp samples list in Table 21. 10-fold cross-validation analysis (FIG. 12B) shows the training balanced accuracy 94.26% of this classifier. Applying the resulting predictor on the testing dataset (n=103) from the validation study gives the balanced accuracy 95.15% (FIG. 12C).

TABLE 21

PAM scores of level-1 classifiers in the training dataset (n = 122)

| ID | Name | Adenoma – carcinoma score | Normal – polyp score |
|---|---|---|---|
| n | hsa-miR-378* | −0.0642 | 0.0925 |
| n | hsa-miR-497 | −0.0576 | 0.0829 |
| n | hsa-miR-375 | −0.0517 | 0.0745 |
| n | hsa-miR-139-5p | −0.0336 | 0.0484 |
| n | hsa-miR-378 | −0.0067 | 0.0097 |
| n | hsa-miR-424 | 0.0291 | −0.0418 |
| n | hsa-miR-182 | 0.0742 | −0.1068 |
| k | hsa-miR-195 | −0.0592 | 0.0852 |
| k | hsa-miR-133b | −0.0109 | 0.0157 |
| k | hsa-miR-96 | 0.0906 | −0.1304 |
| k | hsa-miR-224 | 0.0959 | −0.1381 |
| k | hsa-miR-183 | 0.1395 | −0.2009 |
| k | hsa-miR-135b | 0.315 | −0.4535 |

Level-1 GA classifier: top ranked features of 19 miRNAs were identified from the training dataset (n=122) and further validated with internal (n=21) and external (n=103) validation samples in discriminating colorectal adenoma/carcinoma from normal/polyp samples. The performance of the top ranked features shows in Table 22. The average accuracy in the top subsets is 94.02%.

TABLE 22

The performance of the top ranked features in leveal-1 GA classifiers

| ID | Count | Subset | Sensitivity | Specificity |
|---|---|---|---|---|
| n | 7 | hsa-miR-497 | 100% | 92% |
| n | 7 | hsa-miR-139-3p | 91% | 94% |
| k | 8 | hsa-miR-192 | 93% | 94% |
| k | 8 | hsa-miR-381 | 91% | 94% |
| k | 7 | hsa-miR-96 | 95% | 91% |
| k | 7 | hsa-miR-195 | 91% | 94% |
| k | 7 | hsa-let-7g | 100% | 90% |
| k | 7 | hsa-miR-29b | 98% | 90% |
| k | 7 | hsa-miR-21 | 100% | 88% |
| k | 7 | hsa-miR-183 | 98% | 91% |
| k | 7 | hsa-miR-27a | 100% | 91% |
| k | 7 | hsa-miR-193a-3p | 98% | 90% |
| k | 7 | hsa-miR-135b | 98% | 92% |
| k | 7 | hsa-miR-16 | 100% | 92% |

TABLE 22-continued

The performance of the top ranked features in leveal-1 GA classifiers

| ID | Count | Subset | Sensitivity | Specificity |
|---|---|---|---|---|
| k | 7 | hsa-miR-29a | 95% | 92% |
| k | 7 | hsa-miR-10b | 95% | 94% |
| k | 7 | hsa-miR-320 | 98% | 92% |
| k | 7 | hsa-miR-24 | 98% | 91% |
| k | 7 | hsa-let-7c | 91% | 91% |

Level-1 One-Loop Naïve Bayesian Classifier:

The feature selection step in the training dataset (n=122) from the discovery study resulted in 74 features in discriminating colorectal adenoma/carcinoma from normal/polyp samples. These 74 miRNAs with in order of decreasing importance list in Table 23. Cross-validation analysis (Table 24) shows the training balanced accuracy 96.9% of this classifier in discriminating adenoma/carcinomas and normal-polyp samples (n=122). Applying the resulting predictor on the testing dataset (n=103) from the validation study gives the balanced accuracy 96.7%%.

TABLE 23

Mostly frequently selected miRNAs in level-1 one-loop Naïve Bayesian classifier

| ID | Name | Rank | ID | Name | Rank |
|---|---|---|---|---|---|
| k | hsa-miR-135b | 1 | k | hsa-miR-106a | 38 |
| k | hsa-miR-195 | 2 | k | hsa-miR-145 | 39 |
| n | hsa-miR-497 | 3 | n | hsa-miR-29c | 40 |
| k | hsa-miR-183 | 4 | n | hsa-miR-552 | 41 |
| k | hsa-miR-96 | 5 | k | hsa-miR-572 | 42 |
| k | hsa-miR-221 | 6 | n | hsa-miR-638 | 43 |
| k | hsa-miR-17 | 7 | k | hsa-miR-192 | 44 |
| n | hsa-miR-182 | 8 | n | hsa-miR-181c | 45 |
| k | hsa-miR-224 | 9 | k | hsa-miR-381 | 46 |
| n | hsa-miR-378* | 10 | k | hsa-miR-194* | 47 |
| n | hsa-miR-139-5p | 11 | k | hsa-miR-25 | 48 |
| k | hsa-miR-23a | 12 | k | hsa-miR-181d | 49 |
| n | hsa-miR-424 | 13 | n | hsa-miR-34b* | 50 |
| n | hsa-miR-20b | 14 | k | hsa-miR-106b | 51 |
| k | hsa-miR-20a | 15 | k | hsa-miR-194 | 52 |
| n | hsa-miR-378 | 16 | k | hsa-miR-34a | 53 |
| k | hsa-miR-30a | 17 | k | hsa-miR-301b | 54 |
| n | hsa-miR-375 | 18 | n | hsa-miR-513c | 55 |
| n | hsa-miR-139-3p | 19 | n | hsa-miR-130b | 56 |
| n | hsa-miR-18b | 20 | n | hsa-miR-145* | 57 |
| k | hsa-miR-133b | 21 | k | hsa-miR-31 | 58 |
| n | hsa-miR-939 | 22 | k | hsa-miR-19a | 59 |
| k | hsa-miR-10b | 23 | k | hsa-miR-21 | 60 |
| k | hsa-miR-24 | 24 | k | hsa-miR-365 | 61 |
| k | hsa-miR-92a | 25 | k | hsa-miR-421 | 62 |
| k | hsa-miR-27a | 26 | k | hsa-miR-592 | 63 |
| n | hsa-miR-335* | 27 | n | hsa-miR-301a | 64 |
| n | hsa-miR-18a | 28 | n | hsa-miR-452 | 65 |
| n | hsa-miR-17* | 29 | k | hsa-miR-187* | 66 |
| n | hsa-miR-342-5p | 30 | n | hsa-miR-98 | 67 |
| n | hsa-miR-650 | 31 | k | hsa-miR-574-3p | 68 |
| n | hsa-miR-20a* | 32 | n | hsa-miR-662 | 69 |
| k | hsa-miR-215 | 33 | n | hsa-miR-376c | 70 |
| k | hsa-miR-150 | 34 | k | hsa-miR-204 | 71 |
|   | hsa-miR-93 | 35 | n | hsa-miR-30e | 72 |
|   | hsa-miR-342-3p | 36 | k | hsa-miR-140-3p | 73 |
|   | hsa-miR-1 | 37 | n | hsa-miR-192* | 74 |

TABLE 24

Confusion matrix of level-1 one-loop Naive Bayesian classifier

| True\Predicted | normal + polyp | adenoma + carcinoma | Prediction error rate |
|---|---|---|---|
| A Confusion matrix on the training dataset (n = 122) | | | |
| normal + polyp | 49 | 1 | 0.02 |
| adenoma + carcinoma | 3 | 69 | 0.04 |
| B Confusion matrix on the testing dataset (n = 103) | | | |
| normal + polyp | 42 | 0 | 0.00 |
| adenoma + carcinoma | 4 | 57 | 14.25 |

Overlapping miRNAs of Level-1 classifiers: The components of the three Level-1 classifiers were compared. The identified miRNAs as components of the classifiers which are shared by any two of the employed classification algorithms hold more promises as miRNAs with strong diagnostic power, especially the small set of miRNAs co-identified by all the three supervised classification algorithms. The shared miRNAs are listed in Table 25. Particularly preferred identified miRNAs (SEQ ID NO: 7, SEQ ID NO: 60, SEQ ID NO: 55, SEQ ID NO: 34, SEQ ID NO: 50, SEQ ID NO: 51, SEQ ID NO: 44 and SEQ ID NO: 4 in Table 16) are shown in bold.

TABLE 25

Classifier comparison and shared miRNAs in level-1 classifiers

| ID | Name | PAM | GA | Naïve Bayesian |
|---|---|---|---|---|
| n | hsa-miR-497 | X | X | X |
| n | hsa-miR-139-3p |   | X | X |
| n | hsa-miR-139-5p | X |   | X |
| n | hsa-miR-375 | X |   | X |
| n | hsa-miR-378 | X |   | X |
| n | hsa-miR-378* | X |   | X |
| n | hsa-miR-424 | X |   | X |
| n | hsa-miR-182 | X |   | X |
| k | hsa-miR-135b | X | X | X |
| k | hsa-miR-183 | X | X | X |
| k | hsa-miR-195 | X | X | X |
| k | hsa-miR-96 | X | X | X |
| k | hsa-miR-10b |   | X | X |
| k | hsa-miR-192 |   | X | X |
| k | hsa-miR-21 |   | X | X |
| k | hsa-miR-24 |   | X | X |
| k | hsa-miR-27a |   |   |   |
| k | hsa-miR-133b | X |   | X |
| k | hsa-miR-224 | X |   | X |
| k | hsa-miR-381 | X |   | X | ii) Level-2 Classifiers (Adenoma Vs. Carcinoma)

Figure 13:
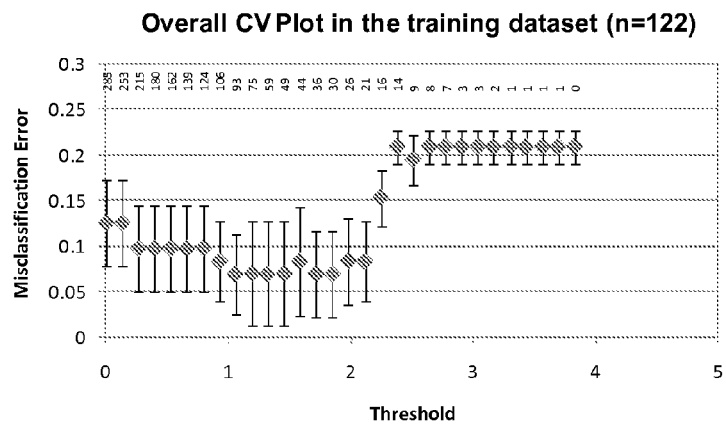
FIG. 13 depicts overall CV plot of level-2 classifiers in the training dataset (A), cross-validation confusion matrix in the training dataset (B) and the testing dataset (C).

Level-2 PAM classifier: a minimal set of 36 miRNAs were identified in the training dataset from the discovery study. The PAM scores for each miRNA correspond to their predictive power in discriminating adenoma from carcinoma show in Table 26. 10-fold cross-validation analysis (FIG. 13) shows the training balanced accuracy 93.06% of this classified. Applying the resulting predictor on the testing dataset (n=103) from the validation study gives the balanced accuracy 93.44% (FIG. 13C).

TABLE 26

PAM scores of level-2 classifiers in the training dataset (n = 122)

| ID | name | Adenoma score | Carcinoma score |
|---|---|---|---|
| n | hsa-miR-451 | 0.293 | −0.078 |
| n | hsa-miR-99a | −0.495 | 0.132 |
| n | hsa-miR-497 | 0.038 | −0.010 |
| n | hsa-miR-378* | 0.088 | −0.023 |
| n | hsa-miR-20b | −0.028 | 0.007 |
| n | hsa-miR-17* | −0.026 | 0.007 |
| n | hsa-miR-424 | −0.241 | 0.064 |
| n | hsa-miR-378 | 0.112 | −0.030 |
| n | hsa-miR-375 | 0.353 | −0.094 |
| n | hsa-miR-18b | −0.140 | 0.037 |
| n | hsa-miR-18a | −0.123 | 0.033 |
| n | hsa-miR-650 | 0.272 | −0.072 |
| n | hsa-miR-194* | 0.005 | −0.001 |
| n | hsa-miR-194 | 0.025 | −0.007 |
| n | hsa-miR-513c | 0.025 | −0.007 |
| n | hsa-miR-572 | 0.031 | −0.008 |
| n | hsa-miR-455-3p | −0.057 | 0.015 |
| n | hsa-miR-192* | 0.101 | −0.027 |
| n | hsa-miR-452 | −0.046 | 0.012 |
| n | hsa-miR-486-5p | 0.136 | −0.036 |
| k | hsa-miR-125b | −0.303 | 0.081 |
| k | hsa-miR-100 | −0.224 | 0.060 |
| k | hsa-miR-214 | −0.216 | 0.058 |
| k | hsa-miR-92a | −0.145 | 0.039 |
| k | hsa-miR-7 | −0.134 | 0.036 |
| k | hsa-miR-218 | −0.107 | 0.029 |
| k | hsa-miR-503 | −0.079 | 0.021 |
| k | hsa-miR-17 | −0.076 | 0.020 |
| k | hsa-miR-654-3p | −0.072 | 0.019 |
| k | hsa-miR-20a | −0.067 | 0.018 |
| k | hsa-miR-365 | −0.049 | 0.013 |
| k | hsa-miR-769-5p | −0.049 | 0.013 |
| k | hsa-miR-106a | −0.035 | 0.009 |
| k | hsa-miR-193a-5p | −0.032 | 0.008 |
| k | hsa-miR-483-3p | −0.030 | 0.008 |
| k | hsa-miR-199a-5p | −0.025 | 0.007 |
| k | hsa-miR-99b | −0.001 | 0.000 |
| k | hsa-miR-801 | 0.003 | −0.001 |
| k | hsa-miR-625 | 0.017 | −0.005 |
| k | hsa-miR-125a-3p | 0.064 | −0.017 |
| k | hsa-miR-150 | 0.088 | −0.024 |
| k | hsa-miR-215 | 0.102 | −0.027 |
| k | hsa-miR-146a | 0.161 | −0.043 |
| k | hsa-miR-144 | 0.321 | −0.086 | b) Level-2 GA classifier: top ranked features of 20 miRNAs were identified from the training dataset (n=122) and further validated with internal (n=21) and external (n=103) validation samples to discriminate colorectal adenoma from carcinoma samples. The performance of the top ranked features shows in Table 27. The average accuracy in the top subsets is 91.51%.

TABLE 27

The performance of the top ranked features in leveal-2 GA classifiers

| ID | Count | Subset | Sensitivity | Specificity |
|---|---|---|---|---|
| n | 7 | hsa-miR-451 | 76% | 98% |
| n | 6 | hsa-miR-378* | 81% | 98% |
| n | 6 | hsa-miR-99a | 87% | 96% |
| n | 7 | hsa-miR-424 | 87% | 98% |
| n | 6 | hsa-miR-378 | 87% | 94% |
| n | 6 | hsa-miR-130b | 87% | 96% |
| n | 6 | hsa-miR-30e | 87% | 96% |
| n | 6 | hsa-miR-192* | 87% | 96% |
| n | 6 | hsa-miR-452 | 87% | 98% |
| n | 6 | hsa-miR-497 | 93% | 96% |
| n | 6 | hsa-miR-375 | 93% | 96% |
| n | 6 | hsa-miR-194* | 93% | 96% |
| k | 6 | hsa-miR-365 | 87% | 96% |
| k | 6 | hsa-miR-494 | 87% | 94% |
| k | 6 | hsa-miR-92a | 87% | 98% |

TABLE 27-continued

The performance of the top ranked features in leveal-2 GA classifiers

| ID | Count | Subset | Sensitivity | Specificity |
|----|-------|--------|-------------|-------------|
| k | 6 | hsa-miR-125b | 87% | 96% |
| k | 6 | hsa-miR-17 | 87% | 96% |
| k | 6 | hsa-miR-193a-5p | 87% | 92% |
| k | 6 | hsa-miR-218 | 87% | 98% |
| k | 6 | hsa-miR-30c | 87% | 96% |

Level-2 One-Loop Naïve Bayesian Classifier:

The feature selection step in the training dataset (n=122) from the discovery study resulted in 27 features for discriminating adenoma from carcinomas. These 27 miRNAs with in order of decreasing importance list in Table 28. Cross-validation analysis (Table 29) shows the training balanced accuracy 99.9% of this classifier. Applying the resulting predictor on the testing dataset (n=103) from the validation study gives the balanced accuracy 87.4%.

TABLE 28

Mostly frequently selected miRNAs in level-2 one-loop Naïve Bayesian classifier

| ID | Name | Rank |
|----|------|------|
| n | hsa-miR-99a | 1 |
| n | hsa-miR-650 | 2 |
| n | hsa-miR-424 | 3 |
| k | hsa-miR-92a | 4 |
| k | hsa-miR-125b | 5 |
| n | hsa-miR-375 | 6 |
| k | hsa-miR-7 | 7 |
| k | hsa-miR-144 | 8 |
| n | hsa-miR-451 | 9 |
| k | hsa-miR-218 | 10 |
| k | hsa-miR-214 | 11 |
| k | hsa-miR-494 | 12 |
| k | hsa-miR-801 | 13 |
| k | hsa-miR-17 | 14 |
| n | hsa-miR-486-5p | 15 |
| n | hsa-miR-378 | 16 |
| k | hsa-miR-20a | 17 |
| n | hsa-miR-194* | 18 |
| k | hsa-miR-215 | 19 |
| n | hsa-miR-194 | 20 |
| n | hsa-miR-29c | 21 |
| n | hsa-miR-513c | 22 |
| k | hsa-miR-100 | 23 |
| n | hsa-miR-139-3p | 24 |
| k | hsa-miR-365 | 25 |
| k | hsa-miR-146a | 26 |
| n | hsa-miR-30e | 27 |

TABLE 29

Confusion matrix of level-2 one-loop Naive Bayesian classifier

| True\Predicted | adenoma | carcinoma | Prediction error rate |
|----------------|---------|-----------|----------------------|
| A Confusion matrix on the training dataset (n = 122) | | | |
| Adenoma | 15 | 0 | 0.00 |
| Carcinoma | 1 | 56 | 0.02 |
| B Confusion matrix on the testing dataset (n = 103) | | | |
| Adenoma | 10 | 3 | 0.30 |
| Carcinoma | 1 | 47 | 0.02 |

Overlapping miRNAs of Level-2 Classifiers:

The components of the three Level-1 classifiers were compared. The identified miRNAs as components of the classifiers which are shared by any two of the employed classification algorithms hold more promises as miRNAs with strong diagnostic power, especially the small set of miRNAs co-identified by all the three supervised classification algorithms. The shared miRNAs are listed in Table 30. Particularly preferred newly identified miRNAs (SEQ ID NO: 34, SEQ ID NO: 44, SEQ ID NO: 70 and SEQ ID NO: 106 in Table 30) are shown in bold.

TABLE 30

Classifier comparison and shared miRNAs in level-2 classifiers

| ID | NAME | PAM | GA | Naive Bayesian |
|----|------|-----|----|----|
| n | hsa-miR-375 | | X | X |
| n | hsa-miR-424 | | X | X |
| n | hsa-miR-451 | | X | X |
| n | hsa-miR-99a | X | | X |
| k | hsa-miR-125b | | X | X |
| k | hsa-miR-144 | X | | X |
| k | hsa-miR-17 | X | X | X |
| k | hsa-miR-193a-5p | X | X | |
| k | hsa-miR-218 | X | X | X |
| k | hsa-miR-365 | X | X | |
| k | hsa-miR-494 | | X | X |
| k | hsa-miR-7 | X | | X |
| k | hsa-miR-801 | X | | X |
| k | hsa-miR-92a | | X | X |

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

The present invention further relates to further embodiments as described as follows:
1. Diagnostic kit of molecular markers for identifying one or more mammalian target cells exhibiting or having a predisposition to develop colorectal cancer, the kit comprising a plurality of nucleic acid molecules, each nucleic acid molecule encoding a microRNA sequence, wherein one or more of the plurality of nucleic acid molecules are differentially expressed in the target cells and in one or more control cells, and wherein the one or more differentially expressed nucleic acid molecules together represent a nucleic acid expression signature that is indicative for the presence of or the predisposition to develop colorectal cancer.

2. The kit of 1, wherein the colorectal cancer is manifested as an adenocarcinoma.

3. The kit of 2, for the further use of identifying a progression of an adenoma to an adenocarcinoma or a predisposition for a progression of an adenoma to an adenocarcinoma.

4. The kit of any of 1 to 3, wherein the nucleic acid expression signature comprises at least one nucleic acid molecule encoding a microRNA sequence whose expression is up-regulated in the one or more target cells compared to the one or more control cells and at least one nucleic acid molecule encoding a microRNA sequence whose expression is down-regulated in the one or more target cells compared to the one or more control cells.

5. The kit of 1 to 4, wherein the nucleic acid expression signature comprises at least three nucleic acid molecules, preferably at least five nucleic acid molecules, and particularly preferably at least ten nucleic acid molecules.

6. The kit of any of 1 to 5, wherein the nucleic acid expression signature comprises nucleic acid molecules encoding hsa-miR-224, hsa-miR-183, and hsa-miR-18b.

7. The kit of 6, wherein the nucleic acid expression signature further comprises nucleic acid molecules encoding hsa-miR-96, hsa-miR-182, and hsa-miR-106a.

8. The kit of any of 1 to 7, wherein the nucleic acid expression signature comprises nucleic acid molecules encoding hsa-miR-224, hsa-miR-96, hsa-miR-21, hsa-miR-182, hsa-miR-183, hsa-miR-221, hsa-miR-497, hsa-miR-106b, hsa-miR-106a, hsa-miR-18b, and hsa-miR-30a.

9. The kit of 8, wherein the nucleic acid expression signature further comprises nucleic acid molecules encoding hsa-miR-135b, hsa-miR-93, hsa-miR-17, hsa-miR-20b, and hsa-miR-24.

10. The kit of 8 or 9, wherein the expression of the nucleic acid molecules encoding hsa-miR-224, hsa-miR-96, hsa-miR-21, hsa-miR-182, hsa-miR-183, hsa-miR-221, hsa-miR-106b, hsa-miR-106a, hsa-miR-18b, hsa-miR-135b, hsa-miR-93, hsa-miR-17, hsa-miR-20b, and hsa-miR-24 is up-regulated and the expression of the nucleic acid molecules hsa-miR-497 and hsa-miR-30a is down-regulated in the in the one or more target cells compared to the one or more control cells.

11. Method for identifying one or more mammalian target cells exhibiting or having a predisposition to develop colorectal cancer, preferably manifested as an adenocarcinoma, the method comprising:
   (a) determining in the one or more target cells the expression levels of a plurality of nucleic acid molecules, each nucleic acid molecule encoding a microRNA sequence;
   (b) determining the expression levels of the plurality of nucleic acid molecules in one or more control cells; and
   (c) identifying from the plurality of nucleic acid molecules one or more nucleic acid molecules that are differentially expressed in the target and control cells by comparing the respective expression levels obtained in steps (a) and (b), wherein the one or more differentially expressed nucleic acid molecules together represent a nucleic acid expression signature, as defined in any of 1 to 10, that is indicative for the presence of or the predisposition to develop colorectal cancer.

12. The method of 11, for the further use of identifying a progression of an adenoma to an adenocarcinoma or a predisposition for a progression of an adenoma to an adenocarcinoma.

13. Method for preventing or treating colorectal cancer, preferably manifested as an adenocarcinoma, in one or more mammalian target cells, the method comprising:
   (a) identifying in one or more target cells a nucleic acid expression signature by using a method as defined in 11 or 12; and
   (b) modifying in the one or more cells the expression of one or more nucleic acid molecules encoding a microRNA sequence that is/are comprised in the nucleic acid expression signature in such way that the expression of a nucleic acid molecule whose expression is up-regulated in the one or more target cells is down-regulated and the expression of a nucleic acid molecule whose expression is down-regulated in the one or more target cells is up-regulated.

14. Pharmaceutical composition for the prevention and/or treatment of colorectal cancer, preferably manifested as an adenocarcinoma, in one or more mammalian target cells, the composition comprising one or more nucleic acid molecules, each nucleic acid molecule encoding a sequence that is at least partially complementary to a microRNA sequence encoded by a nucleic acid molecule whose expression is up-regulated in the one or more target cells, as defined in any of claims 1 to 9, and/or that corresponds to a microRNA sequence encoded by a nucleic acid molecule whose expression is down-regulated in the one or more target cells, as defined in any of 1 to 10.

15. Use of the pharmaceutical composition of 14 for the manufacture of a medicament for the prevention and/or treatment of colorectal cancer, preferably manifested as an adenocarcinoma.

---

The invention claimed is:

1. A diagnostic kit of molecular markers for identifying one or more mammalian target cells exhibiting or having a predisposition to develop colorectal cancer, the kit consisting of a plurality of human target cell-derived nucleic acid molecules encoding the following microRNA sequences: hsa-miR-376a, hsa-miR-424, hsa-miR-378, hsa-miR-375, hsa-miR-139-3p, hsa-miR-18b, hsa-miR-18a, hsa-miR-650, hsa-miR-194*, hsa-miR-194, hsa-miR-29c, hsa-miR-139-5p, hsa-miR-497, hsa-miR-378*, hsa-miR-182, hsa-miR-20b, hsa-miR-17*, hsa-miR-376c, and hsa-miR-20a*, and optionally one or more of hsa-miR-429, hsa-miR-451, hsa-miR-99a, hsa-miR-939, hsa-miR-181c, hsa-miR-513c, hsa-miR-572, hsa-miR-130b, hsa-miR-30e, hsa-miR-455-3p, hsa-miR-192*, hsa-miR-301a, hsa-miR-452, hsa-miR-98, hsa-miR-486-5p, hsa-miR-662, hsa-miR-19b, hsa-miR-30e*, hsa-miR-151-3p, hsa-miR-29c*, hsa-miR-623, hsa-miR-550*, hsa-miR-134, hsa-miR-128, hsa-miR-21*, hsa-miR-638, hsa-miR-335*, hsa-miR-342-5p, hsa-miR-34b*, hsa-miR-145* and hsa-miR-552, wherein:

(i) each of the plurality of human target cell-derived nucleic acid molecules encodes one of the listed microRNA sequences;
(ii) one or more of the human target cell-derived nucleic acid molecules are differentially expressed in the target cells and in one or more control cells; and
(iii) the one or more differentially expressed human target cell-derived nucleic acid molecules together represent a nucleic acid expression signature that is indicative of the presence of or a predisposition to development of colorectal cancer in a human subject.

2. The kit of claim 1, wherein the colorectal cancer is manifested as an adenocarcinoma.

3. The kit of claim 2, for the further use of identifying a predisposition to develop colorectal adenoma or a predisposition to develop colorectal carcinoma or a predisposition to develop colorectal adenoma and carcinoma or identifying a progression of an adenoma to an adenocarcinoma or a predisposition for a progression of an adenoma to an adenocarcinoma.

4. The kit of claim 1, wherein expression of the human target cell-derived nucleic acid molecule encoding hsa-miR-429 is up-regulated and expression of any one or more of the human target cell-derived nucleic acid molecules encoding hsa-miR-376a, hsa-miR-451, and hsa-miR-99a is down-regulated in the one or more target cells as compared to in the one or more control cells.

5. The kit of claim 1, wherein expression of any of the one or more human target cell-derived nucleic acid molecules encoding hsa-miR-424, hsa-miR-18b, hsa-miR-18a, hsa-miR-181c, hsa-miR-130b, hsa-miR-455-3p, hsa-miR-301 a, hsa-miR-452, hsa-miR-98, hsa-miR-19b, hsa-miR-151-3p, hsa-miR-550*, hsa-miR-128, and hsa-miR-21* is up-regulated and expression of any of the one or more human target cell-derived nucleic acid molecules encoding hsa-miR-378, hsa-miR-375, hsa-miR-139-3p, hsa-miR-650, hsa-miR-194*, hsa-miR-194, hsa-miR-29c, hsa-miR-939, hsa-miR-513c, hsa-miR-572, hsa-miR-30e, hsa-miR-192*, hsa-miR-486-5p, hsa-miR-662, hsa-miR-30e*, hsa-miR-29c*, hsa-miR-623, and hsa-miR-134 is down-regulated in the one or more target cells as compared to in the one or more control cells.

6. The kit of claim 1, wherein expression of any of the one or more human target cell-derived nucleic acid molecules encoding hsa-miR-182, hsa-miR-20b, hsa-miR-17*, hsa-miR-20a*, hsa-miR-335*, hsa-miR-34b*, and hsa-miR-552 is up-regulated and expression of any of the one or more human target cell-derived nucleic acid molecules encoding hsa-miR-139-5p, hsa-miR-497, hsa-miR-378*, hsa-miR-376c, hsa-miR-638, hsa-miR-342-5p, and hsa-miR-145* is down-regulated in the one or more target cells as compared to in the one or more control cells.

\* \* \* \* \*

SEQUENCE LISTING

<160> NUMBER OF SEQ ID NOS: 160

<210> SEQ ID NO 1
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-224 microRNA

<400> SEQUENCE: 1
caagucacua gugguuccgu u                                              21

```
<210> SEQ ID NO 2
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-96 microRNA

<400> SEQUENCE: 2
uuuggcacua gcacauuuuu gcu                                               23

<210> SEQ ID NO 3
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-21 microRNA

<400> SEQUENCE: 3
uagcuuauca gacugauguu ga                                                22

<210> SEQ ID NO 4
<211> LENGTH: 24
<212> TYPE: RNA
<213> ORGANISM: Homo sapiens
<220> FEATURE:
<221> NAME/KEY: misc_feature
<223> OTHER INFORMATION: hsa-miR-182 microRNA

<400> SEQUENCE: 4
uuuggcaaug guagaacuca cacu                                              24

<210> SEQ ID NO 5
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-183 microRNA

<400> SEQUENCE: 5
uauggcacug guagaauuca cu                                                22

<210> SEQ ID NO 6
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-221 microRNA

<400> SEQUENCE: 6
agcuacauug ucugcugggu uuc                                               23

<210> SEQ ID NO 7
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-497 microRNA

<400> SEQUENCE: 7
cagcagcaca cuguggonuug u                                                21

<210> SEQ ID NO 8
```

```
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-106a microRNA

<400> SEQUENCE: 8
aaaagugcuu acagugcagg uag                                              23

<210> SEQ ID NO 9
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-106b microRNA

<400> SEQUENCE: 9
uaaagugcug acagugcaga u                                                21

<210> SEQ ID NO 10
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-18b microRNA

<400> SEQUENCE: 10
uaaggugcau cuagugcagu uag                                              23

<210> SEQ ID NO 11
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-30a microRNA

<400> SEQUENCE: 11
uguaaacauc cucgacugga ag                                               22

<210> SEQ ID NO 12
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-135b microRNA

<400> SEQUENCE: 12
uauggcuuuu cauuccuaug uga                                              23

<210> SEQ ID NO 13
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-93 microRNA

<400> SEQUENCE: 13
caaagugcug uucgugcagg uag                                              23

<210> SEQ ID NO 14
<211> LENGTH: 23
```

-continued

```
<212> TYPE: RNA
<213> ORGANISM: Homo sapiens
<220> FEATURE:
<221> NAME/KEY: misc_feature
<223> OTHER INFORMATION: hsa-miR-17 microRNA

<400> SEQUENCE: 14
caaagugcuu acagugcagg uag                                              23

<210> SEQ ID NO 15
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-20b microRNA

<400> SEQUENCE: 15
caaagugcuc auagugcagg uag                                              23

<210> SEQ ID NO 16
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-24 microRNA

<400> SEQUENCE: 16
uggcucaguu cagcaggaac ag                                               22

<210> SEQ ID NO 17
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-423-5p microRNA

<400> SEQUENCE: 17
ugaggggcag agagcgagac uuu                                              23

<210> SEQ ID NO 18
<211> LENGTH: 22
<212> TYPE: RNA
<213> ORGANISM: Homo sapiens
<220> FEATURE:
<221> NAME/KEY: misc_feature
<223> OTHER INFORMATION: hsa-let-7a microRNA

<400> SEQUENCE: 18
ugagguagua gguuguauag uu                                               22

<210> SEQ ID NO 19
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-374a microRNA

<400> SEQUENCE: 19
uuauaauaca accugauaag ug                                               22

<210> SEQ ID NO 20
<211> LENGTH: 21
<212> TYPE: RNA
```

```
<213> ORGANISM: Homo sapiens
<220> FEATURE:
<221> NAME/KEY: misc_feature
<223> OTHER INFORMATION: hsa-miR-21* microRNA

<400> SEQUENCE: 20
caacaccagu cgaugggcug u                                              21

<210> SEQ ID NO 21
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-34a microRNA

<400> SEQUENCE: 21
uggcaguguc uuagcugguu gu                                             22

<210> SEQ ID NO 22
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-203 microRNA

<400> SEQUENCE: 22
gugaaauguu uaggaccacu ag                                             22

<210> SEQ ID NO 23
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-29b microRNA

<400> SEQUENCE: 23
uagcaccauu ugaaaucagu guu                                            23

<210> SEQ ID NO 24
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-145 microRNA

<400> SEQUENCE: 24
guccaguuuu cccaggaauc ccu                                            23

<210> SEQ ID NO 25
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-195 microRNA

<400> SEQUENCE: 25
uagcagcaca gaaauauugg c                                              21

<210> SEQ ID NO 26
<211> LENGTH: 21
<212> TYPE: RNA
<213> ORGANISM: Homo sapiens
```

```
<220> FEATURE:
<221> NAME/KEY: misc_feature
<223> OTHER INFORMATION: hsa-miR-27a microRNA

<400> SEQUENCE: 26
uucacagugg cuaaguuccg c                                                    21

<210> SEQ ID NO 27
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-30e* microRNA

<400> SEQUENCE: 27
cuuucagucg gauguuuaca gc                                                   22

<210> SEQ ID NO 28
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-30c microRNA

<400> SEQUENCE: 28
uguaaacauc cuacacucuc agc                                                  23

<210> SEQ ID NO 29
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-29c microRNA

<400> SEQUENCE: 29
uagcaccauu ugaaaucggu ua                                                   22

<210> SEQ ID NO 30
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-342-3p microRNA

<400> SEQUENCE: 30
ucucacacag aaaucgcacc cgu                                                  23

<210> SEQ ID NO 31
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-125a-3p microRNA

<400> SEQUENCE: 31
acaggugagg uucuugggag cc                                                   22

<210> SEQ ID NO 32
<211> LENGTH: 21
<212> TYPE: RNA
<213> ORGANISM: Homo sapiens
<220> FEATURE:
```

```
<221> NAME/KEY: misc_feature
<223> OTHER INFORMATION: hsa-miR-23a microRNA

<400> SEQUENCE: 32
aucacauugc cagggauuuc c                                              21

<210> SEQ ID NO 33
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-31 microRNA

<400> SEQUENCE: 33
aggcaagaug cuggcauagc u                                              21

<210> SEQ ID NO 34
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-375 microRNA

<400> SEQUENCE: 34
uuuguucguu cggcucgcgu ga                                             22

<210> SEQ ID NO 35
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-551b microRNA

<400> SEQUENCE: 35
gcgacccaua cuugguuuca g                                              21

<210> SEQ ID NO 36
<211> LENGTH: 20
<212> TYPE: RNA
<213> ORGANISM: Homo sapiens
<220> FEATURE:
<221> NAME/KEY: misc_feature
<223> OTHER INFORMATION: hsa-miR-572 microRNA

<400> SEQUENCE: 36
guccgcucgg cgguggccca                                                20

<210> SEQ ID NO 37
<211> LENGTH: 25
<212> TYPE: RNA
<213> ORGANISM: Homo sapiens
<220> FEATURE:
<221> NAME/KEY: misc_feature
<223> OTHER INFORMATION: hsa-miR-638 microRNA

<400> SEQUENCE: 37
agggaucgcg ggcggguggc ggccu                                          25

<210> SEQ ID NO 38
<211> LENGTH: 21
<212> TYPE: RNA
<213> ORGANISM: Homo sapiens
<220> FEATURE:
<221> NAME/KEY: misc_feature
```

<223> OTHER INFORMATION: hsa-miR-650 microRNA

<400> SEQUENCE: 38
aggaggcagc gcucucagga c                                    21

<210> SEQ ID NO 39
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-7 microRNA

<400> SEQUENCE: 39
uggaagacua gugauuuugu ugu                                  23

<210> SEQ ID NO 40
<211> LENGTH: 24
<212> TYPE: RNA
<213> ORGANISM: Homo sapiens
<220> FEATURE:
<221> NAME/KEY: misc_feature
<223> OTHER INFORMATION: hsa-miR-939 microRNA

<400> SEQUENCE: 40
uggggagcug aggcucuggg ggug                                 24

<210> SEQ ID NO 41
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-150 microRNA

<400> SEQUENCE: 41
ucucccaacc cuuguaccag ug                                   22

<210> SEQ ID NO 42
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-18a microRNA

<400> SEQUENCE: 42
uaaggugcau cuagugcaga uag                                  23

<210> SEQ ID NO 43
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-19a microRNA

<400> SEQUENCE: 43
ugugcaaauc uaugcaaaac uga                                  23

<210> SEQ ID NO 44
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-424 microRNA

```
<400> SEQUENCE: 44
cagcagcaau ucauguuuug aa                                              22

<210> SEQ ID NO 45
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-552 microRNA

<400> SEQUENCE: 45
aacaggugac ugguuagaca a                                               21

<210> SEQ ID NO 46
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-92a microRNA

<400> SEQUENCE: 46
uauugcacuu gucccggccu gu                                              22

<210> SEQ ID NO 47
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-1 microRNA

<400> SEQUENCE: 47
uggaauguaa agaaguaugu au                                              22

<210> SEQ ID NO 48
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-133b microRNA

<400> SEQUENCE: 48
uuuggucccc uucaaccagc ua                                              22

<210> SEQ ID NO 49
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-20a microRNA

<400> SEQUENCE: 49
uaaagugcuu auagugcagg uag                                             23

<210> SEQ ID NO 50
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-378 microRNA
```

```
<400> SEQUENCE: 50
acuggacuug gagucagaag g                                              21

<210> SEQ ID NO 51
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-378* microRNA

<400> SEQUENCE: 51
cuccugacuc cagguccugu gu                                             22

<210> SEQ ID NO 52
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-181c microRNA

<400> SEQUENCE: 52
aacauucaac cugucgguga gu                                             22

<210> SEQ ID NO 53
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-592 microRNA

<400> SEQUENCE: 53
uugugucaau augcgaugau gu                                             22

<210> SEQ ID NO 54
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-452 microRNA

<400> SEQUENCE: 54
aacuguuugc agaggaaacu ga                                             22

<210> SEQ ID NO 55
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-139-5p microRNA

<400> SEQUENCE: 55
ucuacagugc acgugucucc ag                                             22

<210> SEQ ID NO 56
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-192 microRNA

<400> SEQUENCE: 56
```
cugaccuaug aauugacagc c								21

<210> SEQ ID NO 57
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-194 microRNA

<400> SEQUENCE: 57
uguaacagca acuccaugug ga								22

<210> SEQ ID NO 58
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-374b microRNA

<400> SEQUENCE: 58
auauaauaca accugcuaag ug								22

<210> SEQ ID NO 59
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-95 microRNA

<400> SEQUENCE: 59
uucaacgggu auuuauugag ca								22

<210> SEQ ID NO 60
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-139-3p microRNA

<400> SEQUENCE: 60
ggagacgcgg cccuguugga gu								22

<210> SEQ ID NO 61
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-29a microRNA

<400> SEQUENCE: 61
uagcaccauc ugaaaucggu ua								22

<210> SEQ ID NO 62
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-455-3p microRNA

<400> SEQUENCE: 62

```
gcaguccaug ggcauauaca c                                            21
```

<210> SEQ ID NO 63
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-25 microRNA

<400> SEQUENCE: 63

```
cauugcacuu gucucggucu ga                                           22
```

<210> SEQ ID NO 64
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-130b microRNA

<400> SEQUENCE: 64

```
cagugcaaug augaaagggc au                                           22
```

<210> SEQ ID NO 65
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-17* microRNA

<400> SEQUENCE: 65

```
acugcaguga aggcacuugu ag                                           22
```

<210> SEQ ID NO 66
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-20a* microRNA

<400> SEQUENCE: 66

```
acugcauuau gagcacuuaa ag                                           22
```

<210> SEQ ID NO 67
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-215 microRNA

<400> SEQUENCE: 67

```
augaccuaug aauugacaga c                                            21
```

<210> SEQ ID NO 68
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-10b microRNA

<400> SEQUENCE: 68

```
uacccuguag aaccgaauuu gug                                          23
```

```
<210> SEQ ID NO 69
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-19b microRNA

<400> SEQUENCE: 69
ugugcaaauc caugcaaaac uga                                               23

<210> SEQ ID NO 70
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-451 microRNA

<400> SEQUENCE: 70
aaaccguuac cauuacugag uu                                                22

<210> SEQ ID NO 71
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-143 microRNA

<400> SEQUENCE: 71
ugagaugaag cacuguagcu c                                                 21

<210> SEQ ID NO 72
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-145* microRNA

<400> SEQUENCE: 72
ggauuccugg aaauacuguu cu                                                22

<210> SEQ ID NO 73
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-22 microRNA

<400> SEQUENCE: 73
aagcugccag uugaagaacu gu                                                22

<210> SEQ ID NO 74
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-222 microRNA

<400> SEQUENCE: 74
agcuacaucu ggcuacuggg u                                                 21
```

<210> SEQ ID NO 75
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-122 microRNA

<400> SEQUENCE: 75
uggaguguga caauguguu ug                                    22

<210> SEQ ID NO 76
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-199b-5p microRNA

<400> SEQUENCE: 76
cccaguguuu agacuaucug uuc                                  23

<210> SEQ ID NO 77
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-365 microRNA

<400> SEQUENCE: 77
uaaugccccu aaaaauccuu au                                   22

<210> SEQ ID NO 78
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-660 microRNA

<400> SEQUENCE: 78
uacccauugc auaucggagu ug                                   22

<210> SEQ ID NO 79
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-100 microRNA

<400> SEQUENCE: 79
aacccguaga uccgaacuug ug                                   22

<210> SEQ ID NO 80
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-107 microRNA

<400> SEQUENCE: 80
agcagcauug uacagggcua uca                                  23

```
<210> SEQ ID NO 81
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-148b microRNA

<400> SEQUENCE: 81
ucagugcauc acagaacuuu gu                                                  22

<210> SEQ ID NO 82
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-204 microRNA

<400> SEQUENCE: 82
uucccuuugu cauccuaugc cu                                                  22

<210> SEQ ID NO 83
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-376c microRNA

<400> SEQUENCE: 83
aacauagagg aaauuccacg u                                                   21

<210> SEQ ID NO 84
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-625 microRNA

<400> SEQUENCE: 84 aggggggaaag uucuauaguc c                                                  21

<210> SEQ ID NO 85
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-429 microRNA

<400> SEQUENCE: 85
uaauacuguc ugguaaaacc gu                                                  22

<210> SEQ ID NO 86
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-127-3p microRNA

<400> SEQUENCE: 86
ucggauccgu cugagcuugg cu                                                  22

<210> SEQ ID NO 87
```

-continued

<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-199b-3p microRNA

<400> SEQUENCE: 87
acaguagucu gcacauuggu ua                                              22

<210> SEQ ID NO 88
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-26b microRNA

<400> SEQUENCE: 88
uucaaguaau ucaggauagg u                                               21

<210> SEQ ID NO 89
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-31* microRNA

<400> SEQUENCE: 89
ugcuaugcca acauauugcc au                                              22

<210> SEQ ID NO 90
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-483-3p microRNA

<400> SEQUENCE: 90
ugcuaugcca acauauugcc au                                              22

<210> SEQ ID NO 91
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-483-5p microRNA

<400> SEQUENCE: 91
aagacgggag gaaagaaggg ag                                              22

<210> SEQ ID NO 92
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-503 microRNA

<400> SEQUENCE: 92
uagcagcggg aacaguucug cag                                             23

<210> SEQ ID NO 93
<211> LENGTH: 22

-continued

<212> TYPE: RNA
<213> ORGANISM: Homo sapiens
<220> FEATURE:
<221> NAME/KEY: misc_feature
<223> OTHER INFORMATION: hsa-miR-513c microRNA

<400> SEQUENCE: 93
uucucaagga ggugucguuu au                                              22

<210> SEQ ID NO 94
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-26a microRNA

<400> SEQUENCE: 94
uucaaguaau ccaggauagg cu                                              22

<210> SEQ ID NO 95
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-1225-5p microRNA

<400> SEQUENCE: 95
guggguacgg cccagugggg gg                                              22

<210> SEQ ID NO 96
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-128 microRNA

<400> SEQUENCE: 96
ucacagugaa ccggucucuu u                                               21

<210> SEQ ID NO 97
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-134 microRNA

<400> SEQUENCE: 97
ugugacuggu ugaccagagg gg                                              22

<210> SEQ ID NO 98
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-194* microRNA

<400> SEQUENCE: 98
ccaguggggc ugcuguuauc ug                                              22

<210> SEQ ID NO 99
<211> LENGTH: 24
<212> TYPE: RNA

```
<213> ORGANISM: Homo sapiens
<220> FEATURE:
<221> NAME/KEY: misc_feature
<223> OTHER INFORMATION: hsa-miR-29b-1* microRNA

<400> SEQUENCE: 99
gcugguuuca uauggugguu uaga                                         24

<210> SEQ ID NO 100
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-30e microRNA

<400> SEQUENCE: 100
uguaaacauc cuugacugga ag                                           22

<210> SEQ ID NO 101
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-338-3p microRNA

<400> SEQUENCE: 101
uccagcauca gugauuuugu ug                                           22

<210> SEQ ID NO 102
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-34b* microRNA

<400> SEQUENCE: 102
uaggcagugu cauuagcuga uug                                          23

<210> SEQ ID NO 103
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-623 microRNA

<400> SEQUENCE: 103
aucccuugca ggggcuguug ggu                                          23

<210> SEQ ID NO 104
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-662 microRNA

<400> SEQUENCE: 104
ucccacguug uggcccagca g                                            21

<210> SEQ ID NO 105
<211> LENGTH: 22
<212> TYPE: RNA
<213> ORGANISM: Homo sapiens
```

```
<220> FEATURE:
<221> NAME/KEY: misc_feature
<223> OTHER INFORMATION: hsa-miR-98 microRNA

<400> SEQUENCE: 105
ugagguagua aguuguauug uu                                                  22

<210> SEQ ID NO 106
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-99a microRNA

<400> SEQUENCE: 106
aacccguaga uccgaucuug ug                                                  22

<210> SEQ ID NO 107
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-19b-1* microRNA

<400> SEQUENCE: 107
aguuuugcag guuugcaucc agc                                                 23

<210> SEQ ID NO 108
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-335 microRNA

<400> SEQUENCE: 108
ucaagagcaa uaacgaaaaa ugu                                                 23

<210> SEQ ID NO 109
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-766 microRNA

<400> SEQUENCE: 109
acuccagccc cacagccuca gc                                                  22

<210> SEQ ID NO 110
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-550* microRNA

<400> SEQUENCE: 110
ugucuuacuc ccucaggcac au                                                  22

<210> SEQ ID NO 111
<211> LENGTH: 21
<212> TYPE: RNA
<213> ORGANISM: Homo sapiens
<220> FEATURE:
```

```
<221> NAME/KEY: misc_feature
<223> OTHER INFORMATION: hsa-miR-151-3p microRNA

<400> SEQUENCE: 111
cuagacugaa gcuccuugag g                                              21

<210> SEQ ID NO 112
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-301a microRNA

<400> SEQUENCE: 112
cagugcaaua guauugucaa agc                                            23

<210> SEQ ID NO 113
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-335* microRNA

<400> SEQUENCE: 113
uuuuucauua uugcuccuga cc                                             22

<210> SEQ ID NO 114
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-342-5p microRNA

<400> SEQUENCE: 114
aggggugcua ucugugauug a                                              21

<210> SEQ ID NO 115
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-132 microRNA

<400> SEQUENCE: 115
uaacagucua cagccauggu cg                                             22

<210> SEQ ID NO 116
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-135a* microRNA

<400> SEQUENCE: 116
uauagggauu ggagccgugg cg                                             22

<210> SEQ ID NO 117
<211> LENGTH: 22
<212> TYPE: RNA
<213> ORGANISM: Homo sapiens
<220> FEATURE:
<221> NAME/KEY: misc_feature
```

```
<223> OTHER INFORMATION: hsa-miR-146b-5p microRNA

<400> SEQUENCE: 117
ugagaacuga auuccauagg cu                                              22

<210> SEQ ID NO 118
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-192* microRNA

<400> SEQUENCE: 118
cugccaauuc cauaggucac ag                                              22

<210> SEQ ID NO 119
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-23b microRNA

<400> SEQUENCE: 119
aucacauugc cagggauuac c                                               21

<210> SEQ ID NO 120
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-29c* microRNA

<400> SEQUENCE: 120
ugaccgauuu cuccuggugu uc                                              22

<210> SEQ ID NO 121
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-376a microRNA

<400> SEQUENCE: 121
aucauagagg aaaauccacg u                                               21

<210> SEQ ID NO 122
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-486-5p microRNA

<400> SEQUENCE: 122
uccuguacug agcugccccg ag                                              22

<210> SEQ ID NO 123
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-196b microRNA
```

<400> SEQUENCE: 123
uagguaguuu ccuguuguug gg                                          22

<210> SEQ ID NO 124
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 124
tgtaaaacga cggccagtac ttggtaaacg gaac                             34

<210> SEQ ID NO 125
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 125
tgtaaaacga cggccagtac ttggtaagca aaaa                             34

<210> SEQ ID NO 126
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 126
tgtaaaacga cggccagtac ttggtatcaa catc                             34

<210> SEQ ID NO 127
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 127
tgtaaaacga cggccagtac ttggtaagtg tgag                             34

<210> SEQ ID NO 128
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 128
tgtaaaacga cggccagtac ttggtaagtg aatt                             34

<210> SEQ ID NO 129
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 129
tgtaaaacga cggccagtac ttggtagaaa ccca                             34

<210> SEQ ID NO 130

```
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 130
tgtaaaacga cggccagtac ttggtaacaa acca                                34

<210> SEQ ID NO 131
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 131
tgtaaaacga cggccagtac ttggtactac ctgc                                34

<210> SEQ ID NO 132
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 132
tgtaaaacga cggccagtac ttggtaatct gcac                                34

<210> SEQ ID NO 133
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 133
tgtaaaacga cggccagtac ttggtactaa ctgc                                34

<210> SEQ ID NO 134
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 134
tgtaaaacga cggccagtac ttggtacttc cagt                                34

<210> SEQ ID NO 135
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 135
tgtaaaacga cggccagtac ttggtatcac atag                                34

<210> SEQ ID NO 136
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 136
```
tgtaaaacga cggccagtac ttggtactac ctgc                              34

<210> SEQ ID NO 137
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 137
tgtaaaacga cggccagtac ttggtactac ctgc                              34

<210> SEQ ID NO 138
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 138
tgtaaaacga cggccagtac ttggtactac ctgc                              34

<210> SEQ ID NO 139
<211> LENGTH: 35
<212> TYPE: DNA
<213> ORGANISM: Artificial Sequence
<220> FEATURE:
<223> OTHER INFORMATION: Artificially synthesized oligonucleotide primer

<400> SEQUENCE: 139
tgtaaaacga cggccagtac ttggtactgt tcctg                             35

<210> SEQ ID NO 140
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 140
tgtaaaacga cggccagtac ttggtaaaag tctc                              34

<210> SEQ ID NO 141
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 141
tgtaaaacga cggccagtac ttggtaaact atac                              34

<210> SEQ ID NO 142
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 142
caagtcacta gtggttccg                                               19

<210> SEQ ID NO 143
<211> LENGTH: 21
<212> TYPE: DNA

<213> ORGANISM: Artificial Sequence
<220> FEATURE:
<223> OTHER INFORMATION: Artificially synthesized oligonucleotide primer

<400> SEQUENCE: 143
tttggcacta gcacattttt g                                          21

<210> SEQ ID NO 144
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 144
tagcttatca gactgatgtt ga                                         22

<210> SEQ ID NO 145
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 145
tttggcaatg gtagaactca c                                          21

<210> SEQ ID NO 146
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 146
tatggcactg gtagaattca c                                          21

<210> SEQ ID NO 147
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 147
agctacattg tctgctgg                                              18

<210> SEQ ID NO 148
<211> LENGTH: 16
<212> TYPE: DNA
<213> ORGANISM: Artificial Sequence
<220> FEATURE:
<223> OTHER INFORMATION: Artificially synthesized oligonucleotide primer

<400> SEQUENCE: 148
cagcagcaca ctgtgg                                                16

<210> SEQ ID NO 149
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 149
aaaagtgctt acagtgcag                                             19

<210> SEQ ID NO 150
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 150
taaagtgctg acagtgca                                                   18

<210> SEQ ID NO 151
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 151
taaggtgcat ctagtgcag                                                  19

<210> SEQ ID NO 152
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 152
tgtaaacatc ctcgactgg                                                  19

<210> SEQ ID NO 153
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 153
tatggctttt cattcctatg                                                 20

<210> SEQ ID NO 154
<211> LENGTH: 17
<212> TYPE: DNA
<213> ORGANISM: Artificial Sequence
<220> FEATURE:
<223> OTHER INFORMATION: Artificially synthesized oligonucleotide primer

<400> SEQUENCE: 154
caaagtgctg ttcgtgc                                                    17

<210> SEQ ID NO 155
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 155
caaagtgctt acagtgca                                                   18

<210> SEQ ID NO 156
<211> LENGTH: 17
<212> TYPE: DNA
<213> ORGANISM: Artificial Sequence
<220> FEATURE:

```
<223> OTHER INFORMATION: Artificially synthesized oligonucleotide primer

<400> SEQUENCE: 156
caaagtgctc atagtgc                                                    17

<210> SEQ ID NO 157
<211> LENGTH: 17
<212> TYPE: DNA
<213> ORGANISM: Artificial Sequence
<220> FEATURE:
<223> OTHER INFORMATION: Artificially synthesized oligonucleotide primer

<400> SEQUENCE: 157
tggctcagtt cagcagg                                                    17

<210> SEQ ID NO 158
<211> LENGTH: 15
<212> TYPE: DNA
<213> ORGANISM: Artificial Sequence
<220> FEATURE:
<223> OTHER INFORMATION: Artificially synthesized oligonucleotide primer

<400> SEQUENCE: 158
tgaggggcag agagc                                                      15

<210> SEQ ID NO 159
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 159
tgaggtagta ggttgtat                                                   18

<210> SEQ ID NO 160
<211> LENGTH: 17
<212> TYPE: DNA
<213> ORGANISM: Artificial Sequence
<220> FEATURE:
<223> OTHER INFORMATION: Artificially synthesized oligonucleotide primer

<400> SEQUENCE: 160
tgtaaaacga cggccag                                                    17
```